(12) United States Patent
Ohta et al.

(10) Patent No.: US 8,232,031 B2
(45) Date of Patent: Jul. 31, 2012

(54) NAPHTHALENETETRACARBOXYLIC ACID DIIMIDE DERIVATIVE AND ELECTROPHOTOGRAPHIC PHOTOCONDUCTOR HAVING THE SAME

(75) Inventors: Masafumi Ohta, Susono (JP); Tomoyuki Shimada, Shizuoka (JP); Yuuji Tanaka, Fujinomiya (JP); Eiji Kurimoto, Numazu (JP); Keisuke Shimoyama, Numazu (JP)

(73) Assignee: Ricoh Company, Ltd., Tokyo (JP)

( * ) Notice: Subject to any disclaimer, the term of this patent is extended or adjusted under 35 U.S.C. 154(b) by 720 days.

(21) Appl. No.: 12/205,143

(22) Filed: Sep. 5, 2008

(65) Prior Publication Data

US 2009/0068577 A1    Mar. 12, 2009

(30) Foreign Application Priority Data

Sep. 10, 2007  (JP) .................. 2007-233658
Dec. 6, 2007   (JP) .................. 2007-315717
May 2, 2008    (JP) .................. 2008-120125

(51) Int. Cl.
    *G03G 5/047* (2006.01)
(52) U.S. Cl. ............... 430/58.85; 430/58.05; 430/58.5; 430/58.55; 430/58.65
(58) Field of Classification Search ............... 430/58.05, 430/58.5, 58.55, 58.65, 58.85
    See application file for complete search history.

(56) References Cited

U.S. PATENT DOCUMENTS 5,468,583 A     11/1995  Gruenbaum et al.
5,567,560 A *   10/1996  Hagiwara et al. .......... 430/58.85

(Continued)

FOREIGN PATENT DOCUMENTS

CN    1932663 A    3/2007

(Continued)

OTHER PUBLICATIONS

Translation of JP 11-305465 published Nov. 1999.*

(Continued)

*Primary Examiner* — Peter Vajda
(74) *Attorney, Agent, or Firm* — Cooper & Dunham LLP

(57) ABSTRACT

The present invention provides a naphthalenetetracarboxylic acid diimide derivative represented by the following general formula (1):

General Formula (1)

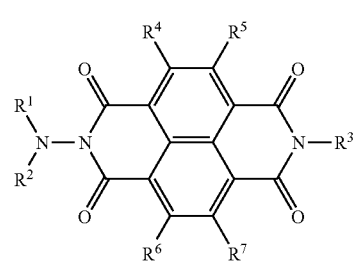

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; and $R^1$ and $R^2$ may be linked to form a substituted or non-substituted heterocyclic group including a nitrogen atom; with compounds where all of $R^1$, $R^2$ and $R^3$ are a methyl group, and compounds where both of $R^1$ and $R^2$ are a methyl group and $R^3$ is a 1-octyl group being excluded.

11 Claims, 7 Drawing Sheets

2 θ (deg.)

U.S. PATENT DOCUMENTS

| | | | |
|---|---|---|---|
| 6,794,102 B2 | 9/2004 | Bender et al. | |
| 2005/0260511 A1 * | 11/2005 | Kunieda et al. | 430/58.8 |
| 2007/0059039 A1 * | 3/2007 | Shimoyama et al. | 399/159 |
| 2007/0059618 A1 | 3/2007 | Kurimoto et al. | |
| 2007/0219375 A1 | 9/2007 | Fujiyama et al. | |
| 2010/0260515 A1 | 10/2010 | Shimoyama et al. | |

FOREIGN PATENT DOCUMENTS

| | | | |
|---|---|---|---|
| DE | 1230031 | | 12/1966 |
| EP | 1736476 A1 | | 12/2006 |
| JP | 60-196768 | | 10/1985 |
| JP | 1-206349 | | 8/1989 |
| JP | 2718048 | | 11/1997 |
| JP | 2732697 | | 12/1997 |
| JP | 2884353 | | 2/1999 |
| JP | 11-305465 | * | 11/1999 |
| JP | 2000-231204 | | 8/2000 |
| JP | 2002-534552 | | 10/2002 |
| JP | 2004-258253 | | 9/2004 |
| JP | 2005-154409 | | 6/2005 |
| JP | 2005-320288 | * | 11/2005 |
| JP | 4101676 | | 3/2008 |
| WO | WO 00/40657 | | 7/2000 |
| WO | WO 02/40479 A1 | | 5/2002 |

OTHER PUBLICATIONS

Translation of JP 2005-320288 published Nov. 2005.*

Itami, Akihiko, et al. "The Effects of Nitrogen Oxide on the Resolution of Organic Photoconductors", *Konica Technical Report*, vol. 13, pp. 37-40, 2000.

Katz, Howard, et al. "Unsymmetrical $n$-Channel Semiconducting Naphthalenetetracarboxylic Diimides Assembled via Hydrogen Bonds", *Chemistry Letters*, vol. 32., No. 6, pp. 508-509, May 13, 2003.

U.S. Appl. No. 12/132,026, filed Jun. 3, 2008.

European search report in connection with a counterpart European patent application No. 08 16 3978.

Oct. 8, 2010 Chinese official action (and English translation thereof) in connection with a counterpart Chinese patent application.

* cited by examiner

NAPHTHALENETETRACARBOXYLIC ACID DIIMIDE DERIVATIVE AND ELECTROPHOTOGRAPHIC PHOTOCONDUCTOR HAVING THE SAME

BACKGROUND OF THE INVENTION

1. Field of the Invention

The present invention relates to novel naphthalenetetracarboxylic acid diimide derivatives which are useful for an organic electronics material, particularly for an organic photoconductor material.

The present invention also relates to electrophotographic photoconductors including a photoconductive layer containing at least one of the naphthalenetetracarboxylic acid diimide derivatives.

2. Description of the Related Art

Organic electrophotographic photoconductors, which have been widely put into practice, contain an organic photoconductor material. The organic photoconductor material has been required to meet more strict requirements; e.g., higher sensitivity and applicability to environmentally sensitive production methods or processes.

The organic electrophotographic photoconductor is formed from a charge generation material and a charge transport material. The charge transport material is required to have higher sensitivity; i.e., to exhibit high charge transferrability (carrier transferrability). Currently, hole transport materials, which exhibit practical applicability, are employed in many cases.

Nevertheless, further advancement of organic electronics materials (e.g., organic photoconductor materials) depends on development of a charge transport material having high performance for transporting both holes and electrons (i.e., carriers). In view of this, demand has arisen for an electron transport material exhibiting high charge transferrability (carrier transferrability).

In recent years, information processing devices based on electrophotography have been remarkably developing. In particular, laser printers and digital copiers, which convert information to digital signals and record it using light beams, have been drastically improving in reliability and printing image quality. Further, high-speed technologies allow some of the printers and copiers to achieve full-color printing. Thus, photoconductors are particularly required to attain both high image quality and high durability.

The photoconductors used in the electorophotographic laser printers, digital copiers, etc. are generally formed of an organic photoconductor (OPC) material, from the viewpoints of reducing costs, enhancing productivity, and avoiding environmental pollution. In general, the OPC material-containing photoconductor has a single-layer structure or a functionally-separated multi-layer structure. A PVK-TNF charge-transfer complex photoconductor, which is the first practical OPC-photoconductor, has a single-layer structure.

In 1968, Hayashi and Regensburger independently invented a PVK/a-Se multi-layer photoconductor. Melz et al. (in 1977) and Schlosser (in 1978) reported a multi-layer photoconductor having an organic pigment-dispersed layer and an organic low-molecular-weight compound-dispersed polymer layer; i.e., having only organic photoconductive layers. These multi-layer photoconductors are called a functionally-separated multi-layer photoconductor, since they contain a charge generation layer (CGL), where charges are generated upon absorbing light; and a charge transport layer (CTL), through which the generated charges are transported to neutralize the surface charges.

Organic photoconductors suffer from greater film ablation caused by repetitive use, as compared with inorganic photoconductors. Ablation of the photoconductive layer, which constitutes the photoconductor, leads to reduction in charge potential and deterioration of photosensitivity. In addition, background smears are easily generated by the irregularities of the photoconductor surface, and the formed image density or quality tends to be deteriorated. Thus, conventionally, organic photoconductors have been required to have sufficient wear resistance. Furthermore, since photoconductors become smaller in accordance with increased high-speed performance or downsizing of electrophotographic apparatus, much importance is placed on providing highly durable organic photoconductors.

As has been widely known, wear resistance of photoconductors is increased by curing the photoconductive layer, by imparting lubricity thereto, by incorporating a filler thereinto, or by using a charge transport polymer instead of a low-molecular-weight charge transport material (CTM)-dispersed polymer layer. However, problems newly arise by employing the above method for preventing the photoconductive layer from ablation. Specifically, on a surface of the photoconductive layer are adsorbed ozone, NOx and oxidation substances generated as a result of repetitive use or in response to ambient environment. The surface may be reduced in resistivity after repetitive use or in response to the working environment, causing problematic image blur. This image blur has conventionally been improved in some degree by ablation, together with the photoconductive layer, of these image-blur-causing substances.

However, new countermeasures must be taken for meeting the recent requirements; i.e., higher resolution and higher durability. In one proposed method for reducing the adverse effects of the image-blur-causing substances, the photoconductor is provided with a heater. However, provision of the heater is a grave obstacle to downsizing of an electrophotographic apparatus or to reduction of power consumption. Also, use of additives (e.g., an antioxidant) is advantageous. However, since usual additives have no photoconductivity, the photoconductive layer containing a large amount of additives exhibits deteriorated electrophotographic properties such as reduced sensitivity and increased residual potential.

As described above, electrophotographic photoconductors exhibit a reduced degree of ablation with a result of changing the process design therearound or imparting high wear resistance thereto, but these unavoidably give adverse side effects to image quality; e.g., image blur and reduction of resolution. Thus, difficulty has been encountered in fabricating electrophotographic photoconductors having both high durability and high image quality. In other words, they preferably have higher resistivity for preventing image blur, and in contrast, they preferably have lower resistivity for preventing increase in residual potential, which causes trade-off therebetween.

Most practical electrophotographic photoconductors have a functionally-separated multi-layer structure, which includes a conductive support, a charge generation layer, and a charge transport layer containing hole transport materials, with the layers being provided on the support. These electrophotographic photoconductors are generally used in negative electrophotographic processes.

In the electrophotographic processes, corona charging is reliably used for charging. Most copiers and printers employ this charging method. Nevertheless, as has been known well, negative corona charging is unstable compared with positive corona charging. Thus, a scorotron charger is employed, which leads to cost elevation. In addition, negative corona charging generates a larger amount of ozone which may give chemical damage to photoconductors. Thus, when the devices employing negative corona charging are used for a long period of time, the generated ozone during charging deteriorates through oxidation binder resin and charge transfer materials. Furthermore, ionic compounds (e.g., nitrogen oxide ions, sulfur oxide ions and ammonium ions) are also generated during charging, accumulation of such ionic compounds on the photoconductor causes problematic deterioration of image quality. Meanwhile, ozone is also an environmental pollutant and thus, generation of a large amount thereof is problematic. In view of this, for the purpose of preventing ozone from being released outside, ozone filters are often used in negatively-charged copiers or printers, which also causes cost elevation in these devices.

In order to solve the above-described problems, development of positively-charged type electrophotographic photoconductors has been continued. Employment of positively charging reduces generation of ozone, nitrogen oxide ions, etc. Furthermore, when widely-used two-component developers are employed, the positively-charged electrophotographic photoconductors are less affected by environmental factors, and can consistently provide desired images. Thus, the positively-charged electrophotographic photoconductor is preferred from the viewpoints as described above.

In the positively-charged single-layer photoconductor or reverse multi-layer photoconductor (CGL/CTL), charge generation materials are present in the vicinity of the photoconductor surface. The charge generation materials are very susceptible to oxidation substances such as ozone and nitrogen oxide ions and thus, the photoconductors of this type pose a problem in that they are highly susceptible to gas contained in the working environment (e.g., discharge gas from fan heaters or vehicles).

In high-speed copying processes, negatively-charged photoconductors are more preferable than positively-charged photoconductors. This is because, among existing organic materials, only hole transport materials (i.e., materials transferring only holes) exhibit such high charge mobility that is applicable to the high-speed copying processes, and normal multi-layer electrophotographic photoconductors (CTL/CGL) are only negatively charged.

As described above, electrophotographic photoconductors that can be both positively and negatively charged can be used in a wide variety of applications. In addition, cost reduction can be realized by decreasing the number of photoconductor products. Furthermore, they can be advantageously employed in high-speed processes.

Under such circumstances, Japanese Patent (JP-B) No. 2732697 discloses an electrophotographic photoconductor which can be both positively and negatively charged. This electrophotographic photoconductor contains a diphenoquinone derivative serving as an electron transport material. The diphenoquinone derivative has rather low charge mobility and thus, the electrophotographic photoconductor does not exhibit such sensitivity that is sufficiently applicable to high-speed, downsized copiers or printers. Furthermore, it causes problematic image blur as a result of repetitive use.

Japanese Patent Application Laid-Open (JP-A) No. 2000-231204 discloses a dialkylamino group-containing aromatic compound which is incorporated into photoconductors as an acid-neutralizing agent. The photoconductors containing this compound maintain satisfactory image quality even when repeatedly used. However, this compound has low charge transferrability and thus, the photoconductors are difficult to meet high-sensitive, high-speed requirements, which imposes limitation on the compound content.

JP-A No. 60-196768, JP-B No. 2884353, and other literature disclose a dialkylamino group-containing stilbene compounds. From the literature "Itami et al., KONICA Technical Report, Vol. 13, p. 37, 2000", these stilbene compounds generate anti-oxidation gas and prevent image blur.

These compounds have a dialkylamino group as a substituent exhibiting a strong mesomeric effect (+M effect) at a resonance site of the triarylamine structure serving as a charge transporting site. Thus, the compounds exhibit extremely low ionization potential. The photoconductive layer containing, as a hole transport material, only the compound exhibits considerably deteriorated charge retention capability from the beginning of use or after repetitive use. The electrophotographic photoconductors having such a photoconductive layer pose a critical problem in that they are very difficult to put into practice. Even when used in combination with another charge transport material, the stilbene compound, in many cases, has ionization potential considerably lower than that of the material, making hole-trap sites for charge transfer. Thus, the formed electrophotographic photoconductors exhibit drastically reduced sensitivity and high residual potential.

JP-A No. 2004-258253 discloses a photoconductor containing a stilbene compound and a specific diamine compound. The photoconductor can be repeatedly used without reducing sensitivity thereof and exhibits improved environmental stability against, for example, oxidation gas.

The photoconductor, however, has not yet realized high-speed printing and downsizing of an electrophotographic apparatus.

Naphthalenetetracarboxylic acid diimide derivatives are reported to be used as an acceptor for forming a charge transfer complexes (see, for example, Germany Patent No. 1230031 (AUSLEGESCHRIFT 1230031)); or are reported to be used as a compound (pharmaceutical drug) exhibiting anti-helicobacter activity (see International Publication No. 02/040479). However, in the above literature, they are not suggested to be used in electrophotographic photoconductors. Separately, U.S. Pat. No. 5,468,583 describes use, as an electron transport material, of bis-N-alkyl-naphthalenetetracarboxylic acid diimide derivatives having a different structure from naphthalenetetracarboxylic acid diimide derivatives of the present invention. Electrophotographic photoconductors containing the bis-N-alkyl-naphthalenetetracarboxylic acid diimide derivative pose a problem in that they cause image blur after repetitive use.

The aforementioned JP-B No. 2732697 suggests use of diphenoquinone derivatives as an electron transport material used in electrophotographic photoconductors. JP-A No. 2005-154409 and U.S. Pat. No. 6,794,102 disclose naphthalenetetracarboxylic acid diimide derivatives. The literature "Chemistry letters (2003), 32(6), 508-509"describes semi-conductive materials formed of a naphthalenetetracarboxylic acid diimide derivative having the following structural formula (1). The International Publication No. 00/040657 describes electron transport materials formed of naphthalenetetracarboxylic acid diimide derivatives having the following structural formulas (2) and (3).

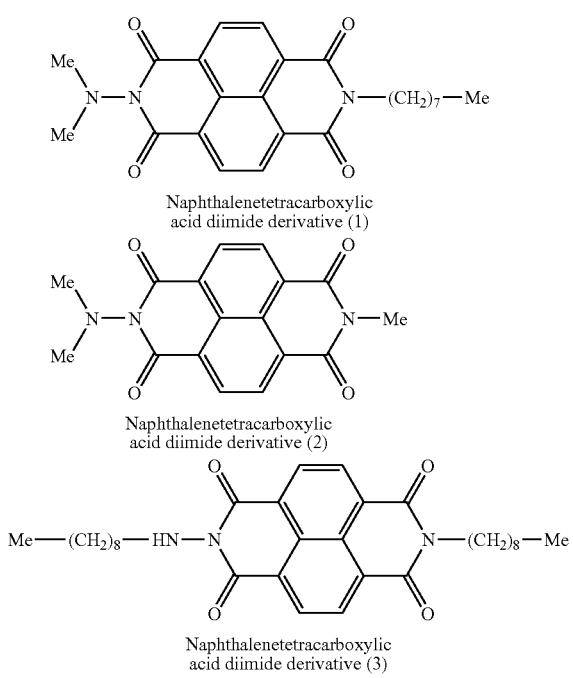

Naphthalenetetracarboxylic acid diimide derivative (1)

Naphthalenetetracarboxylic acid diimide derivative (2)

Naphthalenetetracarboxylic acid diimide derivative (3)

As has already been described above, the diphenoquinone derivative described in JP-B No. 2732697 has rather low charge mobility and thus, the photoconductors containing it do not exhibit such sensitivity that is sufficiently applicable to high-speed, downsized copiers or printers. Furthermore, this derivative causes problematic image blur as a result of repetitive use. The diphenoquinone derivatives described in JP-B No. 2732697, the naphthalenetetracarboxylic acid diimide derivative (2) or (3) described in the International Publication No. 00/040657, and diphenoquinone derivatives described in JP-A No. 01-206349 have poor compatibility to binder resin forming photoconductors, failing to sufficiently exhibit their characteristics. The naphthalenetetracarboxylic acid diimide derivative described in JP-A No. 2005-154409 and U.S. Pat. No. 6,794,102 have a complicated structure, involving problems in production thereof The naphthalenetetracarboxylic acid diimide derivative (1) described in the literature "Chemistry letters (2003), 32(6), 508-509" has low electron transferrability, not being applicable to practical use.

BRIEF SUMMARY OF THE INVENTION

The present invention provides the following in order to solve the above-described problems. Specifically, an object of the present invention is to provide novel naphthalenetetracarboxylic acid diimide derivatives which serve as an electron transport material and which are organic electronics materials advantageously used in various devices such as electrophotographic photoconductors, photoelectric transducers, thin-layer transistors and light-emitting devices.

Another object of the present invention is to provide an electrophotographic photoconductor which exhibits high durability to long-term repetitive use; which prevents image deterioration, which would otherwise be caused by reduction in image density or by generation of image blur; and which can consistently provide high-quality images. Still another object of the present invention is to provide an electrophotographic apparatus, an electrophotographic method and an electrophotographic process cartridge which use a downsized photoconductor, without exchange thereof, which can be both positively and negatively charged; which realize high-speed printing and downsizing of an electrophotographic apparatus; and which can consistently provide high-quality images even when repeatedly used.

Accordingly, the present invention provides the following.
<1> A naphthalenetetracarboxylic acid diimide derivative represented by the following general formula (1):

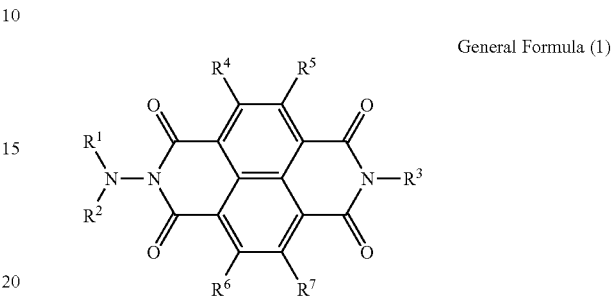

General Formula (1)

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; and $R^1$ and $R^2$ may be linked to form a substituted or non-substituted heterocyclic group including a nitrogen atom; with compounds where all of $R^1$, $R^2$ and $R^3$ are a methyl group, and compounds where both of $R^1$ and $R^2$ are a methyl group and $R^3$ is a 1-octyl group being excluded.

<2> A naphthalenetetracarboxylic acid diimide derivative represented by the following general formula (I):

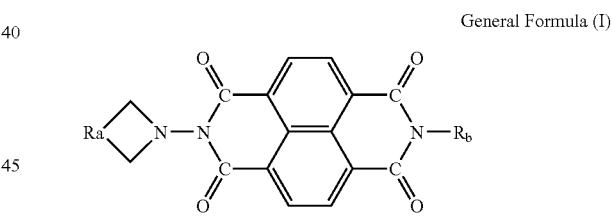

General Formula (I)

wherein $R_a$ represents a divalent group necessary for forming a nitrogen-containing ring together with a nitrogen atom and a carbon atom; a nitrogen-containing ring moiety represented by the following general formula (II) represents a substituted or non-substituted saturated or unsaturated ring which may further contain a nitrogen atom or an oxygen atom; when the nitrogen-containing ring moiety is a ring having a plurality of substituents, the substituents may form a condensed ring together with a part of the nitrogen-containing ring; and $R_b$ represents an amino-substituted or non-substituted branched alkyl group or an amino-substituted or non-substituted branched alkoxyalkyl group.

General Formula (II)

<3> The naphthalenetetracarboxylic acid diimide derivative according to <2> above, wherein the moiety represented by general formula (II) is a substituted or non-substituted piperidine, a substituted or non-substituted pyrrolidine, a substituted or non-substituted homopiperidine, a substituted or non-substituted piperazine, or a substituted or non-substituted morpholine.

<4> A charge transport material for use in an electrophotographic photoconductor, including the naphthalenetetracarboxylic acid diimide derivative according to any one of <1> to <3> above.

<5> An electrophotographic photoconductor including a conductive support and a photoconductive layer provided on the conductive support, wherein the photoconductive layer contains a first charge transport material containing the naphthalenetetracarboxylic acid diimide derivative according to any one of <1> to <3> above.

<6> The electrophotographic photoconductor according to <5> above, wherein the photoconductive layer further contains a second charge transport material.

<7> The electrophotographic photoconductor according to <6> above, wherein the second charge transport material is a derivative represented by the following general formula (2):

General Formula (2)

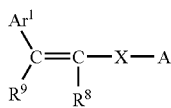

wherein X represents a single bond or a vinylene group; $R^8$ represents a hydrogen atom, a substituted or non-substituted alkyl group, or a substituted or non-substituted aromatic hydrocarbon group; $Ar^1$ represents a substituted or non-substituted aromatic hydrocarbon group; $R^9$ represents a hydrogen atom, a substituted or non-substituted alkyl group, or a substituted or non-substituted aromatic hydrocarbon group; $Ar^1$ and $R^9$ may be linked to form a ring; and A represents a group represented by the following general formula (3) or (4), a 9-anthryl group, or a substituted or non-substituted carbazolyl group;

General Formula (3)

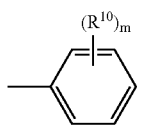

wherein $R^{10}$ represents a hydrogen atom, an alkyl group, an alkoxy group, a halogen atom, or a group represented by the following general formula (5); m is an integer of 1 to 3; and when m is two or more, $R^{10}$s may be identical or different;

General Formula (4)

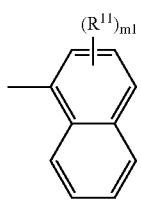

wherein $R^{11}$ represents a hydrogen atom, an alkyl group, an alkoxy group, a halogen atom, or a group represented by the following general formula (5); m1 is an integer of 1 to 3; and when m1 is two or more, $R^{11}$s may be identical or different; and General Formula (5)

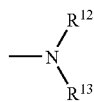

wherein $R^{12}$ and $R^{13}$, which may be identical or different, each represent a substituted or non-substituted alkyl group, or a substituted or non-substituted aromatic hydrocarbon group; and $R^{12}$ and $R^{13}$ may be linked to form a ring.

<8> The electrophotographic photoconductor according to <6> above, wherein the second charge transport material is a derivative represented by the following general formula (6):

General Formula (6)

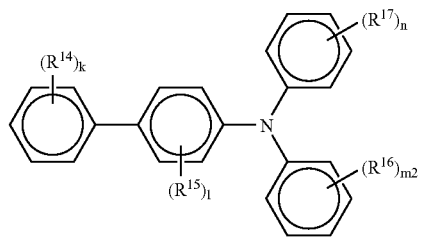

wherein $R^{14}$, $R^{16}$ and $R^{17}$ each represent a hydrogen atom, an amino group, an alkoxy group, a thioalkoxy group, an aryloxy group, a methylenedioxy group, a substituted or non-substituted alkyl group, a halogen atom, or a substituted or non-substituted aromatic hydrocarbon group; $R^{15}$ represents a hydrogen atom, an alkoxy group, a substituted or non-substituted alkyl group, or a halogen atom; k, l, m2 or n is an integer of 1, 2, 3 or 4; when k is an integer of 2, 3 or 4, $R^{14}$s may be identical or different; when l is an integer of 2, 3 or 4, $R^{15}$s may be identical or different; when m2 is an integer of 2, 3 or 4, $R^{16}$s may be identical or different; and when n is an integer of 2, 3 or 4, $R^{17}$s may be identical or different.

<9> The electrophotographic photoconductor according to <6> above, wherein the second charge transport material is a derivative represented by the following general formula (7):

General Formula (7)

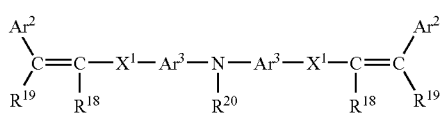

wherein $X^1$ represents a single bond or a vinylene group; $R^{18}$ represents a hydrogen atom, a substituted or non-substituted alkyl group, or a substituted or non-substituted aromatic hydrocarbon group; $Ar^2$ represents a substituted or non-substituted aromatic hydrocarbon group; $R^{19}$ represents a hydrogen atom, a substituted or non-substituted alkyl group, or a substituted or non-substituted aromatic hydrocarbon group; $Ar^2$ and $R^{19}$ may be linked to form a ring; $Ar^3$ represents a divalent group represented by the following general formula (8) or (9); and $R^{20}$ represents a substituted or non-substituted alkyl group, or a substituted or non-substituted aromatic hydrocarbon group;

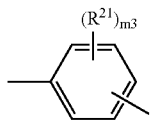
General Formula (8)

wherein $R^{21}$ represents a hydrogen atom, an alkyl group, an alkoxy group or a halogen atom; m3 is an integer of 1 to 3; and when m3 is two or more, $R^{21}$s may be identical or different; and

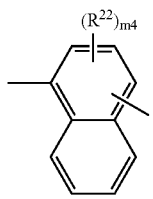
General Formula (9)

wherein $R^{22}$ represents a hydrogen atom, an alkyl group, an alkoxy group or a halogen atom; m4 is an integer of 1 to 3; and when m4 is two or more, $R^{22}$s may be identical or different.

<10> The electrophotographic photoconductor according to <6> above, wherein the second charge transport material is a derivative represented by the following general formula (10):

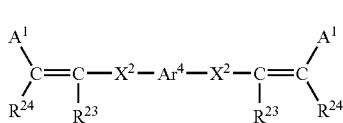
General Formula (10)

wherein $X^2$ represents a single bond or a vinylene group; $R^{23}$ represents a hydrogen atom, a substituted or non-substituted alkyl group, or a substituted or non-substituted aromatic hydrocarbon group; $Ar^4$ represents a substituted or non-substituted divalent aromatic hydrocarbon group; $R^{24}$ represents a hydrogen atom, a substituted or non-substituted alkyl group, or a substituted or non-substituted aromatic hydrocarbon group; and $A^1$ represents a group represented by the following general formula (3) or (4), a 9-anthryl group, or a substituted or non-substituted carbazolyl group;

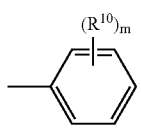
General Formula (3)

wherein $R^{10}$ represents a hydrogen atom, an alkyl group, an alkoxy group, a halogen atom, or a group represented by the following general formula (5); m is an integer of 1 to 3; and when m is two or more, $R^{10}$s may be identical or different;

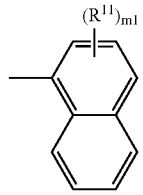
General Formula (4)

wherein $R^{11}$ represents a hydrogen atom, an alkyl group, an alkoxy group, a halogen atom, a group represented by the following general formula (5); m1 is an integer of 1 to 3; and when m1 is two or more, $R^{11}$s may be identical or different; and

General Formula (5)

wherein $R^{12}$ and $R^{13}$, which may be identical or different, each represent a substituted or non-substituted alkyl group, or a substituted or non-substituted aromatic hydrocarbon group; and $R^{12}$ and $R^{13}$ may be linked to form a ring.

<11> The electrophotographic photoconductor according to any one of <5> to <10>, wherein the photoconductive layer includes, in sequence, a conductive support, a charge generation layer and a charge transport layer.

<12> The electrophotographic photoconductor according to any one of <5> to <10>, wherein the photoconductive layer includes, in sequence, a conductive support, a charge transport layer and a charge generation layer.

<13> The electrophotographic photoconductor according to any one of <5> to <10>, wherein the photoconductive layer has a single-layer structure.

<14> An electrophotographic method, wherein the electrophotographic photoconductor according to any one of <5> to <13> is repeatedly subjected to a cycle including charging, imagewise light exposure, development and transfer.

<15> A digital electrophotographic method, wherein the electrophotographic photoconductor according to any one of <5> to <13> is repeatedly subjected to a cycle including charging, imagewise light exposure, development and transfer, wherein an electrostatic latent image is written on the electrophotographic photoconductor with an LD or LED during the imagewise light exposure.

<16> An electrophotographic apparatus including, a charging unit, an imagewise-light-exposing unit, a developing unit, a transferring unit and the electrophotographic photoconductor according to any one of <5> to <13> above.

<17> A digital electrophotographic apparatus including, a charging unit, an imagewise-light-exposing unit, a developing unit, a transferring unit and the electrophotographic photoconductor according to any one of <5> to <13> above, wherein an electrostatic latent image is written on the electrophotographic photoconductor with an LD or LED used in the imagewise-light-exposing unit.

<18> An electrophotographic process cartridge including the electrophotographic photoconductor according to any one of <5> to <13> above.

The present novel naphthalenetetracarboxylic acid diimide derivatives exhibit excellent electron transferrability, and are advantageously used as organic photoconductor materials in high-sensitive electrophotographic photoconductors.

The present invention can solve the above-described problems and achieve the above-described objects. The naphthalenetetracarboxylic acid diimide derivatives represented by general formula (1) allow photoconductors to maintain their sensitivity, to exhibit high durability to repetitive use, to exhibit remarkably enhanced environmental stability against, for example, oxidation gas, and to provide high-resolution images for a long period of time. The present invention provides electrophotographic photoconductors which realize both high durability and high image quality, which consistently provide high-quality images for a long period of time, and which are both positively and negatively charged. Also, the present invention provides an electrophotographic method, apparatus and process cartridge having the electrophotographic photoconductor.

DETAILED DESCRIPTION OF THE INVENTION

Figure 1:
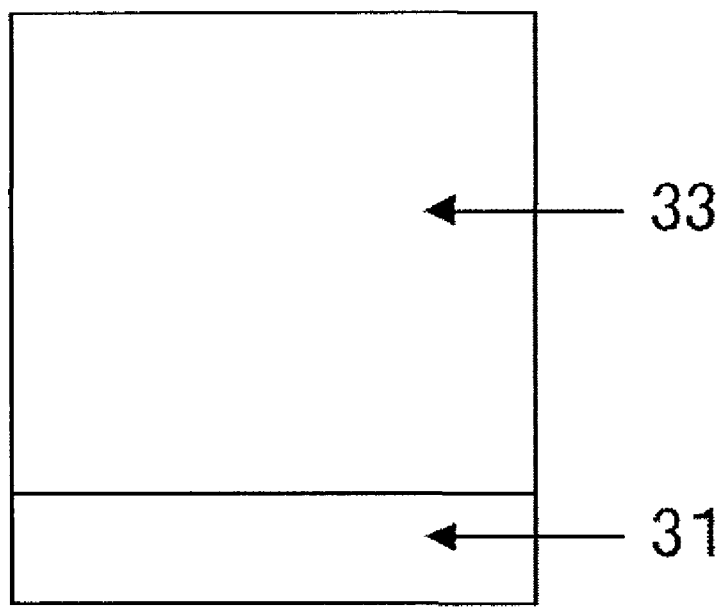
FIG. 1 is a cross-sectional view of a first electrophotographic photoconductor of the present invention.

With reference to the drawings, next will be described naphthalenetetracarboxylic acid diimide derivatives of the present invention, and an electrophotographic photoconductors containing the naphthalenetetracarboxylic acid diimide derivatives.

(Naphthalenetetracarboxylic Acid Diimide Derivative)

The present inventors carried out extensive studies, and have found that a photoconductive layer containing at least one of the naphthalenetetracarboxylic acid diimide derivatives represented by the following general formula (1) allows a photoconductor to be both positively and negatively charged and to solve the above-described problems; e.g., image blur caused by oxidation gas (an image-blur-causing substance).

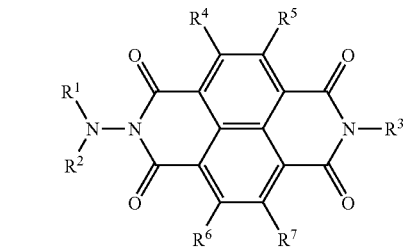

General Formula (1)

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; and $R^1$ and $R^2$ may be linked to form a substituted or non-substituted heterocyclic group including a nitrogen atom; with compounds where all of $R^1$, $R^2$ and $R^3$ are a methyl group, and compounds where both of $R^1$ and $R^2$ are a methyl group and $R^3$ is a 1-octyl group being excluded.

As described above, the present naphthalenetetracarboxylic acid diimide derivatives effectively enable photoconductors to maintain satisfactory image quality even when repeatedly used. The reason has not yet been elucidated, but the present inventors conceive that strongly basic amino moieties contained in the chemical structure electrically neutralize oxidation gas, which is considered a substance causing image blur. When used in combination with another charge transport material, the present naphthalenetetracarboxylic acid diimide derivatives exhibit higher stability to repetitive use, higher sensitivity, etc. In particular, below-described specific charge transport materials are preferably used.

The present naphthalenetetracarboxylic acid diimide derivatives exhibit electron transferrability. Single layer photoconductors which can be both positively and negatively charged may be formed from the present naphthalenetetracarboxylic acid diimide derivatives by appropriately determining the layer structure or by using a hole transport material in combination.

For the above reasons, there can be provided an electrophotographic photoconductors which attains both high durability and high image quality, which can consistently provide high-quality images even when repeatedly used, and which can be both positively and negatively charged; and an electrophotographic method, apparatus and process cartridge which can consistently provide high-quality images even when repeatedly used.

Separately, the present inventors carried out extensive studies, and have found that a naphthalenetetracarboxylic acid diimide derivatives represented by the following general formula (I) are excellent electron transport materials for use in organic electronics.

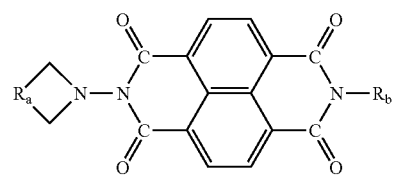

General Formula (I)

wherein $R_a$ represents a divalent group necessary for forming a nitrogen-containing ring together with a nitrogen atom and a carbon atom; a nitrogen-containing ring moiety represented by the following general formula (II) represents a substituted or non-substituted saturated or unsaturated ring which may further contain a nitrogen atom or an oxygen atom; when the nitrogen-containing ring moiety is a ring having a plurality of substituents, the substituents may form a condensed ring together with a part of the nitrogen-containing ring; and $R_b$ represents an amino-substituted or non-substituted branched alkyl group or an amino-substituted or non-substituted branched alkoxyalkyl group.

General Formula (II)

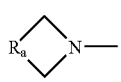

Next will be described in detail novel naphthalenetetracarboxylic acid diimide derivatives represented by the above general formula (1) or (I), electrophotographic photoconductors containing the derivatives, and an electrophotographic method, apparatus and process cartridge having the photoconductor.

<Novel Naphthalenetetracarboxylic Acid Diimide Derivative Represented by General Formula (1)>

Novel naphthalenetetracarboxylic acid diimide derivatives, which are represented by general formula (1), contained in a photoconductive layer in the present invention will be described in detail.

General Formula (1)

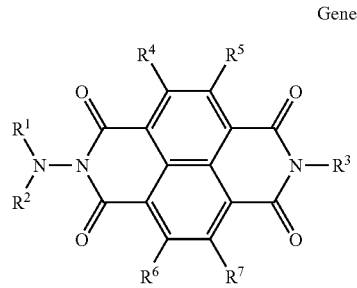

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; and $R^1$ and $R^2$ may be linked to form a substituted or non-substituted heterocyclic group including a nitrogen atom; with compounds where all of $R^1$, $R^2$ and $R^3$ are a methyl group, and compounds where both of $R^1$ and $R^2$ are a methyl group and $R^3$ is a 1-octyl group being excluded.

The naphthalenetetracarboxylic acid diimide derivatives represented by general formula (1) are synthesized following the reaction scheme 1 or 2 (given below) described in, for example, JP-A No. 2001-265031 or J. Am. Chem. Soc., 120, 3231 (1998). Specifically, a naphthalene-1,4,5,8-tetracarboxylic dianhydride derivative is simultaneously or sequentially reacted with 1,1-disubstituted hydrazine and a substituted amine derivative in the presence or absence of a solvent, to thereby produce a naphthalenetetracarboxylic acid diimide derivative represented by general formula (1).

The solvent is not particularly limited and can be appropriately selected depending on the purpose. Examples thereof include benzene, toluene, xylene, chloronaphthalene, chlorobenzene, acetic acid, pyridine, methylpyridine, picoline, N,N-dimethylformamide, N,N-dimethylacetamide, dimethylethyleneurea and dimethylsulfoxide. The reaction temperature is preferably room temperature to 250° C. The pH of the reaction mixture may be adjusted by, for example, a buffer for promoting reaction. The buffer may be prepared by mixing an acid (e.g., phosphoric acid) with an aqueous solution of a base (e.g., lithium hydroxide, potassium hydroxide or sodium hydroxide).

More specifically, as shown in scheme 1, a naphthalenetetracarboxylic acid diimide derivative represented by general formula (1) can be produced through a process including a first step in which a naphthalene-1,4,5,8-tetracarboxylic dianhydride derivative is reacted with 1,1-disubstituted hydrazine, to thereby produce a monoimide compound; and a second step in which the monoimide compound is reacted with a substituted amine derivative.

Scheem 1

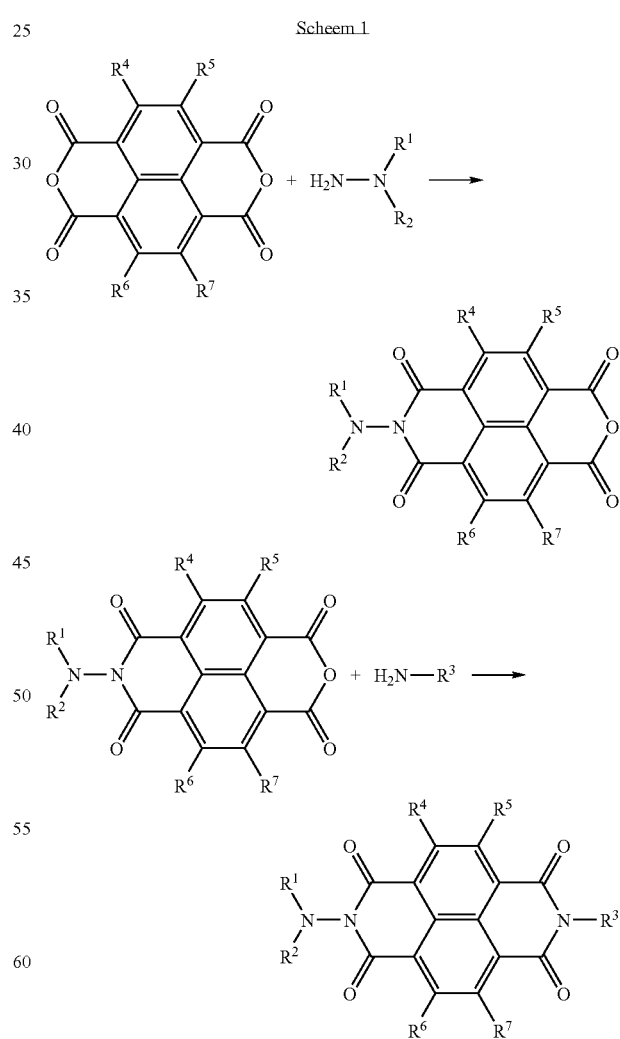

Alternatively, as shown in scheme 2, a naphthalenetetracarboxylic acid diimide derivative represented by general formula (1) can be produced through a process including a first step in which a naphthalene-1,4,5,8-tetracarboxylic dianhydride derivative is reacted with a substituted amine derivative, to thereby produce a monoimide compound; and a second step in which the monoimide compound is reacted with 1,1-disubstituted hydrazine.

Scheem 2

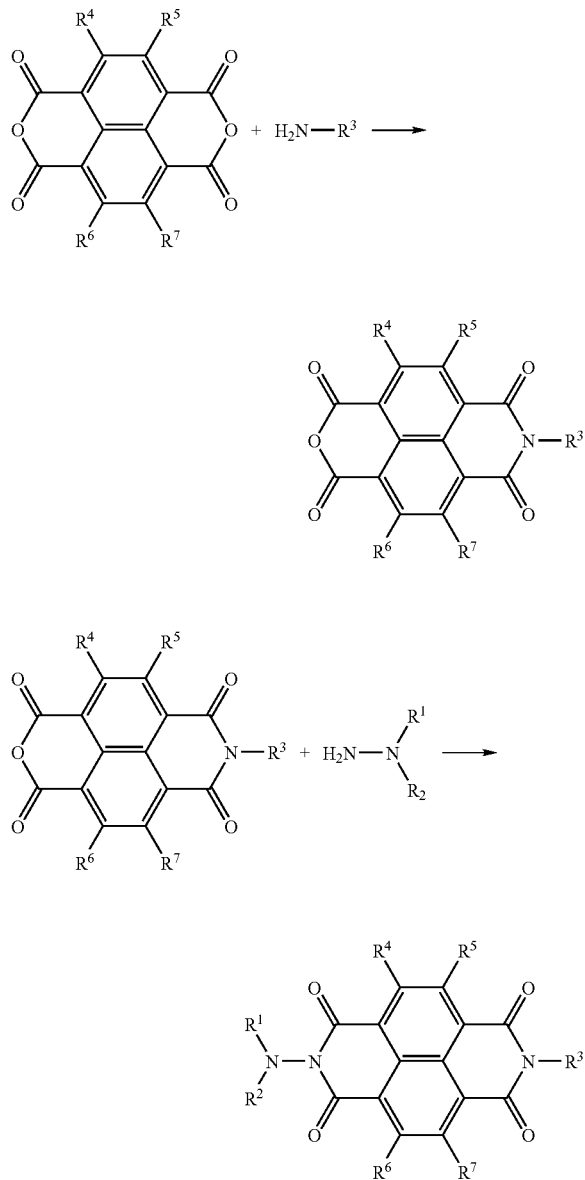

The alkyl group represented by $R^1$ or $R^2$ in general formula (1) is not particularly limited and can be appropriately selected depending on the purpose. Examples include linear or branched alkyl groups having 1 to 15 carbon atoms, with a methyl group, ethyl group, propyl group, isopropyl group, isobutyl group, sec-butyl group, tert-butyl group, 2-pentyl group, 3-pentyl group, 2-heptyl group, 3-heptyl group, 4-heptyl group and sec-octyl group being preferred. The aromatic hydrocarbon group represented by $R^1$ or $R^2$ is not particularly limited and can be appropriately selected depending on the purpose. Examples include aromatic ring groups such as benzene, biphenyl, naphthalene, anthracene, fluorene and pyrene; and aromatic heterocyclic groups such as pyridine, quinoline, thiophene, furan, oxazole, oxadiazole and carbazole. The alkyl group having 1 to 8 carbon atoms represented by $R^3$ is not particularly limited and can be appropriately selected depending on the purpose. Examples include an ethyl group, propyl group, isopropyl group, 1,2-dimethylpropyl group, isobutyl group, sec-butyl group, tert-butyl group, 2-pentyl group, 3-pentyl group, hexyl group, 2-heptyl group, 3-heptyl group, 4-heptyl group and undecanyl group. The aromatic hydrocarbon group represented by $R^3$ is not particularly limited and can be appropriately selected depending on the purpose. Examples include aromatic ring groups such as benzene, biphenyl, naphthalene, anthracene, fluorene and pyrene; and aromatic heterocyclic groups such as pyridine, quinoline, thiophene, furan, oxazole, oxadiazole and carbazole.

The substituent which the group represented by $R^1$ or $R^2$ may have is not particularly limited and can be appropriately selected depending on the purpose. Examples include alkyl groups described above; alkoxy groups such as a methoxy group, ethoxy group, propoxy group and butoxy group; halogen atoms such as a fluorine atom, chlorine atom, bromine atom and iodine atom; dialkylamino groups; a diphenylamino group; aromatic hydrocarbon groups described above; and heterocyclic groups such as pyrrolidine, piperidine and piperazine.

$R^1$ and $R^2$ may be linked to form a heterocyclic group including a nitrogen atom. The heterocyclic group is not particularly limited and can be appropriately selected depending on the purpose. Examples include condensed heterocyclic groups formed by condensation of aromatic hydrocarbon groups with a pyrrolidino group, a piperidino group, a piperazino group and the like.

Preferred compounds represented by general formula (1) (Compound (Derivative) Nos. 1 to 48 used in Examples 23 to 82 given below) will be listed below, which should not be construed as limiting the present invention thereto.

1

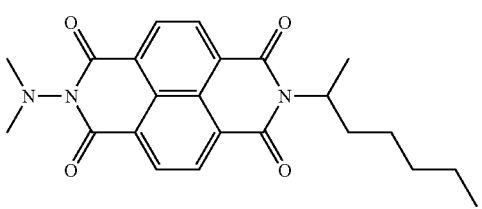

m.p. 166.0° C.-167.0° C.

-continued
2 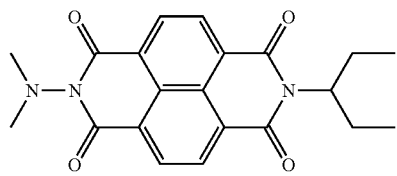
m.p. 207.5° C.-208.5° C.
3 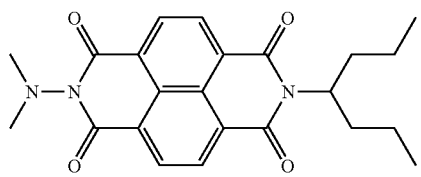
m.p. 148.0° C.-149.0° C.
4 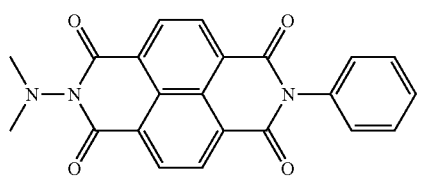
5 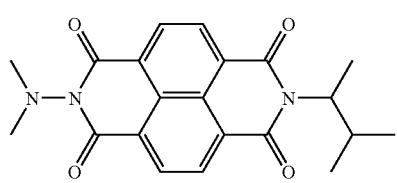
6 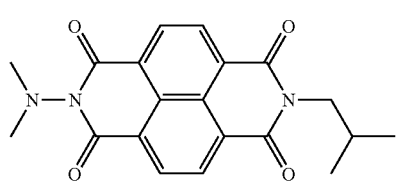
7 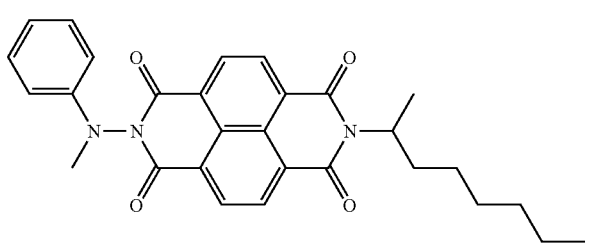
8 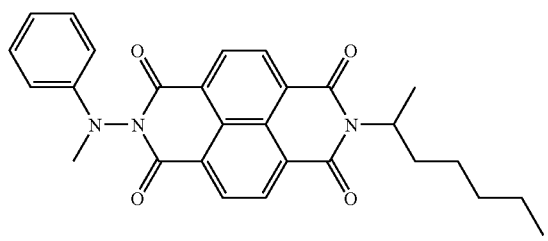
m.p. 211.5° C.-212.0° C.

-continued
9
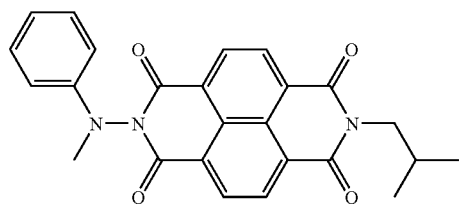
10
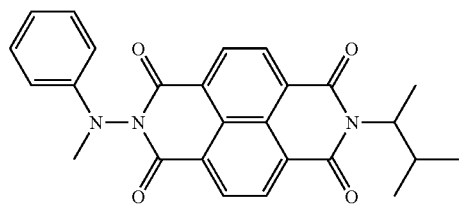
11
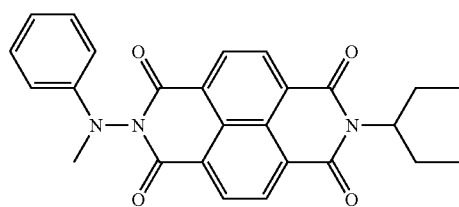
12
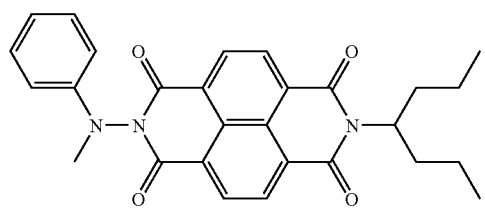
m.p. 162.0° C.-164.0° C.
13
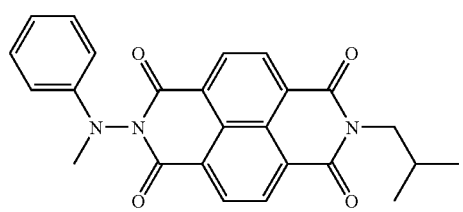
14
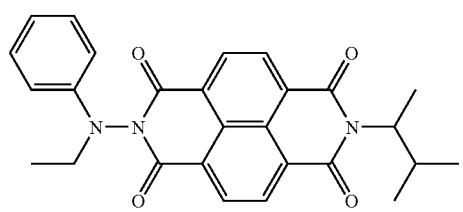
15
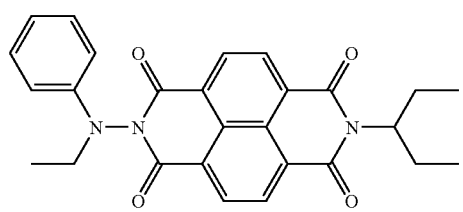
m.p. 203.5° C.-204.5° C.

-continued
16
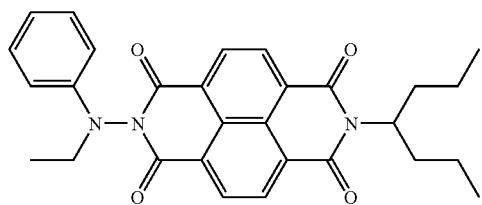
m.p. 159.0° C.-161.0° C.
17
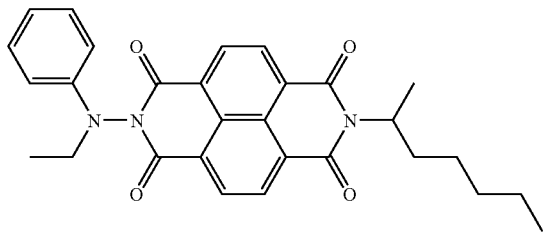
m.p. 130.5° C.-131.5° C.
18
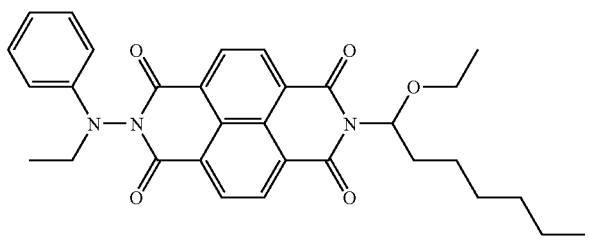
19
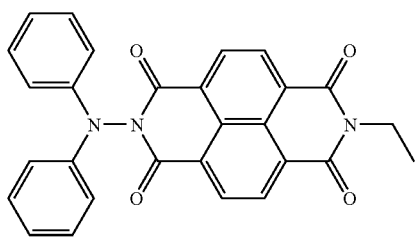
20
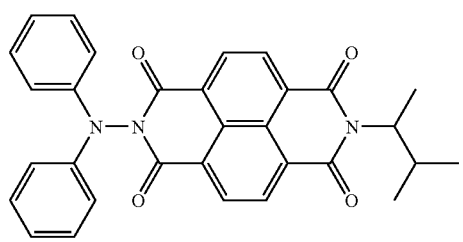
amorphous crystals
21
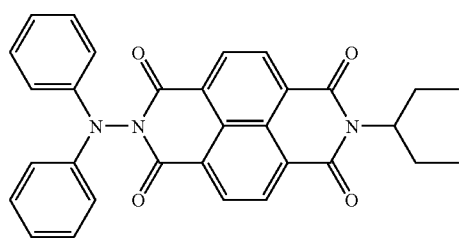
m.p. 197.0° C.-198.0° C.

-continued
22
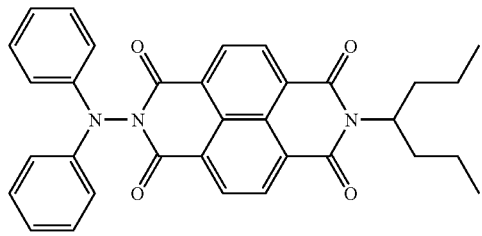
amorphous crystals
23
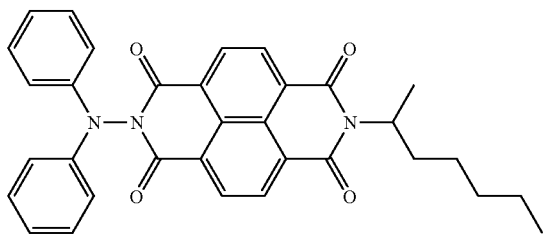
amorphous crystals
24
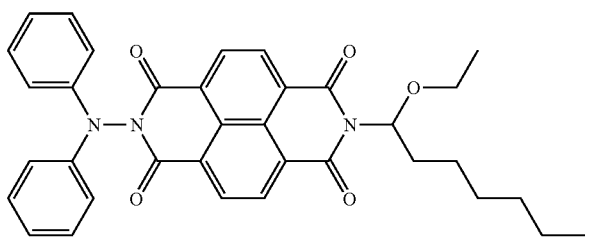
25
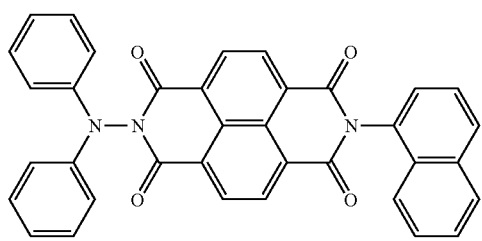
26
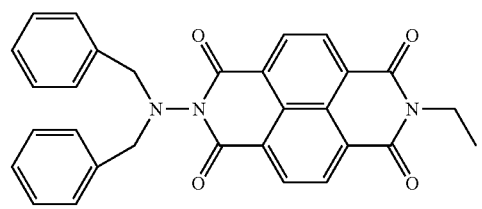
27
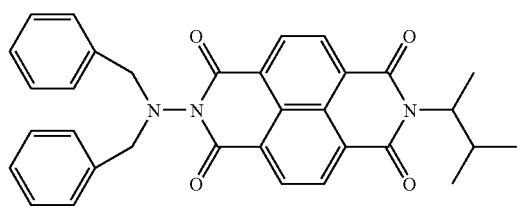

| | |
|---|---|
| 28 | 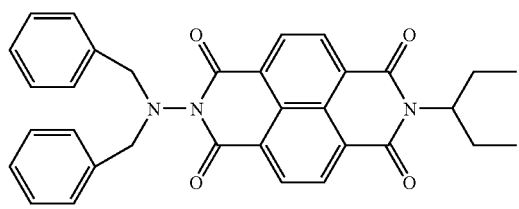 |
| 29 | 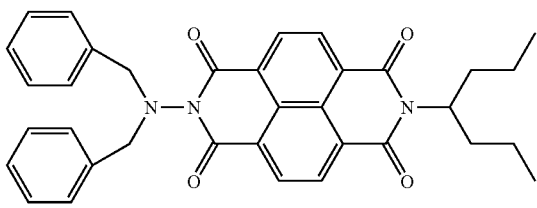
m.p. 195.5° C.-196.5° C. |
| 30 | 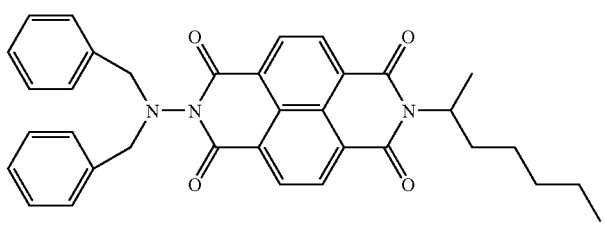
m.p. 147.0° C.-148.0° C. |
| 31 | 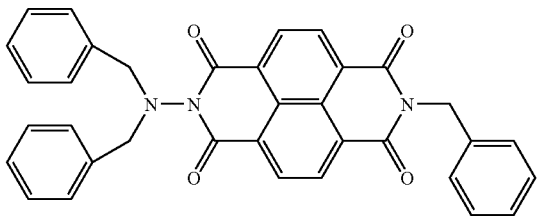 |
| 32 | 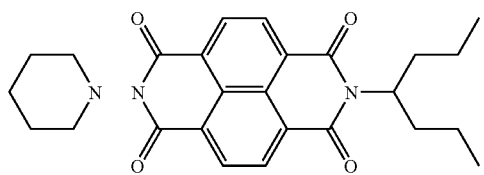 |
| 33 | 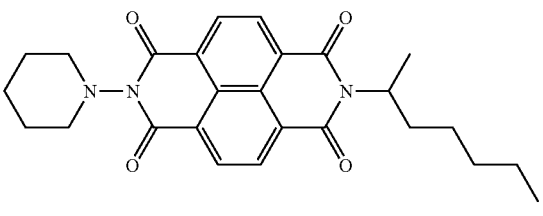
m.p. 184.5° C.-185.5° C. |
| 34 | 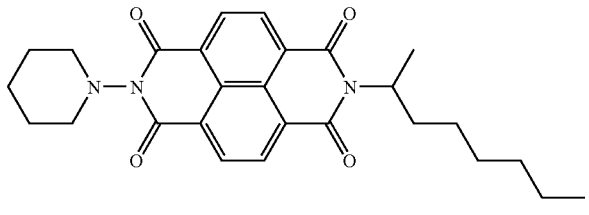
m.p. 187.5° C.-188.0° C. |

-continued
| | | |
|---|---|---|
| 35 | 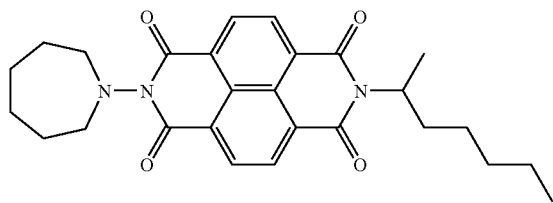 m.p. 132.0° C.-133.0° C. | |
| 36 | 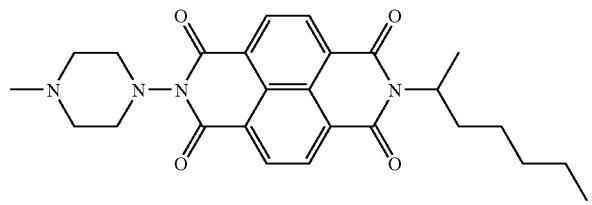 m.p. 210.0° C.-210.5° C. | |
| 37 | 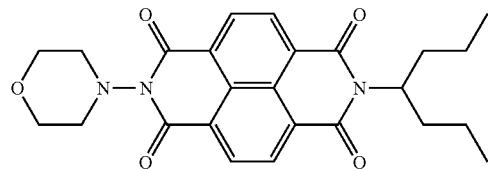 | |
| 38 | 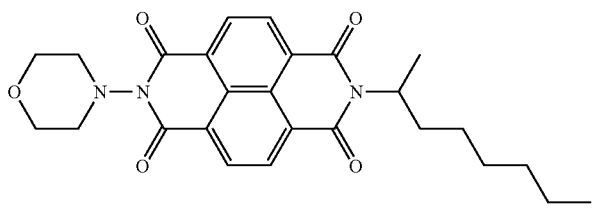 m.p. 198.5° C.-200.0° C. | |
| 39 | 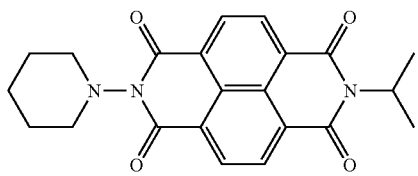 | |
| 40 | 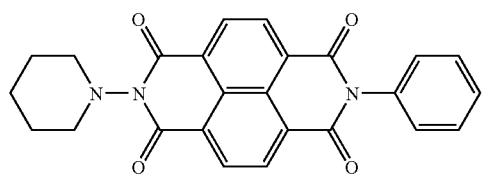 | |
| 41 | 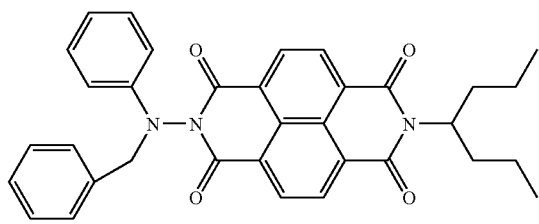 m.p. 131.0° C.-133.0° C. | |

42 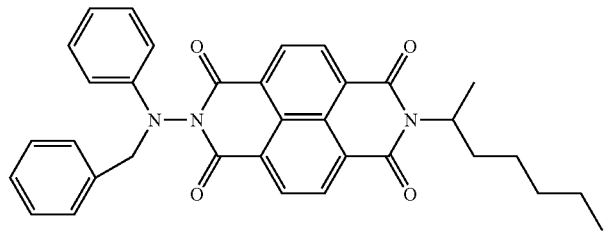
43 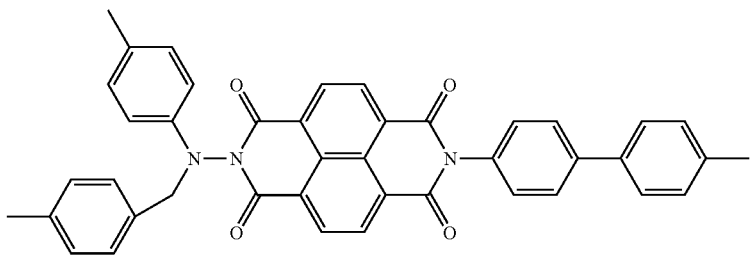
44 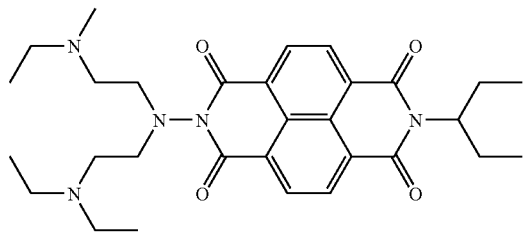
45 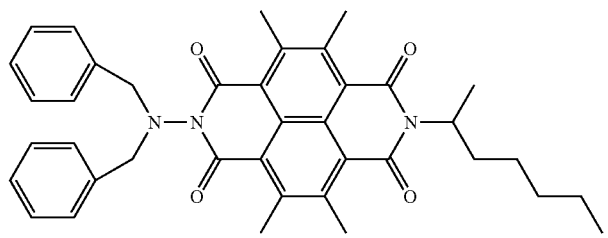
46 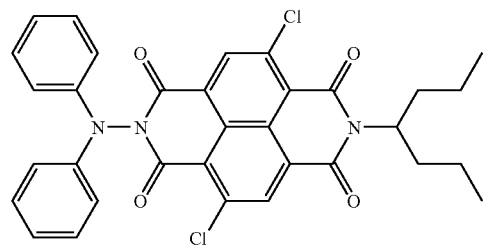
47 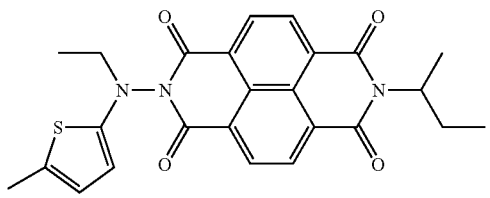

48 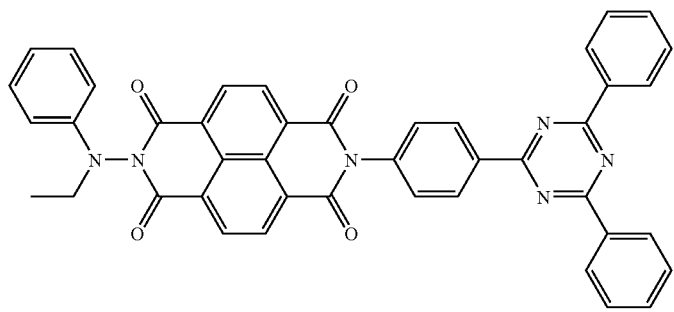

<Naphthalenetetracarboxylic Acid Diimide Derivative Represented by General Formula (I)>

Preferred naphthalenetetracarboxylic acid diimide derivatives of the present invention represented by general formula (I) will be listed below, which should not be construed as limiting the present invention thereto.

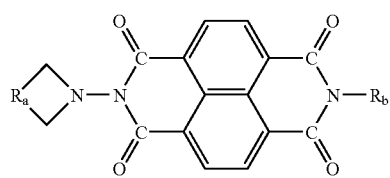

General Formula (I)

TABLE 1

| No. | $R_a$ (azetidine N—) | $R_b$ |
|---|---|---|
| 1 | piperidine-N— | —CH(CH₃)CH₂CH₂CH₂CH₃ |
| 2 | piperidine-N— | —CH(CH₃)CH₂CH₂CH₂CH₂CH₂CH₃ |
| 3 | piperidine-N— | —CH(CH₂CH₃)CH₂CH₃ |
| 4 | piperidine-N— | —CH(CH₂CH₂CH₃)CH₂CH₂CH₃ |
| 5 | piperidine-N— | —CH₂CH(CH₂CH₃)CH₂CH₂CH₂CH₃ |

TABLE 1-continued

| No. | $R_a$ (azetidine N—) | $R_b$ |
|---|---|---|
| 6 | piperidine-N— | —CH(CH₃)CH₂CH₂CH₂CH(CH₃)CH₃ |
| 7 | piperidine-N— | —CH(CH₃)CH₂CH₂CH₂N(CH₃)CH₃ |
| 8 | piperidine-N— | —CH₂CH₂CH₂OCH₂CH(CH₂CH₃)CH₂CH₂CH₂CH₃ |
| 9 | pyrrolidine-N— | —CH(CH₂CH₂CH₃)CH₂CH₂CH₃ |
| 10 | pyrrolidine-N— | —CH(CH₃)CH₂CH₂CH₂CH(CH₃)CH₃ |

TABLE 2

| No. | $R_a$ (azetidine N—) | $R_b$ |
|---|---|---|
| 11 | pyrrolidine-N— | —CH(CH₃)CH₂CH₂CH₂CH₂CH₃ |
| 12 | pyrrolidine-N— | —CH(CH₃)CH₂CH₂CH₂CH₂CH₂CH₃ |

TABLE 2-continued

| No. | ![Ra-N ring] | $R_b$ |
|---|---|---|
| 13 | pyrrolidin-1-yl | $-CH(CH_2CH_3)_2$ |
| 14 | 2,6-dimethylpiperidin-1-yl | $-CH(CH_3)CH_2CH_2CH_2CH_3$ |
| 15 | 2,6-dimethylpiperidin-1-yl | $-CH_2CH(CH_2CH_3)CH_2CH_2CH_3$ |
| 16 | 2,6-dimethylpiperidin-1-yl | $-CH(CH_3)CH_2CH_2CH_2CH_2CH_3$ |
| 17 | 2,6-dimethylpiperidin-1-yl | $-CH(CH_2CH_3)_2$ |
| 18 | 2,6-dimethylpiperidin-1-yl | $-CH_2CH_2CH_2OCH_2CH(CH_2CH_3)CH_2CH_2CH_3$ |
| 19 | azepan-1-yl | $-CH_2CH(CH_2CH_3)CH_2CH_2CH_3$ |
| 20 | azepan-1-yl | $-CH(CH_3)CH_2CH_2N(CH_3)_2$ |

TABLE 3

| No. | ![Ra-N ring] | $R_b$ |
|---|---|---|
| 21 | azepan-1-yl | $-CH(CH_3)CH_2CH_2CH_2CH_2CH_3$ |
| 22 | azepan-1-yl | $-CH(CH_3)CH_2CH_2CH_2CH_2CH_2CH_3$ |
| 23 | azepan-1-yl | $-CH(CH_2CH_3)_2$ |
| 24 | azepan-1-yl | $-CH(CH_2CH_2CH_3)_2$ |
| 25 | 4-methylpiperazin-1-yl | $-CH_2CH(CH_2CH_3)CH_2CH_2CH_2CH_3$ |

TABLE 3-continued

| No. | R_a–N— (azetidine) | R_b |
|---|---|---|
| 26 | CH₃–N(piperazine)N– | –CH(CH₃)CH₂CH₂CH₂CH(CH₃)CH₃ |
| 27 | CH₃–N(piperazine)N– | –CH(CH₃)CH₂CH₂CH₂N(CH₃)CH₃ |
| 28 | CH₃–N(piperazine)N– | –CH₂CH₂CH₂OCH₂CH(CH₂CH₃)(CH₂CH₂CH₃) |
| 29 | CH₃–N(piperazine)N– | –CH(CH₃)CH₂CH₂CH₂CH₃ |
| 30 | CH₃–N(piperazine)N– | –CH(CH₃)CH₂CH₂CH₂CH₂CH₃ |

TABLE 4

| No. | R_a–N— (azetidine) | R_b |
|---|---|---|
| 31 | HOCH₂CH₂–N(piperazine)N– | –CH(CH₃)CH₂CH₂CH₂CH₃ |
| 32 | HOCH₂CH₂–N(piperazine)N– | –CH(CH₃)CH₂CH₂CH₂CH₂CH₃ |
| 33 | HOCH₂CH₂–N(piperazine)N– | –CH(CH₂CH₃)CH₂CH₃ |
| 34 | HOCH₂CH₂–N(piperazine)N– | –CH(CH₂CH₂CH₃)CH₂CH₂CH₃ |
| 35 | HOCH₂CH₂–N(piperazine)N– | –CH₂CH(CH₂CH₃)CH₂CH₂CH₂CH₃ |

TABLE 4-continued

| No. | ![Ra-N-]  | $R_b$ |
|---|---|---|
| 36 | HOCH₂CH₂—N(piperazine)N— | —CH(CH₃)CH₂CH₂CH₂CHCH₃(CH₃) |
| 37 | (tetrahydroquinoline)N— | —CH(CH₃)CH₂CH₂CH₂NCH₃(CH₃) |
| 38 | (tetrahydroquinoline)N— | —CH₂CH₂CH₂OCH₂CH(CH₂CH₃)(CH₂CH₂CH₃) |
| 39 | (tetrahydroquinoline)N— | —CH(CH₃)CH₂CH₂CH₂CH₃ |
| 40 | (tetrahydroquinoline)N— | —CH(CH₃)CH₂CH₂CH₂CH₂CH₃ |

TABLE 5

| No. | ![Ra-N-] | $R_b$ |
|---|---|---|
| 41 | (morpholine)N— | —CH(CH₃)CH₂CH₂CH₂CH₂CH₃ |
| 42 | (morpholine)N— | —CH(CH₃)CH₂CH₂CH₂CH₂CH₃ |
| 43 | (morpholine)N— | —CH(CH₂CH₃)(CH₂CH₃) |
| 44 | (morpholine)N— | —CH(CH₂CH₂CH₃)(CH₂CH₂CH₃) |
| 45 | (morpholine)N— | —CH₂CH(CH₂CH₃)(CH₂CH₂CH₂CH₃) |
| 46 | (morpholine)N— | —CH(CH₃)CH₂CH₂CH₂CHCH₃(CH₃) |
| 47 | (morpholine)N— | —CH(CH₃)CH₂CH₂CH₂NCH₃(CH₃) |

TABLE 5-continued

| No. | ![structure with Ra-N] | Rb |
|---|---|---|
| 48 | morpholine-N— | —CH₂CH₂CH₂OCH(CH₂CH₃)(CH₂CH₂CH₂CH₃) |

The compounds represented by general formula (I) are synthesized following the reaction scheme 3 or 4 (given below) described in, for example, JP-A No. 2001-265031 or J. Am. Chem. Soc., 120, 3231 (1998). Specifically, the compounds may be produced by a method in which naphthalenetetracarboxylic acid or an anhydride thereof is reacted with a substituted or non-substituted branched alkylamine, to thereby produce a monoimide compound, followed by reaction of the monoimide compound with a hydrazine derivative having a ring structure; or a method in which naphthalenetetracarboxylic acid or an anhydride thereof is reacted with a hydrazine derivative having a ring structure, followed by reaction of the resultant compound with a substituted or non-substituted branched alkylamine.

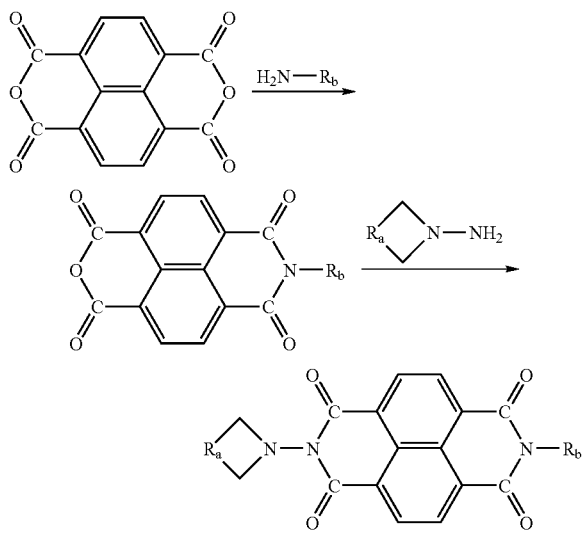

Scheem 3

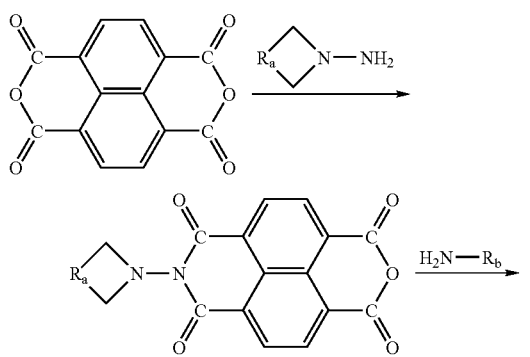

Scheem 4

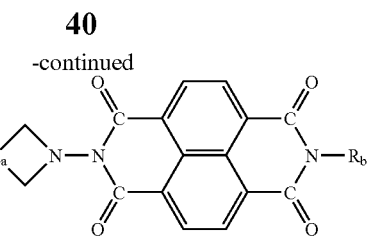

The reactions shown in the schemes 3 and 4 are carried out in the presence or absence of a solvent. The solvent is not particularly limited and can be appropriately selected depending on the purpose. Examples include N,N-dimethylformamide, N,N-dimethylacetamide, dimethylsulfoxide, pyridine, picoline, acetic acid, chloronaphthalene, chlorobenzene, xylene and toluene. If necessary, a catalyst may be used in the reaction. The catalyst is not particularly limited and can be appropriately selected depending on the purpose. Examples include benzenesulfonic acid, p-toluenesulfonic acid and acetic acid.

The hydrazine derivative having a ring structure is not particularly limited and can be appropriately selected depending on the purpose. Preferred are a substituted or non-substituted 1-aminopyrrolidine, a substituted or non-substituted 1-aminopiperidine, a substituted or non-substituted 1-aminohomopiperidine, a substituted or non-substituted 1-aminopiperazine and a substituted or non-substituted N-aminomorpholine. The substituent which the above substituted groups have is not particularly limited and can be appropriately selected depending on the purpose. Examples include alkyl groups having 1 to 5 carbon atoms, alkyl groups having a hydroxyl group as a substituent, and halogen atoms such as chlorine.

The substituted or non-substituted branched alkylamine is not particularly limited and can be appropriately selected depending on the purpose. The alkylamine preferably has an alkyl group having 4 to 15 carbon atoms, and examples include a dimethylpropyl group, ethylpropyl group, diethylpropyl group, methylbutyl group, dimethylbutyl group, methylpentyl group, dimethylpentyl group, methylhexyl group, dimethylhexyl group, alkoxyalkyl group and dialkylaminoalkyl group.

The present naphthalenetetracarboxylic acid diimide derivatives serve as organic photoconductor materials, in particular, electron transport materials, and are used in various electrophotographic photoconductors in the following forms:
1) a single-layer photoconductor in which a mixture of a charge generation material, the naphthalenetetracarboxylic acid diimide derivative and a binder resin is coated on a conductive support;
2) a single-layer photoconductor in which a mixture of a charge generation material, a hole transport material, the naphthalenetetracarboxylic acid diimide derivative and a binder resin is coated on a conductive support;
3) a multi-layer photoconductor having a conductive support, a charge generation layer, and a charge transport layer predominantly containing the naphthalenetetracarboxylic acid derivative and a binder resin, wherein the charge generation layer is provided on the conductive support, and the charge transport layer is provided on the charge generation layer; and
4) a multi-layer photoconductor having a conductive support, a charge generation layer, and a charge transport layer predominantly containing the naphthalenetetracarboxylic acid derivative and a binder resin, wherein the charge transport layer is provided on the conductive support, and the charge generation layer is provided on the charge transport layer.

In addition, the present naphthalenetetracarboxylic acid diimide derivatives exhibit excellent electron transferrability and thus, are advantageously used as materials for use in organic electronics; e.g., photoelectric transducers, thin-layer transistors or light-emitting devices.

(Electrophotographic Photoconductor)

Next will be described the layer structure of the present electrophotographic photoconductor.

FIG. 1 is a cross-sectional view of a first electrophotographic photoconductor of the present invention. The electrophotographic photoconductor shown in FIG. 1 has a conductive support 31 and a photoconductive layer 33 predominantly containing a charge generation material and a charge transport material, wherein the photoconductive layer 33 is provided on the conductive support 31.

Figure 2:
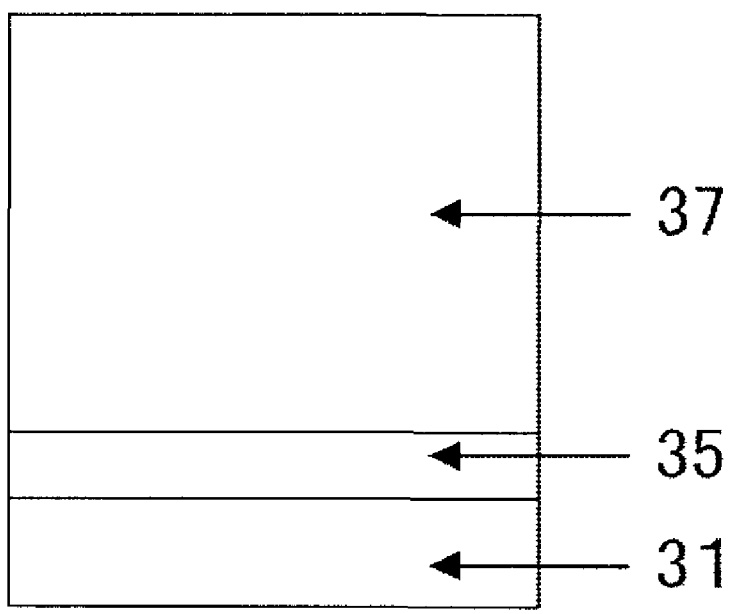
FIG. 2 is a cross-sectional view of a second electrophotographic photoconductor of the present invention.

FIG. 2 is a cross-sectional view of a second electrophotographic photoconductor of the present invention. The electrophotographic photoconductor shown in FIG. 2 has a conductive support 31, a charge generation layer 35 predominantly containing a charge generation material, and a charge transport layer 37 predominantly containing a charge transport material, wherein the charge transport layer 37 is provided on the conductive support 31, and the charge generation layer 35 is provided on the charge transport layer 37.

Figure 3:
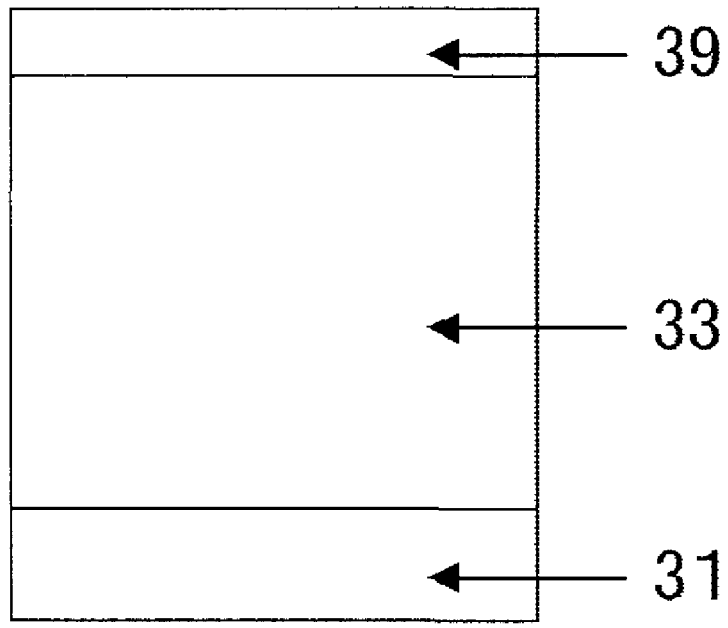
FIG. 3 is a cross-sectional view of a third electrophotographic photoconductor of the present invention.

FIG. 3 is a cross-sectional view of a third electrophotographic photoconductor of the present invention. The electrophotographic photoconductor shown in FIG. 3 has a conductive support 31, a photoconductive layer 33 predominantly containing a charge generation material and a charge transport material, and a protective layer 39, wherein the photoconductive layer 33 is provided on the conductive support 31, and the protective layer 39 is provided on the surface of the photoconductive layer 33. In this electrophotographic photoconductor, the protective layer 39 may contain the present naphthalenetetracarboxylic acid diimide derivative.

Figure 4:
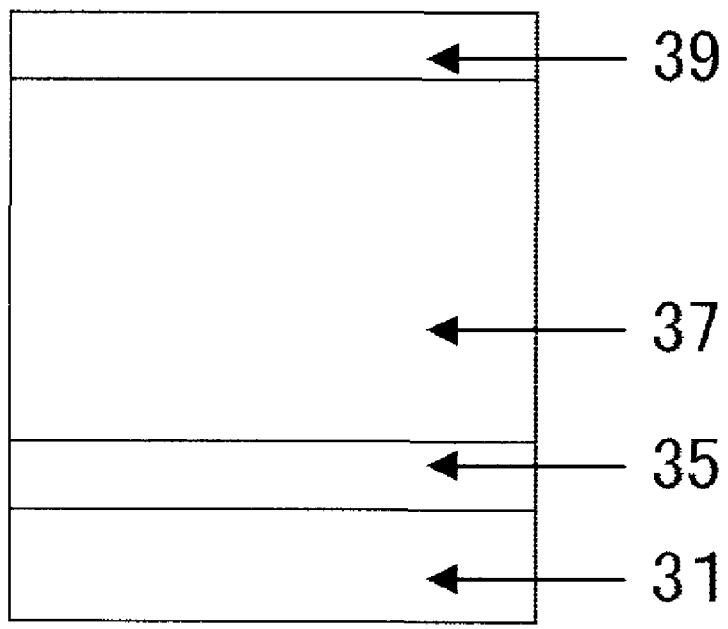
FIG. 4 is a cross-sectional view of a fourth electrophotographic photoconductor of the present invention.

FIG. 4 is a cross-sectional view of a fourth electrophotographic photoconductor of the present invention. The electrophotographic photoconductor shown in FIG. 4 has a conductive support 31, a charge generation layer 35 predominantly containing a charge generation material, a charge transport layer 37 predominantly containing a charge transport material, and a protective layer 39, wherein the charge generation layer 35 is provided on the conductive support 31, the charge transport layer 37 is provided on the charge generation layer 35, and the protective layer 39 is provided on the charge transport layer 37. In this electrophotographic photoconductor, the protective layer 39 may contain the present naphthalenetetracarboxylic acid diimide derivative.

Figure 5:
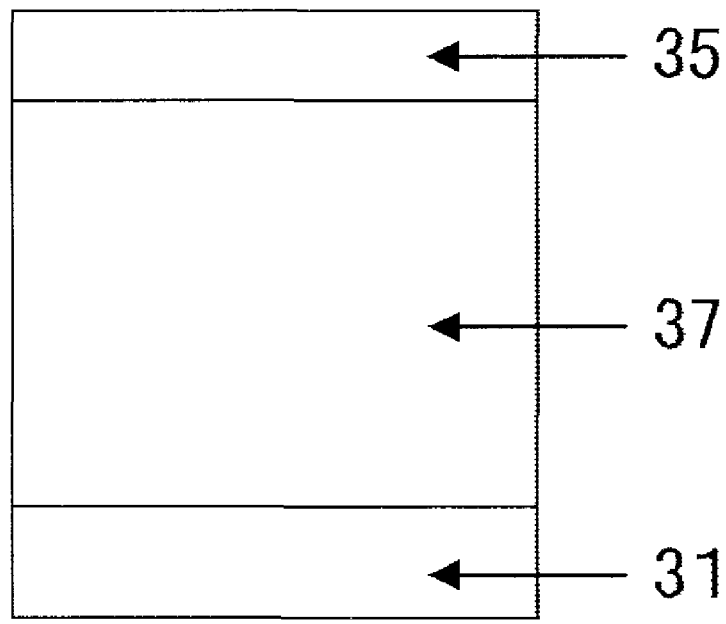
FIG. 5 is a cross-sectional view of a fifth electrophotographic photoconductor of the present invention.

FIG. 5 is a cross-sectional view of a fifth electrophotographic photoconductor of the present invention. The electrophotographic photoconductor shown in FIG. 5 has a conductive support 31, a charge transport layer 37 predominantly containing a charge transport material, and a charge generation layer 35 predominantly containing a charge generation material, wherein the charge transport layer 37 is provided on the conductive support 31, and the charge generation layer 35 is provide on the charge transport layer 37.

Figure 6:
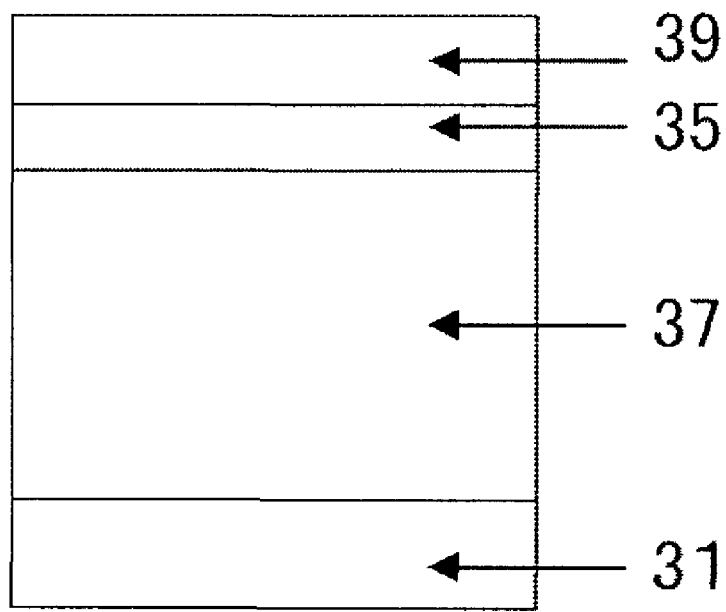
FIG. 6 is a cross-sectional view of a sixth electrophotographic photoconductor of the present invention.

FIG. 6 is a cross-sectional view of a sixth electrophotographic photoconductor of the present invention. The electrophotographic photoconductor shown in FIG. 6 has a conductive support 31, a charge transport layer 37 predominantly containing a charge transport material, a charge generation layer 35 predominantly containing a charge generation material and a protective layer 39, wherein the charge transport layer 37 is provided on the conductive support 31, the charge generation layer 35 is provided on the charge transport layer 37, and the protective layer 39 is provided on the charge generation layer 35. In this electrophotographic photoconductor, the protective layer 39 may contain the present naphthalenetetracarboxylic acid diimide derivative.

<Conductive Support>

The conductive support 31 is not particularly limited, so long as it exhibits a volume resistivity of $10^{10}\Omega\cdot cm$ or less, and can be appropriately selected depending on the purpose. Examples thereof include deposited products formed by depositing, on film-form or cylindrical plastic or paper, a metal (e.g., aluminum, nickel, chromium, nichrome, copper, gold, silver or platinum) or a metal oxide (e.g., tin oxide or indium oxide) by vapor deposition or sputtering; and also include an aluminum plate, an aluminum alloy plate, a nickel plate and a stainless steel plate. Furthermore, there may be used tubes produced as follows: the above metal plates are formed into a raw tube through extrusion, pultrusion, etc.; and the raw tube was cut and was subjected to surface treatments such as superfinishing and polishing. Also, an endless nickel belt or an endless stainless-steel belt described in JP-A No. 52-36016 may be used as the conductive support 31.

Furthermore, the conductive support 31 may be formed by coating, on the support, a dispersed mixture of conductive powder in an appropriate binder resin. The conductive powder is not particularly limited and can be appropriately selected depending on the purpose. Examples thereof include carbon black, acethylene black; powder of a metal such as aluminum, nickel, iron, nichrome, copper, zinc or silver; and powder of a metal oxide such as conductive tin oxide or ITO. The binder resin, which is used in combination with the conductive powder, is not particularly limited and can be appropriately selected depending on the purpose. Examples thereof include thermoplastic resins, thermosetting resins and photo-curable resins (e.g., polystyrene, styrene-acrylonitrile copolymers, styrene-butadiene copolymers, styrene-maleic anhydride copolymers, polyester, polyvinyl chloride, vinyl chloride-vinyl acetate copolymers, polyvinyl acetate, polyvinylidene chloride, polyarylate resins, phenoxy resins, polycarbonate, cellulose acetate resins, ethyl cellulose resins, polyvinyl butyral, polyvinyl formal, polyvinyl toluene, poly-N-vinylcarbazole, acrylic resins, silicone resins, epoxy resins, melamine resins, urethane resins, phenol resins and alkyd resins). Such a conductive layer may be formed by coating a dispersed mixture of the conductive powder and the binder resin in an appropriate solvent (e.g., tetrahydrofuran, dichloromethane, methyl ethyl ketone or toluene).

In addition, the conductive support 31 may be formed by providing an appropriate cylindrical support with, as a conductive layer, a heat-shrinkable tubing containing the conductive powder and a material (e.g., polyvinyl chloride, polypropylene, polyester, polystyrene, polyvinylidene chloride, polyethylene, chlorinated rubber or Teflon (registered trademark)).

<Photoconductive Layer>

The photoconductive layer will be described. The photoconductive layer may have a single- or multi-layer structure. For the sake of convenience, firstly will be described the photoconductive layer composed of the charge generation layer 35 and the charge transport layer 37 (i.e., multi-layer photoconductive layer).

<<Charge Generation Layer>>

The charge generation layer 35 is a layer formed predominantly of a charge generation material. The charge generation layer 35 can be made of a known charge generation material. Typical examples thereof include azo pigments such as C.I.

Pigment Blue 25 (C.I. 21180), C.I. Pigment Red 41 (C.I. 21200), C.I. Acid Red 52 (C.I. 45100), C.I. Basic Red 3 (C.I. 45210), those having a carbazole skeleton (described in JP-A No. 53-95033), those having a distyrylbenzene skeleton (described in JP-A No. 53-133445), those having a triphenylamine skeleton (described in JP-A No. 53-132347), those having a dibenzothiophene skeleton (described in JP-A No. 54-21728), those having an oxadiazole skeleton (described in JP-A No. 54-12742), those having a fluorenone skeleton (described in JP-A No. 54-22834), those having a bisstilbene skeleton (described in JP-A No. 54-17733), those having a distyryloxadiazole skeleton (described in JP-A No. 54-2129), those having a distyrylcarbazoleskeleton (described in JP-A No. 54-14967), and those having a benzanthrone skeleton; phthalocyanine pigments such as C.I. Pigment Blue 16 (C.I. 74100), Y-type oxotitanium phthalocyanine (JP-A No. 64-17066), A(β)-type oxotitanium phthalocyanine, B(α)-type oxotitanium phthalocyanine, I-type oxotitanium phthalocyanine (described in JP-A No. 11-21466), II-type chlorogallium phthalocyanine (Iijima et al., the 67th annual meeting (spring) of the Chemical Society of Japan, 1B4, 04 (1994)), V-type hydroxygallium phthalocyanine (Daimon et al., the 67th annual meeting (spring) of the Chemical Society of Japan, 1B4, 05 (1994)), and X-type metal-free phthalocyanine (U.S. Pat. No. 3,816,118); indigo pigments such as C.I. Vat Brown 5 (C.I. 73410) and C.I. Vat Dye (C.I. 73030); and perylene pigments such as Argoscarlet B (product of Bayer AG) and Intansrencescarlet R (product of Bayer AG). These materials may be alone or in combination.

The charge generation layer 35 is formed as follows: a charge generation material is dispersed, if necessary, together with a binder resin, in an appropriate solvent using a ball mill, an attritor, a sand mill, or ultrasonication; the resultant dispersed mixture (coating liquid) is coated on a conductive support; and the coated support is dried.

The binder resin, which is optionally contained in the charge generation layer 35, is not particularly limited and can be appropriately selected depending on the purpose. Examples thereof include polyamide, polyurethane, epoxy resins, polyketone, polycarbonate, silicone resins, acrylic resins, polyvinyl butyral, polyvinyl formal, polyvinyl ketone, polystyrene, polysulfone, poly-N-vinylcarbazole, polyacrylamide, polyvinyl benzal, polyester, phenoxy resins, vinyl chloride-vinyl acetate copolymers, polyvinyl acetate, polyphenyleneoxide, polyamide, polyvinyl pyridine, cellulose resins, casein, polyvinyl alcohol and polyvinyl pyrrolidone. The amount of the binder resin is 0 parts by mass to 500 parts by mass, preferably 10 parts by mass to 300 parts by mass, per 100 parts by mass of the charge generation material. Addition of the binder resin may be carried out before or after dispersion of the charge generation material.

The solvent is not particularly limited and can be appropriately selected depending on the purpose. Examples thereof include isopropanol, acetone, methyl ethyl ketone, cyclohexanone, tetrahydrofuran, dioxane, ethyl cellosolve, ethyl acetate, methyl acetate, dichloromethane, dichloroethane, monochlorobenzene, cyclohexane, toluene, xylene and ligroin, with ketone solvents, ester solvents and ether solvents being particularly preferred. These solvents may be used alone or in combination.

The charge generation layer 35 contains mainly a charge generation material, a solvent and a binder resin. Additionally, the layer may contain any additives such as a sensitizer, a dispersant, a surfactant and silicone oil.

The method for coating the coating liquid is not particularly limited and can be appropriately selected depending on the purpose. Examples thereof include immersion coating, spray coating, beat coating, nozzle coating, spinner coating and ring coating.

The thickness of the charge generation layer 35 is not particularly limited and can be appropriately selected depending on the purpose. The thickness is preferably about 0.01 μm to about 5 μm, more preferably 0.1 μm to 2 μm.

<<Charge Transport Layer>>

The charge transport layer 37 is a layer formed predominantly of a charge transport material. The charge transport material is any of a hole transport material, an electron transport material and a charge transport polymer. These materials are individually described below.

The hole transport material is not particularly limited and can be appropriately selected depending on the purpose. Examples thereof include poly-N-carbazole and derivatives thereof, poly-γ-carbazolyl ethylglutamate and derivatives thereof, pyrene-formaldehyde condensation products and derivatives thereof, polyvinyl pyrene, polyvinyl phenanthrene, oxazole derivatives, imidazole derivatives, triphenylamine derivatives, and compounds represented by the following general formulas (11) to (34):

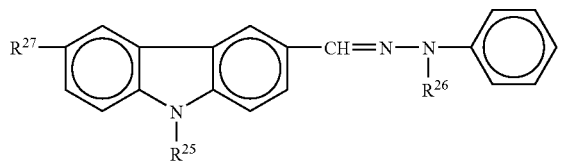

General Formula (11)

wherein $R^{25}$ represents a methyl group, ethyl group, 2-hydroxyethyl group or 2-chloroethyl group; $R^{26}$ represents a methyl group, ethyl group, benzyl group or phenyl group; and $R^{27}$ represents a hydrogen atom, chlorine atom, bromine atom, alkyl group having 1 to 4 carbon atoms, alkoxy group having 1 to 4 carbon atoms, dialkylamino group or nitro group.

Examples of compounds represented by general formula (11) include 9-ethylcarbazole-3-carbaldehyde-1-methyl-1-phenylhydrazone, 9-ethylcarbazole-3-carbaldehyde-1-benzyl-1-phenylhydrazone, and 9-ethylcarbazole-3-carbaldehyde-1,1-diphenylhydrazone.

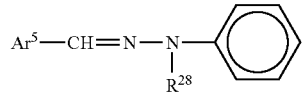

General Formula (12)

wherein $Ar^5$ represents a naphthalene ring, anthracene ring, pyrene ring, substituted naphthalene ring, substituted anthracene ring, substituted pyrene ring, pyridine ring, furan ring or thiophene ring; and $R^{28}$ represents an alkyl group, phenyl group, or benzyl group.

Examples of compounds represented by general formula (12) include 4-diethylaminostyryl-β-carbaldehyde-1-methyl-1-phenylhydrazone and 4-methoxynaphthalene-1-carbaldehyde-1-benzyl-1-phenylhydrazone.

General Formula (13)

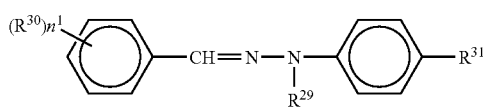

wherein $R^{29}$ represents an alkyl group, benzyl group, phenyl group or naphthyl group; $R^{30}$ represents a hydrogen atom, alkyl group having 1 to 3 carbon atoms, alkoxy group having 1 to 3 carbon atoms, dialkylamino group, diaralkylamino group or diarylamino group; $n^1$ is an integer of 1 to 4; when $n^1$ is two or more, $R^{30}$s may be identical or different; and $R^{31}$ represents a hydrogen atom or methoxy group.

Examples of compounds represented by general formula (13) include 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-(4-methoxy)phenylhydrazone, 4-diphenylaminobenzaldehyde-1-benzyl-1-phenylhydrazone, and 4-dibenzylaminobenzaldehyde-1,1-diphenylhydrazone.

General Formula (14)

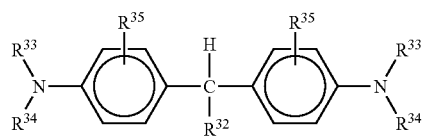

wherein $R^{32}$ represents an alkyl group having 1 to 11 carbon atoms, a substituted or non-substituted phenyl group, or a substituted or non-substituted heterocyclic group; $R^{33}$ and $R^{34}$, which may be identical or different, each represent a hydrogen atom, an alkyl group having 1 to 4 carbon atoms, a hydroxyalkyl group, a chloroalkyl group, or substituted or non-substituted aralkyl group; $R^{33}$ and $R^{34}$ may be linked to form a heterocyclic ring including a nitrogen atom; and $R^{35}$s, which may be identical or different, each represent a hydrogen atom, an alkyl group having 1 to 4 carbon atoms, an alkoxy group or a halogen atom.

Examples of compounds represented by general formula (14) include 1,1-bis(4-dibenzylaminophenyl)propane, tris(4-diethylaminophenyl)methane, 1,1-bis(4-dibenzylaminophenyl)propane, and 2,2'-dimethyl-4,4'-bis(diethylamino)-triphenylmethane.

General Formula (15)

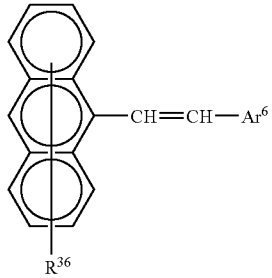

wherein $R^{36}$ represents a hydrogen atom or halogen atom; $Ar^6$ represents a substituted or non-substituted phenyl group, a substituted or non-substituted naphthyl group, a substituted or non-substituted anthryl group, or a substituted or non-substituted carbazolyl group.

Examples of compounds represented by general formula (15) include 9-(4-diethylaminostyryl)anthracene and 9-bromo-10-(4-diethylaminostyryl)anthracene.

General Formula (16)

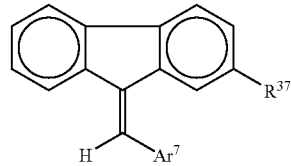

wherein $R^{37}$ represents a hydrogen atom, halogen atom, cyano group, alkoxy group having 1 to 4 carbon atoms or alkyl group having 1 to 4 carbon atoms; and $Ar^7$ represents a group represented by the following general formula (17) or (18).

General Formula (17)

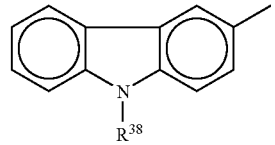

wherein $R^{38}$ represents an alkyl group having 1 to 4 carbon atoms.

General Formula (18)

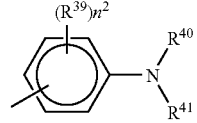

wherein $R^{39}$ represents a hydrogen atom, halogen atom, alkyl group having 1 to 4 carbon atoms, alkoxy group having 1 to 4 carbon atoms or dialkylamino group; $n^2$ is 1 or 2; when $n^2$ is 2, $R^{39}$s may be identical or different; $R^{40}$ or $R^{41}$ represents a hydrogen atom, a substituted or non-substituted alkyl group having 1 to 4 carbon atoms, or a substituted or non-substituted benzyl group.

Examples of compounds represented by general formula (16) include 9-(4-dimethylaminobenzylidene)fluorene and 3-(9-fluorenylidene)-9-ethylcarbazole.

General Formula (19)

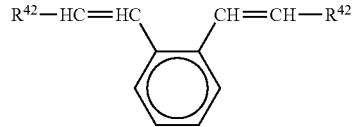

wherein $R^{42}$ represents a carbazolyl group, pyridyl group, thienyl group, indolyl group, furyl group, substituted or non-substituted phenyl group, substituted or non-substituted styryl group, substituted or non-substituted naphthyl group, or substituted or non-substituted anthryl group, wherein each substituted group has a substituent selected from the group consisting of a dialkylamino group, alkyl group, alkoxy group, carboxy group, esterified carboxy group, halogen atom, cyano group, aralkylamino group, N-alkyl-N-aralkylamino group, amino group, nitro group and acethylamino group.

Examples of compounds represented by general formula (19) include 1,2-bis(4-diethylaminostyryl)benzene and 1,2-bis(2, 4-dimethoxystyryl)benzene.

General Formula (20)

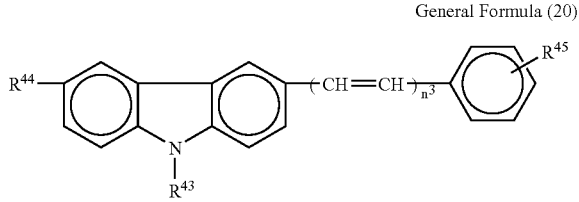

wherein $R^{43}$ represents a lower alkyl group, substituted or non-substituted phenyl group, or substituted or non-substituted benzyl group; $R^{44}$ and $R^{45}$ each represent a hydrogen atom, lower alkyl group, lower alkoxy group, halogen atom, nitro group, amino group, or amino group having as a substituent a lower alkyl group or a benzyl group; and $n^3$ is an integer of 1 or 2.

Examples of compounds represented by general formula (20) include 3-styryl-9-ethylcarbazole, 3-(4-methoxystyryl)-9-ethylcarbazole.

General Formula (21)

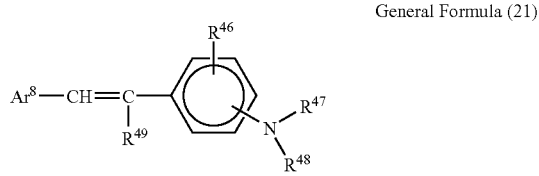

wherein $R^{46}$ represents a hydrogen atom, alkyl group, alkoxy group or halogen atom; $R^{47}$ and $R^{48}$ each represent a substituted or non-substituted aryl group; $R^{49}$ represents a hydrogen atom, lower alkyl group or substituted or non-substituted phenyl group; and $Ar^8$ represents a substituted or non-substituted phenyl group, or substituted or non-substituted naphthyl group.

Examples of compounds represented by general formula (21) include 4-diphenylaminostilbene, 4-dibenzylaminostilbene, 4-ditolylaminostilbene, 1-(4-diphenylaminostyryl)naphthalene and 1-(4-diphenylaminostyryl)naphthalene.

General Formula (22)

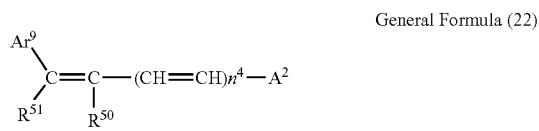

wherein $n^4$ is an integer of 0 or 1; $R^{50}$ represents a hydrogen atom, alkyl group or substituted or non-substituted phenyl group; $Ar^9$ represents a substituted or non-substituted aryl group; $R^{51}$ represents a substituted or non-substituted alkyl group or a substituted or non-substituted aryl group; $A^2$ represents a 9-anthryl group, a substituted or non-substituted carbazolyl group, or a group represented by the following general formula (23) or (24); and when $n^4$ is 0, $A^2$ and $R^{50}$ may be linked to form a ring.

General Formula (23)

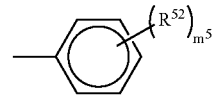

General Formula (24)

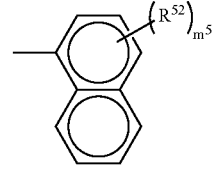

in general formulas (23) and (24), $R^{52}$ represents an alkyl group, an alkoxy group, a halogen atom, or a group represented by the following general formula (25); $m^5$ is an integer of 0 to 3; and when $m^5$ is two or more, $R^{52}$s may be identical or different.

General Formula (25)

wherein $R^{53}$ and $R^{54}$, which may be identical or different, each represent a substituted or non-substituted aryl group; and $R^{53}$ and $R^{54}$ may be linked to form a ring.

Examples of compounds represented by general formula (22) include 4'-diphenylamino-α-phenylstilbene and 4'-bis(4-methylphenyl)amino-α-phenylstilbene.

General Formula (26)

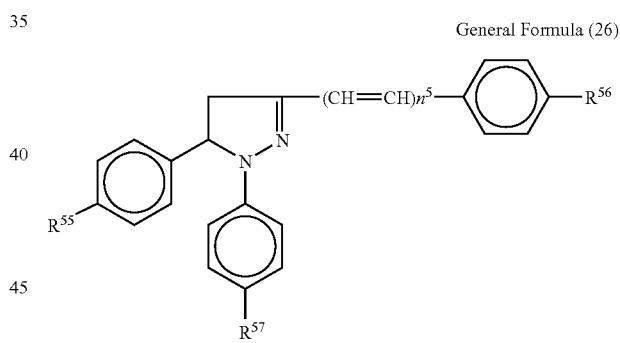

wherein $R^{55}$, $R^{56}$ and $R^{57}$ each represent a hydrogen atom, lower alkyl group, lower alkoxy group, halogen atom or dialkylamino group; and $n^5$ is 0 or 1.

Examples of compounds represented by general formula (26) include
1-phenyl-3-(4-diethylaminostyryl)-5-(4-diethylaminophenyl)pyrazoline General Formula (27)

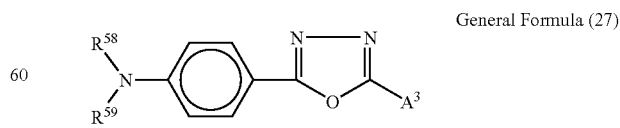

wherein $R^{58}$ and $R^{59}$ each represent a substituted or non-substituted alkyl group or a substituted or non-substituted aryl group; $A^3$ represents a substituted amino group, a substituted or non-substituted aryl group, or an allyl group.

Examples of compounds represented by general formula (27) include 2,5-bis(4-diethylaminophenyl)-1,3,4-oxadiazole, 2-N,N-diphenylamino-5-(4-diethylaminophenyl)-1,3,4-oxadiazole, and 2-(4-dimethylaminophenyl)-5-(4-diethylaminophenyl)-1,3,4-oxadiazole

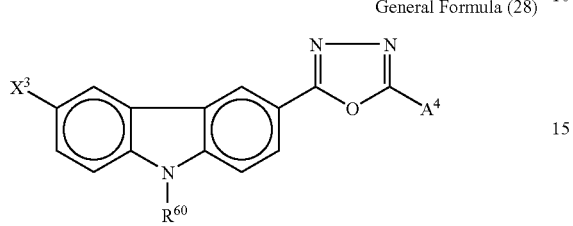

General Formula (28)

wherein $X^3$ represents a hydrogen atom, lower alkyl group or halogen atom; $R^{60}$ represents a substituted or non-substituted alkyl group or a substituted or non-substituted aryl group; and $A^4$ represents a substituted amino group or a substituted or non-substituted aryl group.

Examples of compounds represented by general formula (28) include

2-N,N-diphenylamino-5-(N-ethylcarbazol-3-yl)-1,3,4-oxadiazole and 2-(4-diethylaminophenyl)-5-(N-ethylcarbazol-3-yl)-1,3,4-oxadiazole.

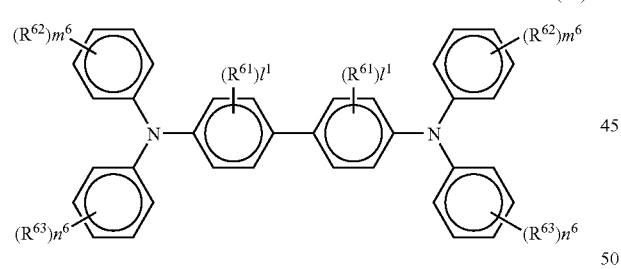

General Formula (29)

wherein $R^{61}$ represents a lower alkyl group, lower alkoxy group or halogen atom; $R^{62}$ and $R^{63}$, which may be identical or different, each represent a hydrogen atom, lower alkyl group, lower alkoxy group or halogen atom; and $l^1$, $m^6$ or $n^6$ is an integer of 0 to 4.

Examples of benzidine compounds represented by general formula (29) include

N,N'-diphenyl-N,N'-bis(3-methylphenyl)-[1,1'-biphenyl]-4,4'-diamine and 3,3'-dimethyl-N,N,N',N'-tetrakis(4-methylphenyl)-[1,1'-biphenyl]-4,4'-diamine.

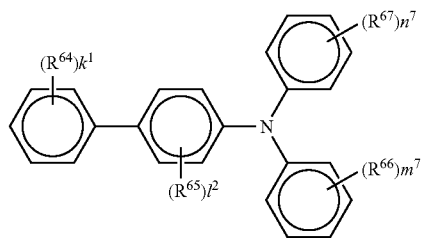

General Formula (30)

wherein $R^{64}$, $R^{66}$ and $R^{67}$ each represent a hydrogen atom, amino group, alkoxy group, thioalkoxy group, aryloxy group, methylenedioxy group, substituted or non-substituted alkyl group, halogen atom, or substituted or non-substituted aryl group; $R^{65}$ represents a hydrogen atom, alkoxy group, substituted or non-substituted alkyl group, or halogen atom; $k^1$, $l^2$, $m^7$ or $n^7$ is an integer of 1, 2, 3 or 4; and when $k^1$, $l^2$, $m^7$ or $n^7$ is an integer of 2, 3 or 4, $R^{64}$s, $R^{65}$s, $R^{66}$s or $R^{67}$s may be identical or different; with compounds where all of $R^{64}$, $R^{65}$, $R^{66}$ and $R^{67}$ are a hydrogen atom being excluded.

Examples of biphenylylamine compounds represented by general formula (30) include 4'-methoxy-N,N-diphenyl-[1,1'-biphenyl]-4-amine, 4'-methyl-N,N-bis(4-methylphenyl)-[1,1'-biphenyl]-4-amine, 4'-methoxy-N,N-bis(4-methylphenyl)-[1,1'-biphenyl]-4-amine, and N,N-bis(3,4-dimethylphenyl)-[1,1'-biphenyl]-4-amine.

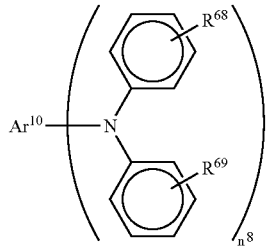

General Formula (31)

wherein $Ar^{10}$ represents a condensed polycyclic hydrocarbon group which may have a substituent and which has carbon atoms equal to or less than 18; $R^{68}$ and $R^{69}$, which may be identical or different, each represent a hydrogen atom, halogen atom, substituted or non-substituted alkyl group, alkoxy group, or substituted or non-substituted phenyl group; and $n^8$ is an integer of 1 or 2.

Examples of triarylamine compounds represented by general formula (31) include N,N-diphenyl-pyrene-1-amine, N,N-di-p-tolyl-pyrene-1-amine, N,N-di-p-tolyl-1-naphthylamine, N,N-di(p-tolyl)-1-phenanthrylamine, 9,9-dimethyl-2-(di-p-tolylamino)fluorene, N,N,N',N'-tetrakis(4-methylphenyl)-phenanthrene-9,10-diamine and N,N,N',N'-tetrakis(3-methylphenyl)-m-phenylenediamine.

General Formula (32)

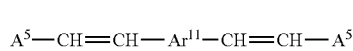

wherein $Ar^{11}$ represents a substituted or non-substituted aromatic hydrocarbon group; and $A^5$ represents a group represented by general formula (33).

General Formula (33)

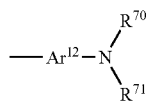

wherein $Ar^{12}$ represents a substituted or non-substituted aromatic hydrocarbon group; $R^{70}$ and $R^{71}$ each represent a substituted or non-substituted alkyl group or a substituted or non-substituted aryl group.

Examples of diolefin aromatic compounds represented by general formula (32) include 1,4-bis(4-diphenylaminostyryl)benzene and 1,4-bis[4-di(p-tolyl)aminostyryl]benzene.

General Formula (34)

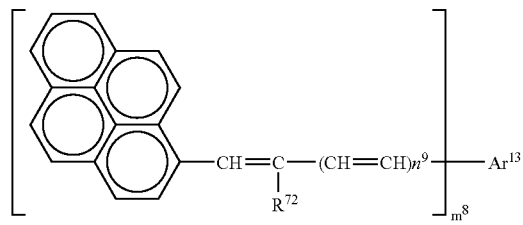

wherein $Ar^{13}$ represents a substituted or non-substituted aromatic hydrocarbon group; $R^{72}$ represents a hydrogen atom, a substituted or non-substituted alkyl group, or a substituted or non-substituted aryl group; $n^9$ is 0 or 1; $m^8$ is 1 or 2; and when $n^9$ is 0 and $m^8$ is 1, $Ar^{13}$ and $R^{72}$ may be linked to form a ring.

Examples of styrylpyrene compounds represented by general formula (34) include 1-(4-diphenylaminostyryl)pyrene and 1-(N,N-di-p-tolyl-4-aminostyryl)pyrene.

The electron transport material is not particularly limited and can be appropriately selected depending on the purpose. Examples thereof include chloranil, bromanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno-4H-indeno [1, 2-b]thiophen-4-one, and 1,3,7-trinitrodibenzothiophene-5,5-dioxide. Preferred are electron transport materials represented by the following general formula (35), (36), (37) or (38). These electron transport materials are used alone or in combination.

General Formula (35)

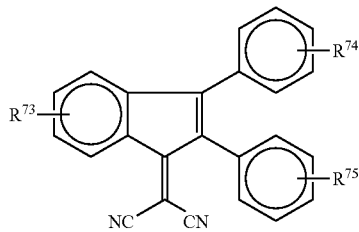

wherein $R^{73}$, $R^{74}$ and $R^{75}$, which may be identical or different, each represent a hydrogen atom, halogen atom, substituted or non-substituted alkyl group, alkoxy group, or substituted or non-substituted phenyl group.

General Formula (36)

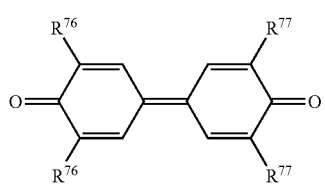

wherein $R^{76}$ and $R^{77}$, which may be identical or different, each represent a hydrogen atom, substituted or non-substituted alkyl group, substituted or non-substituted phenyl group.

General Formula (37)

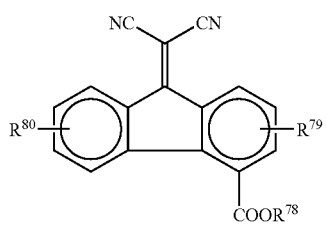

wherein $R^{78}$, $R^{79}$ and $R^{80}$, which may be identical or different, each represent a hydrogen atom, halogen atom, substituted or non-substituted alkyl group, alkoxy group, or substituted or non-substituted phenyl group.

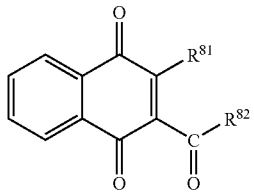

General Formula (38)

wherein $R^{81}$ represents an alkyl group which may have a substituent or an aryl group which may have a substituent; and $R^{82}$ represents an alkyl group which may have a substituent, an aryl group which may have a substituent, or a group represented by the following general formula (39).

   General Formula (39)

wherein $R^{83}$ represents an alkyl group which may have a substituent or an aryl group which may have a substituent.

The charge transport layer 37 contains, if necessary, a binder resin. The binder resin is not particularly limited and can be appropriately selected depending on the purpose. Examples thereof include thermoplastic resins and thermosetting resins such as polystyrene, styrene-acrylonitrile copolymers, styrene-butadiene copolymers, styrene-maleic anhydride copolymers, polyester, polyvinyl chloride, vinyl chloride-vinyl acetate copolymers, polyvinyl acetate, polyvinylidene chloride, polyarylate resins, phenoxy resins, polycarbonate, cellulose acetate resins, ethyl cellulose resins, polyvinyl butyral, polyvinyl formal, polyvinyl toluene, poly-N-vinylcarbazole, acrylic resins, silicone resins, epoxy resins, melamine resins, urethane resins, phenol resins and alkyd resins.

When the charge transport layer contains the charge transport material and the present naphthalenetetracarboxylic acid diimide derivative, the total content thereof is preferably 20 parts by mass to 300 parts by mass, more preferably 40 parts by mass to 150 parts by mass, per 100 parts by mass of the binder resin. The thickness of the charge transport layer is preferably 25 μm or less from the viewpoint of improving resolution and response. The lower limit of the thickness, which varies with a system employed (in particular, the charge potential of the system), is preferably 5 μm.

The amount of the present naphthalenetetracarboxylic acid diimide derivative contained in the charge transport layer is preferably 0.01 wt. % to 150 wt. % with respect to that of the charge transport material. When the amount is less than 0.01 wt. %, the charge transport layer exhibits reduced resistance to oxidation gas, whereas when the amount is more than 150 wt. %, the charge transport layer exhibits increased residual potential as a result of repetitive use.

The solvent used for forming the charge transport layer may be, for example, tetrahydrofuran, dioxane, toluene, dichloromethane, monochlorobenzene, dichloroethane, cyclohexanone, methyl ethyl ketone or acetone. The charge transport material may be used alone or in combination.

An antioxidant may be used for preventing deterioration of the present naphthalenetetracarboxylic acid diimide derivative. The antioxidant may be those generally used (listed below). In the list, (c) hydroquinones and (f) hindered amines are particularly preferred.

The antioxidant is preferably incorporated into a coating liquid prior to addition of the present naphthalenetetracarboxylic acid diimide derivative. When the antioxidant is incorporated in an amount of 0.1 wt. % to 200 wt. % with respect to that of the naphthalenetetracarboxylic acid diimide derivative, it can exhibit sufficient effects.

The charge transport layer may contain a charge transport polymer having the functions of both the charge transport material and the binder resin. Use of the charge transport polymer provides a charge transport layer exhibiting excellent wear resistance. The charge transport polymer may be known polymers. Among them, polycarbonate having a triarylamine structure in its main and/or side chain(s) is preferred, with the charge transport polymers represented by the following structural formulas (I-2) to (XIII-2) being more preferred.

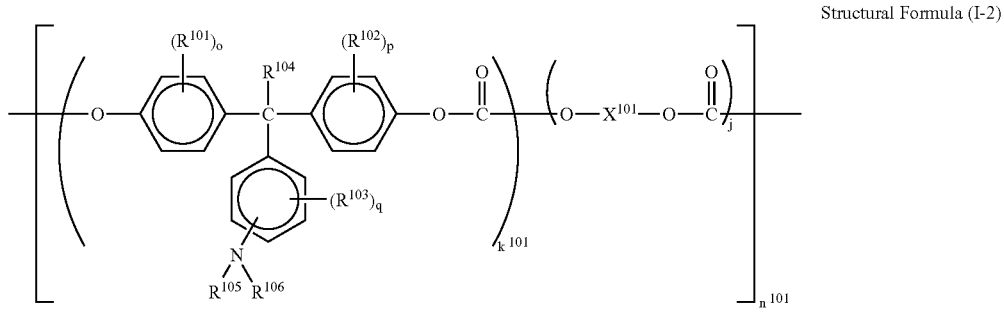

Structural Formula (I-2)

wherein $R^{101}$, $R^{102}$ and $R^{103}$ each represent a substituted or non-substituted alkyl group or a halogen atom; $R^{104}$ represents a hydrogen atom or a substituted or non-substituted alkyl group; $R^{105}$ and $R^{106}$ each represent a substituted or non-substituted aryl group; o, p or q is an integer of 0 to 4; $k^{101}$ and j satisfy the following relationships: $0.1 \leq k^{101} \leq 1$ and $0 \leq j \leq 0.9$, respectively; $n^{101}$ is the number of repeating units and is an integer of 5 to 5,000; and X101 represents a divalent aliphatic group, a divalent alicyclic group, or a divalent group represented by the following structural formula (II-2).

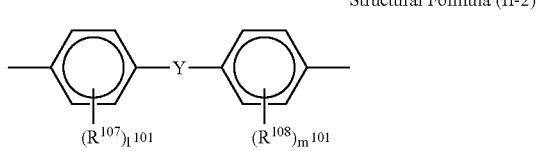

Structural Formula (II-2)

wherein $R^{107}$ and $R^{108}$ each represent a substituted or non-substituted alkyl group, aryl group or halogen atom; and $R^{107}$ and $R^{108}$ may be identical or different; $l^{101}$ or $m^{101}$ is an integer of 0 to 4; Y represents a single bond, a linear, branched or cyclic alkylene group having 1 to 12 carbon atoms, —O—, —S—, —SO—, —SO$_2$—, —CO—, —CO—O—Z—O—CO— (wherein Z represents a divalent aliphatic group), or a group represented by the following structural formula (III-2).

Structural Formula (III-2)

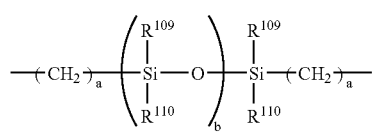

wherein a is an integer of 1 to 20; b is an integer of 1 to 2,000; $R^{109}$ and $R^{110}$ each represent a substituted or non-substituted alkyl group or an aryl group; and $R^{109}$ and $R^{110}$ may be identical or different.

Structural Formula (IV-2)

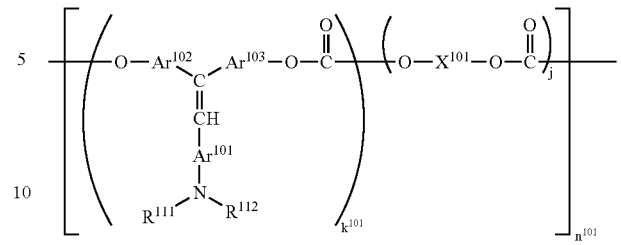

wherein $R^{111}$ and $R^{112}$ each represent a substituted or non-substituted aryl group; $Ar^{101}$, $Ar^{102}$ and $Ar^{103}$, which are identical or different, each represent an arylene group; and $X^{101}$, $k^{101}$, j and $n^{101}$ have the same meanings as described in the above structural formula (I-2).

Structural Formula (V-2)

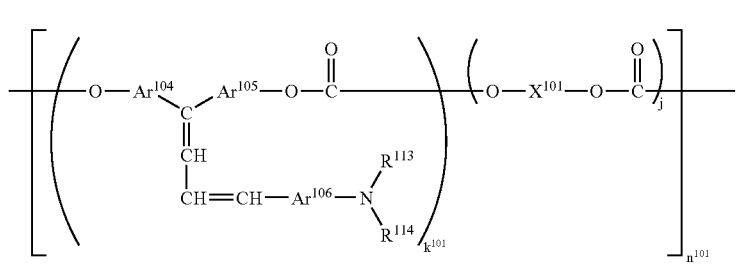

wherein $R^{113}$ and $R^{114}$ each represent a substituted or non-substituted aryl group; $Ar^{104}$, $Ar^{105}$ and $Ar^{106}$, which are identical or different, each represent an arylene group; and $X^{101}$, $k^{101}$, j and $n^{101}$ have the same meanings as described in the above structural formula (I-2).

Structural Formula (VI-2)

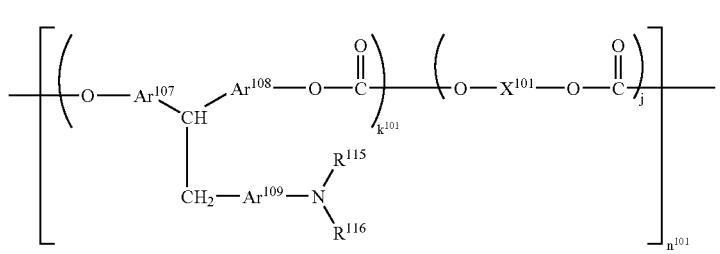

wherein $R^{115}$ and $R^{116}$ each represent a substituted or non-substituted aryl group; $Ar^{107}$, $Ar^{108}$ and $Ar^{109}$, which are identical or different, each represent an arylene group; and $X^{101}$, $k^{101}$, j and $n^{101}$ have the same meanings as described in the above structural formula (I-2).

Structural Formula (VII-2)

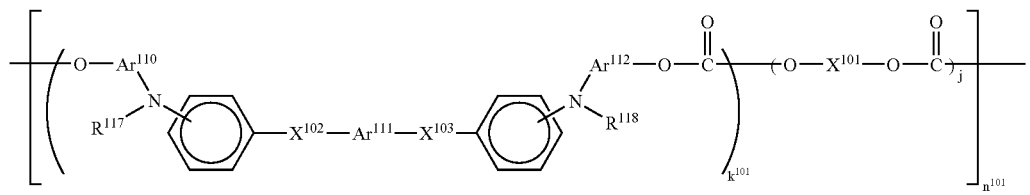

wherein $R^{117}$ and $R^{118}$ each represent a substituted or non-substituted aryl group; $Ar^{110}$, $Ar^{111}$ and $Ar^{112}$, which are identical or different, each represent an arylene group; $X^{102}$ and $X^{103}$ each represent a substituted or non-substituted ethylene group, or a substituted or non-substituted vinylene group; and $X^{101}$, $k^{101}$, j and $n^{101}$ have the same meanings as described in the above structural formula (I-2).

Structural Formula (VIII-2)

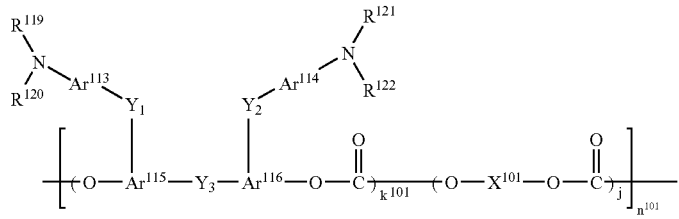

wherein $R^{119}$, $R^{120}$, $R^{121}$ and $R^{122}$ each represent a substituted or non-substituted aryl group; $Ar^{113}$, $Ar^{114}$, $Ar^{115}$ and $Ar^{116}$, which are identical or different, each represent an arylene group; $Y_1$, $Y_2$ and $Y_3$, which may be identical or different, each represent a single bond, substituted or non-substituted alkylene group, substituted or non-substituted cycloalkylene group, substituted or non-substituted alkylene ether group, oxygen atom, sulfur atom or vinylene group; and $X^{101}$, $k^{101}$, j and $n^{101}$ have the same meanings as described in the above structural formula (I-2).

Structural Formula (IX-2)

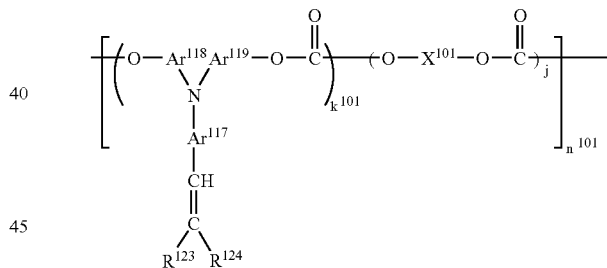

wherein $R^{123}$ and $R^{124}$ each represent a hydrogen atom, a substituted or non-substituted aryl group; $R^{123}$ and $R^{124}$ may be linked to form a ring; $Ar^{117}$, $Ar^{118}$ and $Ar^{119}$, which are identical or different, each represent an arylene group; and $X^{101}$, $k^{101}$, j and $n^{101}$ have the same meanings as described in the above structural formula (I-2).

Structural Formula (X-2)

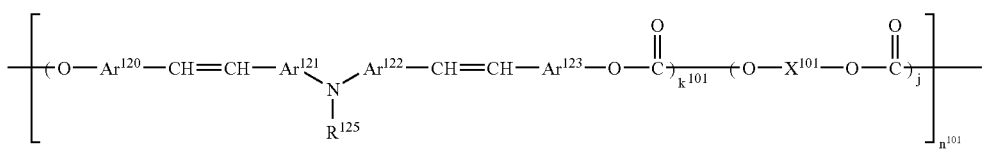

wherein $R^{125}$ represents a substituted or non-substituted aryl group; $Ar^{120}$, $Ar^{121}$, $Ar^{122}$ and $Ar^{123}$, which are identical or different, each represent an arylene group; and $X^{101}$, $k^{101}$, j and $n^{101}$ have the same meanings as described in the above structural formula (I-2).

Structural Formula (XI-2)

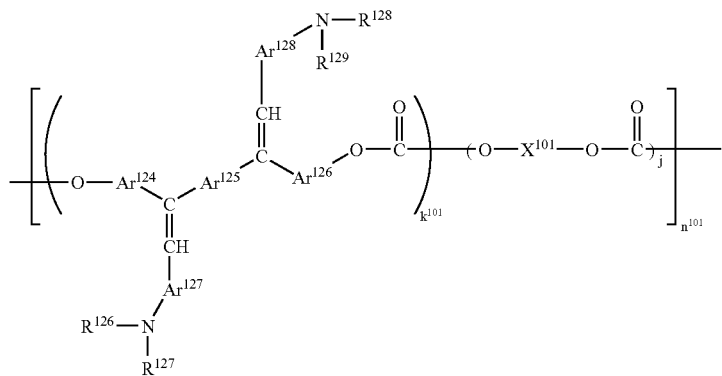

wherein $R^{126}$, $R^{127}$, $R^{128}$ and $R^{129}$ each represent a substituted or non-substituted aryl group; $Ar^{124}$, $Ar^{125}$, $Ar^{126}$, $Ar^{127}$ and $Ar^{128}$, which are identical or different, each represent an arylene group; and $X^{101}$, $k^{101}$, j and $n^{101}$ have the same meanings as described in the above structural formula (I-2).

Structural Formula (XII-2)

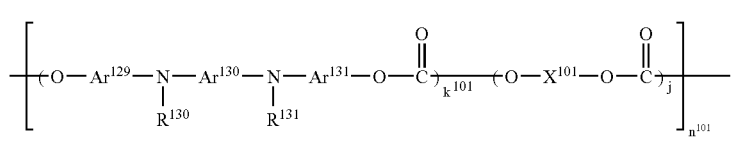

wherein $R^{130}$ and $R^{131}$ each represent a substituted or non-substituted aryl group; $Ar^{129}$, $Ar^{130}$ and $Ar^{131}$, which are identical or different, each represent an arylene group; and $X^{101}$, $k^{101}$, j and $n^{101}$ have the same meanings as described in the above structural formula (I-2).

Structural Formula (XIII-2)

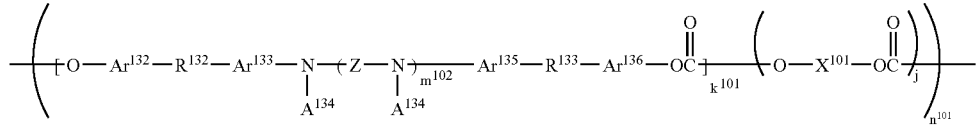

wherein $Ar^{132}$, $Ar^{133}$, $Ar^{134}$, $Ar^{136}$ each represent a substituted or non-substituted aromatic ring group; Z represents an aromatic ring group or —$Ar^{137}$-Za-$Ar^{137}$—, wherein $Ar^{137}$ represents a substituted or non-substituted aromatic ring group; Za represents, O, S or an alkylene group; $R^{132}$ and $R^{133}$ each represent a linear or branched alkylene group; $m^{102}$ is 0 or 1; and $X^{101}$, $k^{101}$, j and $n^{101}$ have the same meanings as described in the above structural formula (I-2).

The charge transport layer 37 may be formed by coating, on the charge generation layer, a coating liquid prepared by dissolving or dispersing the charge transport material solely or in combination with the binder resin in an appropriate solvent, and by drying. If necessary, a plasticizer, a leveling agent, an antioxidant or other additives may be incorporated into the coating liquid. These additives may be used alone or in combination.

The method for coating the coating liquid may be a conventional method such as immersion coating, spray coating, beat coating, nozzle coating, spinner coating or ring coating.

Next, a single-layer photoconductive layer 33 will be described. This layer may be formed of a photoconductor material prepared by dispersing the charge generation material in the binder resin. The single-layer photoconductive layer 33 may be formed by coating a coating liquid which has been prepared by dissolving or dispersing, in an appropriate solvent, the charge generation material, the charge transport material and the binder resin, and by drying of the coated liquid.

If necessary, a plasticizer, a leveling agent, an antioxidant or other additives may be incorporated into the coating liquid.

The binder resin includes those described above in relation to the charge transport layer 37 and the charge generation layer 35. Needless to say, the above-described charge transport polymers are preferably used. The amount of the charge generation material is preferably 5 parts by mass to 40 parts by mass per 100 parts by mass of the binder resin. The amount of the charge transport material is preferably 0 parts by mass to 190 parts by mass, more preferably 50 parts by mass to 150 parts by mass, per 100 parts by mass of the binder resin. The photoconductive layer can be formed as follows: the charge generation material, the binder resin and the charge transport material are dispersed using a disperser in a solvent (e.g., tetrahydrofuran, dioxane, dichloroethane or cyclohexane); and the obtained coating liquid is coated by immersion coating, spray coating, beat coating, nozzle coating and ring coating. The thickness of the photoconductive layer is suitably about 5 µm to about 25 µm.

In the photoconductor of the present invention, an underlying layer may be provided between the conductive support 31 and the photoconductive layer. The underlying layer is generally formed predominantly of resin. The resin preferably is highly resistant to a usual organic solvent, in consideration of subsequent formation of the photoconductive layer using the solvent. Examples of the resin include water-soluble resins (e.g., polyvinyl alcohol, casein and sodium polyacrylate); alcohol-soluble resins (e.g., nylon copolymers and methoxymethylated nylon); and curable resins forming a three-dimensional network structure (e.g., polyurethane, melamine resins, phenol resins, alkyd-melamine resins and epoxy resins). The underlying layer may contain a microparticle pigment of a metal oxide such as titanium oxide, silica, alumina, zirconium oxide, tin oxide or indium oxide, for the purpose of, for example, preventing moire generation and reducing residual potential.

Similar to formation of the photoconductive layer, the underlying layer can be formed using an appropriate solvent and a coating method. In the present invention, the underlying layer may also be formed of a silane coupling agent, a titanium coupling agent or a chlomium coupling agent. In addition, the underlying layer may be an $Al_2O_3$ film formed by anodic oxidation; a film formed by vacuum thin film formation from an organic material (e.g., polyparaxylene (parylene)) or an inorganic material (e.g., $SiO_2$, $SnO_2$, $TiO_2$, ITO or $CeO_2$); or other known films. The thickness of the underlying layer is suitably 0 µm to 5 µm.

In the photoconductor of the present invention, a protective layer 39 may be provided on the photoconductive layer for protecting. The protective layer 39 may be formed, for example, of ABS resins, ACS resins, an olefin-vinylmonomer copolymer, chlorinated polyether, aryl resins, phenol resins, polyacetal, polyamide, polyamideimide, polyacrylate, polyallyl sulfone, polybutylene, polybutylene terephthalate, polyearbonate, polyether sulfone, polyethylene, polyethylene terephthalate, polyimide, acrylic resins, polymethyl pentene, polypropylene, polyphenyleneoxide, polysulfone, polystyrene, polyarylate, AS resins, a butadiene-styrene copolymer, polyurethane, polyvinyl chloride, polyvinylidene chloride or epoxy resins. Use of polycarbonate or polyarylate is particularly advantageous, form the viewpoints of enhancing filler dispersibility, and of reducing residual potential and film defects.

The protective layer of the photoconductor contains a filler material to enhance its wear resistance. The solvent for dispersing the filler material may be any of the above-described solvents used for forming the charge transport layer 37 (e.g., tetrahydrofuran, dioxane, toluene, dichloromethane, monochlorobenzene, dichloroethane, cyclohexanone, methyl ethyl ketone and acetone). Preferably, the solvent employed exhibits and is highly volatile during coating. Without such a solvent that exhibits the above-described properties, a solvent exhibiting high viscosity during dispersion may be used in combination with a solvent being highly volatile during coating. Use of such a solvent or mixture may considerably enhance filler dispersibility and reduce residual potential.

The protective layer may contain an amine compound (described below) serving as an agent preventing deterioration of the rubber or resin material. Also, addition of the charge transport material (or polymer), which is described above in relation to the charge transport layer 37, is advantageous in reduction of residual potential and improvement of image quality.

The method for forming the protective layer may be a conventional method such as immersion coating, spray coating, beat coating, nozzle coating, spinner coating or ring coating. Use of spray coating is preferred from the viewpoint of attaining evenness of the formed film.

In the photoconductor of the present invention, an intermediate layer may be provided between the photoconductive layer and the protective layer. The intermediate layer is generally formed predominantly of binder resin. Examples of the binder resin include polyamide, alcohol-soluble nylon, water-soluble polyvinyl butyral, polyvinyl butyral and polyvinyl alcohol. The intermediate layer is formed by a usual coating method as described above. The thickness of the intermediate layer is suitably about 0.05 µm to about 2 µm.

In the present invention, for the purpose of improving environmental stability of the photoconductor (in particular, preventing reduction of sensitivity and increase in residual potential), an antioxidant, a plasticizer, a lubricant, a UV absorber or a leveling agent may be incorporated into each of the charge generation layer, the charge transport layer, the underlying layer and the protective layer. Typical examples of these additives are listed below.

<<Antioxidant>>

Examples of the antioxidant include, but not limited to, those listed below.

(a) Phenol Compounds:
2,6-di-t-butyl-p-cresol, butylated hydroxyanisole, 2,6-di-t-butyl-4-ethylphenol, n-octadecyl-3-(4'-hydroxy-3',5'-di-t-butylphenol), 2,2'-methylene-bis-(4-methyl-6-t-butylphenol), 2,2'-methylene-bis-(4-ethyl-6-t-butylphenol), 4,4'-thiobis-(3-methyl-6-t-butylphenol), 4,4'-butylidenebis-(3-methyl-6-t-butylphenol), 1,1,3-tris-(2-methyl-4-hydroxy-5-t-butylphenyl)butane, 1,3,5-trimethyl-2,4,6-tris(3,5-di-t-butyl-4-hydroxybenzyl)benzene, tetrakis-[methylene-3-(3',5'-di-t-butyl-4'-hydroxyphenyl)propionate]methane, bis [3,3'-bis(4'-hydroxy-3'-t-butylphenyl)butylic acid]glycol ester, tocopherols, etc.

(b) Paraphenylenediamines:
N-phenyl-N'-isopropyl-p-phenylenediamine, N,N'-di-sec-butyl-p-phenylenediamine, N-phenyl-N-sec-butyl-p-phenylenediamine, N,N'-di-isopropyl-p-phenylenediamine, N,N'-dimethyl-N,N'-di-t-butyl-p-phenylenediamine, etc.

(c) Hydroquinones:
2,5-di-t-octylhydroquinone, 2,6-didodecylhydroquinone, 2-dodecylhydroquinone, 2-dodecyl-5-chlorohydroquinone, 2-t-octyl-5-methylhydroquinone, 2-(2-octadecenyl)-5-methylhydroquinone, etc.

(d) Organic Sulfur-containing Compounds:
dilauryl-3,3'-thiodipropionate, distearyl-3,3'-thiodipropionate, ditetradecyl-3,3'-thiodipropionate, etc.

(e) Organic Phosphorus-containing Compounds:
triphenyl phosphine, tri(nonylphenyl)phosphine, tri(dinonylphenyl)phosphine, tricresylphosphine, tri(2,4-dibutylphenoxy)phosphine, etc.

<<Plasticizer>>

Examples of the plasticizer include, but not limited to, those listed below.

(a) Phosphate Plasticizers:
triphenyl phosphate, tricresyl phosphate, trioctyl phosphate, octyldiphenyl phosphate, trichloroethyl phosphate, cresyldiphenyl phosphate, tributyl phosphate, tri-2-ethylhexyl phosphate, triphenyl phosphate, etc.

(b) Phthalate Plasticizers:
dimethyl phthalate, diethyl phthalate, diisobutyl phthalate, dibutyl phthalate, diheptyl phthalate, di-2-ethylhexyl phthalate, diisooctyl phthalate, di-n-octyl phthalate, dinonyl phthalate, diisononyl phthalate, diisodecyl phthalate, diundecyl phthalate, ditridecyl phthalate, dicyclohexyl phthalate, butylbenzyl phthalate, butyllauryl phthalate, methyloleyl phthalate, octyldecyl phthalate, dibutyl phthalate, dioctyl phthalate, etc.

(c) Aromatic Carboxylate Plasticizers:
trioctyl trimellitate, tri-n-octyl trimellitate, octyl oxybenzoate, etc.

(d) Aliphatic Dibasic Acid Ester Plasticizers:
dibutyl adipate, di-n-hexyl adipate, di-2-ethylhexyl adipate, di-n-octyl adipate, n-octyl-n-decyl adipate, diisodecyl adipate, dicapryl adipate, di-2-ethylhexyl azelate, dimethyl sebacate, diethyl sebacate, dibutyl sebacate, di-n-octyl sebacate, di-2-ethylhexyl sebacate, di-2-ethoxyethyl sebacate, dioctyl succinate, diisodecyl succinate, dioctyl tetrahydrophthalate, di-n-octyl tetrahydrophthalate, etc.

(e) Fatty Acid Ester Derivatives:
butyl oleate, glycerine monooleate, methyl acetylricinolate, pentaerythritol esters, dipentaerythritol hexaester, triacetin, tributyrin, etc.

(f) Oxy-acid Ester Plasticizers:
methyl acetylricinolate, butyl acetylricinolate, butylphthalyl butylglycolate, tributyl acetycitrate, etc.

(g) Epoxy Plasticizers:
epoxidized soybean oil, epoxidized linseed oil, butyl epoxystearate, decyl epoxystearate, octyl epoxystearate, benzyl epoxystearate, dioctyl epoxyhexahydrophthalate, didecyl epoxyhexahydrophthalate, etc.

(h) Dihydric Alcohol Ester Plasticizers:
diethyleneglycol dibenzoate, triethyleneglycol di-2-ethylbutyrate, etc.

(i) Chlorine-containing Plasticizers:
chlorinated paraffins, chlorinated diphenyl, chlorinated fatty acid methyl, methoxy chlorinated fatty acid methyl, etc.

(j) Polyester Plasticizers:
polypropylene adipate, polypropylene sebacate, polyester, acetylated polyester, etc.

(k) Sulfonic Acid Derivatives:
p-toluenesulfonamide, o-toluenesulfonamide, p-toluenesulfone ethylamide, o-toluenesulfone ethylamide, toluenesulfone-N-ethylamide, p-toluenesulfone-N-cyclohexylamide, etc.

(l) Citric Acid Derivatives:
triethyl citrate, triethyl acetylcitrate, tributyl citrate, tributyl acetylcitrate, tri-2-ethylhexyl acetylcitrate, n-octyldecyl acetylcitrate, etc.

(m) Others:
terphenyls, partially hydrogenated terphenyls, camphor, 2-nitrodiphenyl, dinonylnaphthalene, methyl abietate, etc.

<<Lubricant>>
Examples of the lubricant include, but not limited to, those listed below.

(a) Hydrocarbon Compounds:
liquid paraffin, paraffin wax, micro wax, low polymerized polyethylene, etc.

(b) Fatty Acid Compounds:
lauric acid, myristic acid, palmitic acid, stearic acid, arachidic acid, behenic acid, etc.

(c) Fatty Acid Amide Compounds:
stearylamide, palmitylamide, oleinamide, methylene bis-stearoamide, ethylene bisstearoamide, etc.

(d) Ester Compounds:
fatty acid-lower alcohol esters, fatty acid-polyhydric alcohol esters, fatty acid-polyglycol esters, etc.

(e) Alcohol Compounds:
cetyl alcohol, stearyl alcohol, ethylene glycol, polyethylene glycol, polyglycerol, etc.

(f) Metal Soap:
lead stearate, cadmium stearate, barium stearate, calcium stearate, zinc stearate, magnesium stearate, etc.

(g) Naturally Occurring Waxes:
carnauba wax, candelilla wax, bees wax, whale wax, chinese insect wax, montan wax, etc.

(h) Others:
silicone compounds, fluorine compounds, etc.

<<UV Absorber>>
Examples of the UV absorber include, but not limited to, those listed below.

(a) Benzophenones:
2-hydroxybenzophenone, 2,4-dihydroxybenzophenone, 2,2',4-trihydroxybenzophenone, 2,2',4,4'-tetrahydroxybenzophenone, 2,2'-dihydroxy-4-methoxybenzophenone, etc.

(b) Salicylates:
phenyl salicylate, 2,4-di-t-butylphenyl-3,5-di-t-butyl-4-hydroxy benzoate, etc.

(c) Benzotriazoles:
(2'-hydroxyphenyl)benzotriazole, (2'-hydroxy-5'-methylphenyl) benzotriazole, (2'-hydroxy-5'-methylphenyl) benzotriazole, (2'-hydroxy-3'-tert-butyl-5'-methylphenyl) 5-chlorobenzotriazole, etc.

(d) Cyanoacrylates:
ethyl-2-cyano -3,3-diphenylacrylate, methyl-2-carbomethoxy-3-(paramethoxy)acrylate, etc.

(e) Quenchers (Metal Complex Salts):
nickel (2,2'thiobis(4-t-octyl)phenolate)n-butylamine, nickel dibutyldithiocarbamate, cobalt dicyclohexyldithiophosphate, etc.

(f) HALSs (Hindered Amines):
bis(2,2,6,6-tetramethyl-4-piperidyl) sebacate, bis(1,2,2,6,6-pentamethyl-4-piperidyl) sebacate, 1-[2-[3-(3,5-di-t-butyl-4-hydroxyphenyl)propionyloxy]ethyl]-4-[3-(3,5-di-t-butyl-4-hydroxyphenyl)propionyloxy]-2,2,6,6-tetramethylpyridine, 8-benzyl-7,7,9,9-tetramethyl-3-octyl-1,3,8-triazaspiro[4.5]undecan-2,4-dione, 4-benzoyloxy-2,2,6,6-tetramethyl piperidine, etc.

With reference to the drawings, next will be described in detail an electrophotographic method and an electrophotographic apparatus of the present invention.

Figure 7:
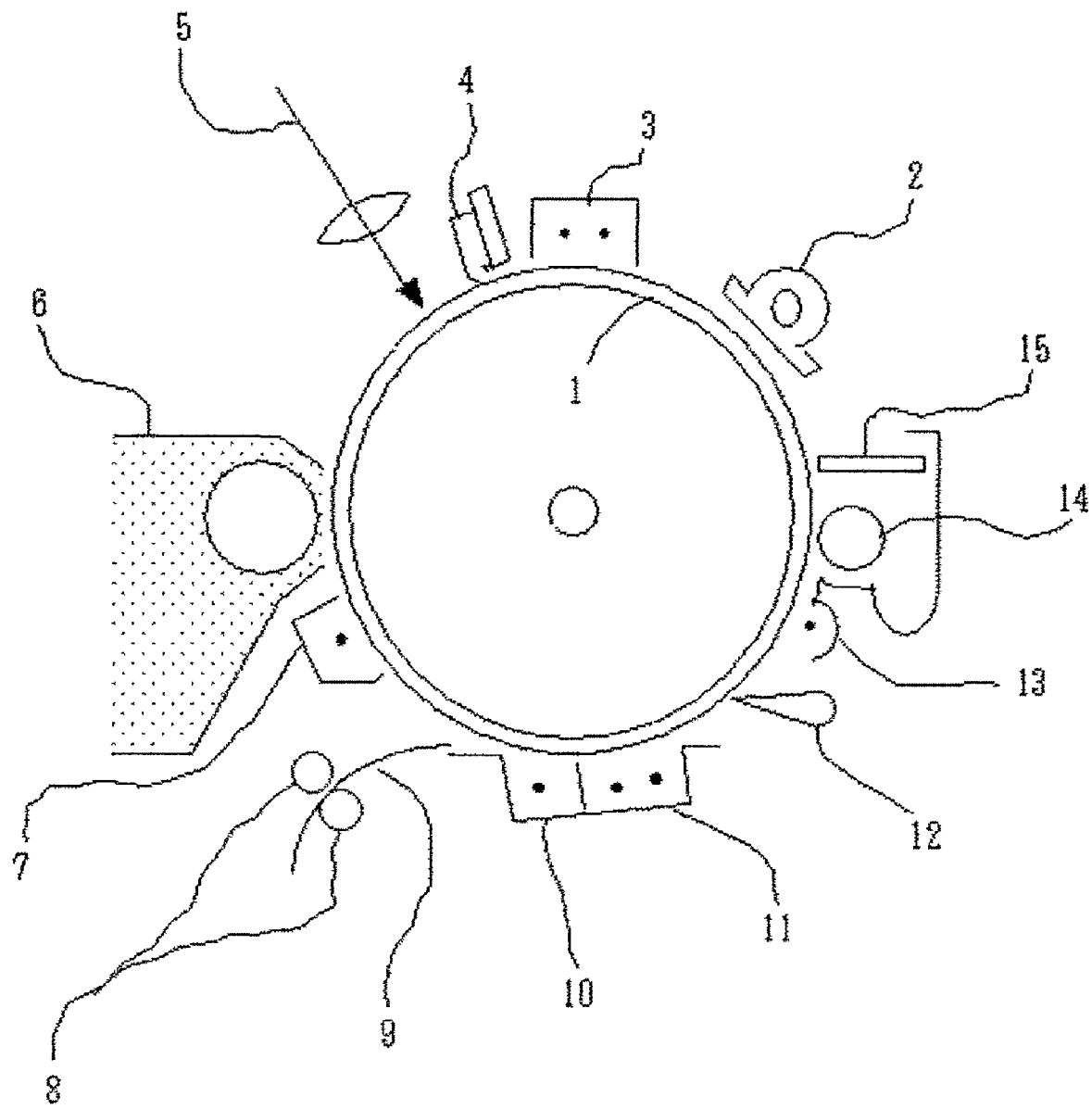
FIG. 7 is a schematic view for describing an electrophotographic process and an electrophotographic apparatus of the present invention.

FIG. 7 is a schematic view for describing the present electrophotographic process and apparatus. The below-described process and apparatus fall within the scope of the present invention.

In FIG. 7, a photoconductor 1 has a shape of drum. Alternatively, the photoconductor 1 may have a shape of sheet or endless belt. Around the photoconductor 1 are provided a charger 3, a pre-transfer charger 7, a transfer charger 10, a separation charger 11, a pre-cleaning charger 13, an imagewise light exposing portion 5, a charge-eliminating lamp 2, a developing unit 6, a fur brush 14, a cleaning blade 15, an eraser 4, resist rollers 8 and a separating hook 12. Each charger may be any of known chargers such as a corotron, a scorotron, a solid state charger and a charging roller.

Generally, a transferring unit may be any of the above-listed chargers. The transferring unit is advantageously a combination of the transfer charger and the separation charger as shown in FIG. 7.

A light source used in the imagewise light exposing portion 5, the charge-eliminating lamp 2, etc. may be a usual light-emitting device such as a fluorescent lamp, a tungsten lamp, a halogen lamp, a mercury lamp, a sodium lamp, a light-emitting diode (LED), a laser diode (LD) or an electroluminescence (EL) lamp. Also, a filter may be used for applying light having a desired wavelength. The filter may be, for example, a sharp-cut filter, a band-pass filter, a near-infrared cut filter, a dichroic filter, an interference filter or a color conversion filter. The photoconductor 1 is irradiated with light at a transfer step, a charge-eliminating step, a cleaning step or a pre-light exposing step (each including light irradiation).

An image is developed on the photoconductor 1 by the developing unit 6 using toner particles, and the toner image is transferred to a transfer paper 9. During this transfer, some toner particles remain on the photoconductor 1. Such residual toner particles are removed from the photoconductor by the fur brush 14 and the cleaning blade 15. In some cases, toner cleaning is carried out by only a cleaning brush. The cleaning brush may be a known brush such as a fur brush or a magfur brush.

An electophotographic photoconductor is provided with positive (negative) charges, and then the electophotographic photoconductor is subjected to imagewise light exposure, whereby a positive (negative) electrostatic latent image is formed thereon. When the positive (negative) electrostatic latent image is developed using negatively (positively) charged toner particles (charge-detecting microparticles), a positive image is obtained, whereas when the positive (negative) electrostatic latent image is developed using positively (negatively) charged toner particles, a negative image is obtained. A developing unit for carrying out the above procedure may employ a known method. A charge-eliminating unit also may employ a known method.

Figure 8:
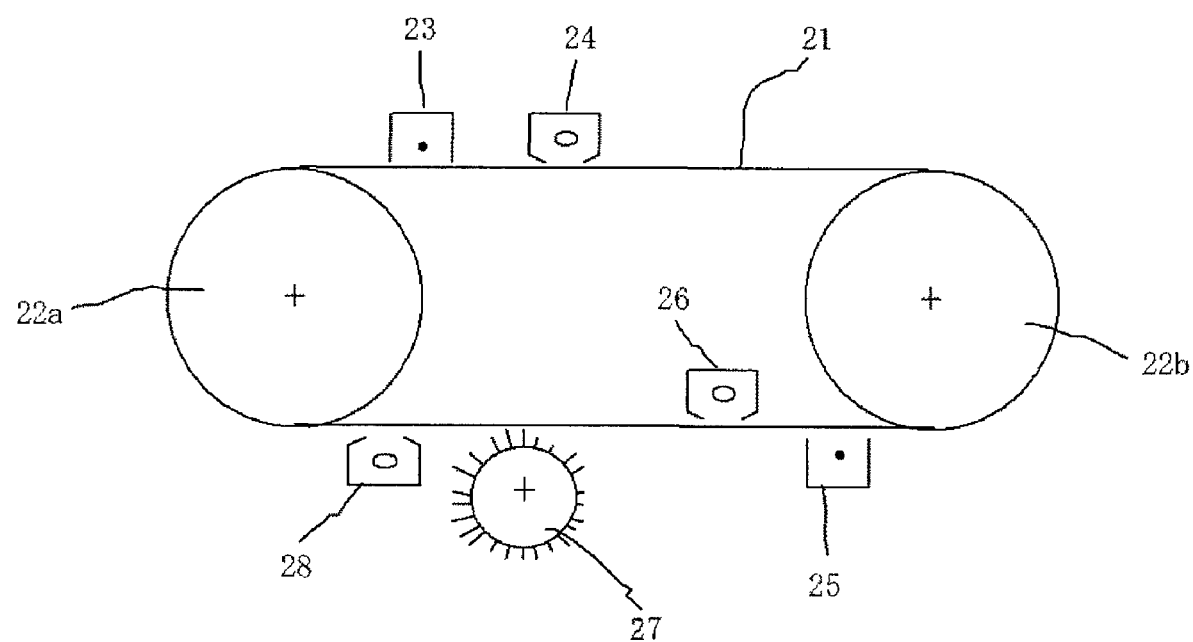
FIG. 8 shows another embodiment of an electrophotographic process of the present invention.

FIG. 8 shows another embodiment of the present electrophotographic process. An apparatus used in this process has a photoconductor 21, drive rollers 22a and 22b, an charger 23, a light source for imagewise light exposure (imagewise exposing-light source) 24, a developing device (not illustrated), a transfer charger 25, a light source 26, a cleaning brush 27 and an charge-eliminating light source 28. The photoconductor 21 has at least a photoconductive layer, and also contains a filler in the uppermost layer. In the process, while the photoconductor 21 is driven by the drive rollers, there is repeated a cycle including charging by the charger 23, imagewise light exposure by the imagewise exposing-light source 24, development by the developing device, transfer by the transfer charger 25, pre-cleaning light exposure by the light source 26, cleaning by the cleaning brush 27, and charge elimination by the charge-eliminating light source 28. In the apparatus shown in FIG. 8, pre-cleaning light exposure is carried out by applying light from the side facing a support of the photoconductor 21 (in this case, the support has an optical transparency).

The above-described electrophotographic processes are exemplary embodiments of the present invention and, needless to say, other embodiments can be realized. For example, although pre-cleaning light exposure is carried out on the support side in FIG. 8, this light exposure may be carried out on the photoconductive layer side. Also, differing from the case shown in FIG. 8, imagewise light exposure and charge elimination may be carried out by applying light from the side facing the photoconductor support.

In addition, although the photoconductor is irradiated with light upon imagewise light exposure, pre-cleaning light exposure and charge-eliminating light exposure in FIG. 8, additional light irradiation may be carried out by provision of known light-irradiating steps (e.g., pre-transfer light exposure and pre-light exposure for imagewise light exposure).

Figure 9:
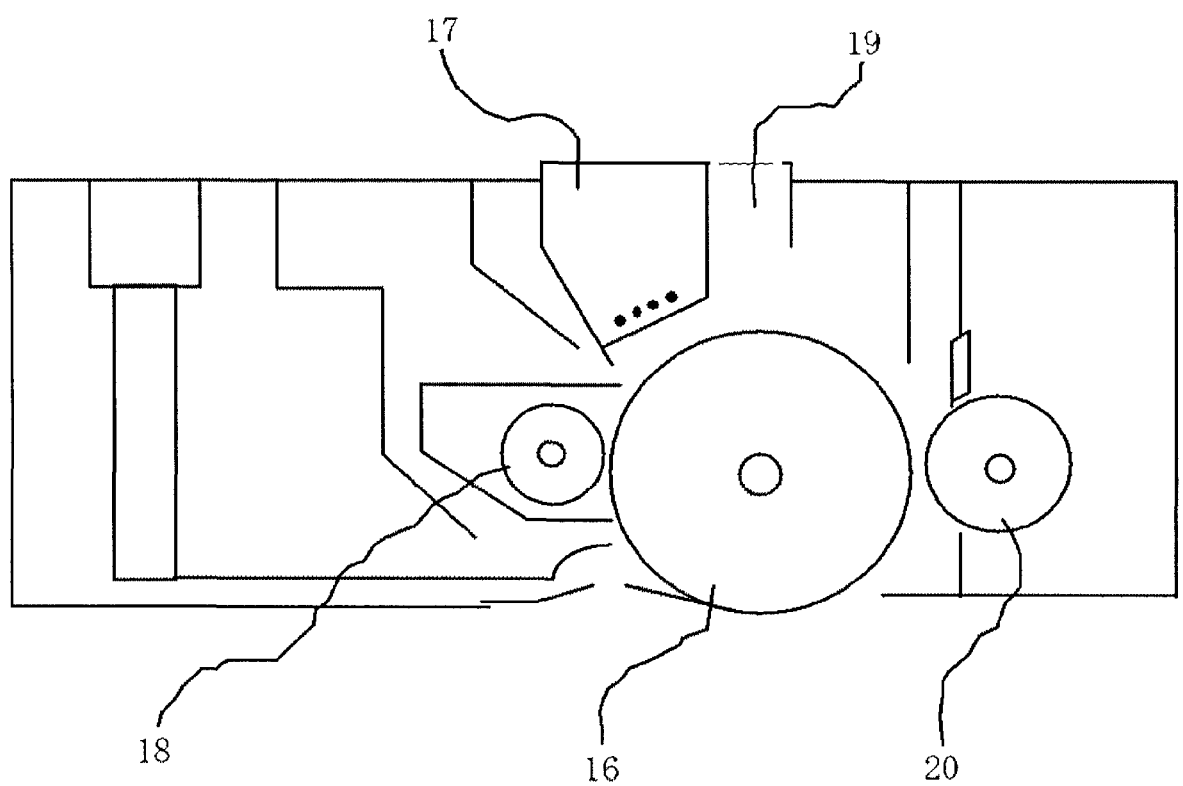
FIG. 9 is a schematic view for describing an electrophotographic process cartridge of the present invention.

The above-described image-forming unit may be fixed in a copier, a facsimile or a printer; or may be mounted therein in the form of a process cartridge. The process cartridge is a one-piece device (part) including a photoconductor, a charging unit, a light-exposing unit, a developing unit, a transferring unit, a cleaning unit and a charge-eliminating unit. The process cartridge varies in shape or the like, and a typical example thereof is shown in FIG. 9. In FIG. 9, reference numerals 16, 17, 18, 19 and 20 indicate a photoconductor, a charger, a cleaning brush, an imagewise light exposing portion and a developing roller, respectively.

EXAMPLES

The present invention will next be described by way of examples, which should not be construed as limiting the present invention thereto. In the Examples, "part(s) by mass" may be abbreviated as "part(s)".

Example 1

(Production of Monoimide Compound)

Naphthalene-1,4,5,8-tetracarboxylic dianhydride (product of TOKYO CHEMICAL INDUSTRY CO., LTD.) (5.36 g, 20.0 mmol), N,N-dimethylformamide (30 mL) and acetic acid (3 mL) were added to a flask, followed by refluxing. A solution of 2-heptylamine (2.42 g, 21.0 mmol) in N,N-dimethylformamide (6 mL) was added dropwise to the resultant mixture under stirring for about two hours. Further, the mixture was allowed to react for five hours under refluxing. After cooling, the solvent was evaporated under reduced pressure. Toluene was added to the residue and insoluble matter was removed by filtration. The filtrate was purified by silica gel chromatography, followed by recrystallization from cyclohexane/toluene, to thereby yield 3.02 g of a monoimide compound represented by the following structural formula (i) (yield: 41.3%). The melting point of the compound was found to be 149.0° C. to 150.0° C.

Structural Formula (i)

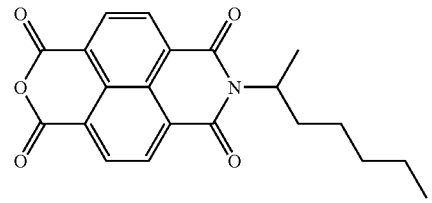

The above compound was subjected to elemental analysis. The results are shown in Table 6.

TABLE 6

|  | C | H | N |
|---|---|---|---|
| Found | 69.05 | 5.27 | 3.74 |
| Calculated | 69.03 | 5.24 | 3.83 |

The above compound was subjected to infrared spectroscopy by the KBr tablet method. The obtained infrared absorption spectrum exhibits an absorption peak at 1,787 cm$^{-1}$ derived from an acid anhydride moiety, and an absorption peak at 1,670 cm$^{-1}$ derived from an imide moiety.

(Production of Naphthalenetetracarboxylic Acid Diimide Derivative Corresponding to Compound No. 1)

Under a stream of argon, the above-obtained monoimide compound (1.83 g, 5.00 mmol) was dissolved in N,N-dimethylformamide (anhydrous, 10 mL). A solution of 1,1-dimethylhydrazine (product of TOKYO CHEMICAL INDUSTRY CO., LTD.) (0.300 g, 5.00 mmol) in N,N-dimethylformamide (anhydrous, 5 mL) was added under stirring to the solution. The resultant solution was stirred at room temperature for two hours. The solvent (N,N-dimethylformamide) was evaporated under reduced pressure, to thereby form tango crystals. The crystals were purified using a silica gel column (eluent: toluene/ethyl acetate (2/1 vol.)). The purified orange crystals were recrystallized from toluene/n-hexane. The obtained crystals were dried by a dryer in which heating is performed under reduced pressure, to thereby yield 1.49 g of a naphthalenetetracarboxylic acid diimide derivative represented by the following structural formula (ii) in the form of orange-yellow needles (yield: 73.0%). The melting point of this compound was found to be 166.0° C. to 167.0° C.

Structural Formula (ii)

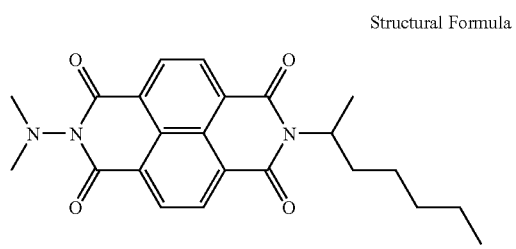

The obtained compound was subjected to elemental analysis. The results are shown in Table 7.

TABLE 7

|  | C | H | N |
|---|---|---|---|
| Found | 67.91 | 6.10 | 10.22 |
| Calculated | 67.80 | 6.18 | 10.31 |

Example 2

(Production of Compound No. 30)

A part (1.83 g, 5.00 mmol) of the monoimide compound obtained in Example 1 was added to N,N-dimethylformamide (15 mL). 1,1-Dibenzylhydrazine (product of TOKYO CHEMICAL INDUSTRY CO., LTD.) (1.06 g, 5.00 mmol) was added to the mixture, followed by stirring under a stream of argon at 60° C. for 3.5 hours. The solvent (N,N'-dimethylformamide) was evaporated under reduced pressure, to thereby form red crystals. The crystals were purified using a silica gel column (eluent: toluene/ethyl acetate (30/1 vol.)). The obtained tango crystals were recrystallized from ethyl acetate/ethanol. The obtained crystals were dried by a dryer in which heating is performed under reduced pressure, to thereby yield 2.21 g of Compound No. 30 represented by the following structural formula (iii) in the form of yellow needles (yield: 78.9%). The melting point of this compound was found to be 147.0° C. to 148.0° C.

Structural Formula (iii)

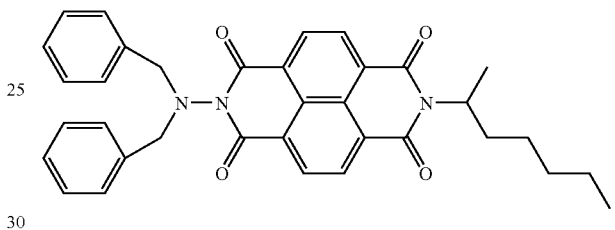

The obtained compound was subjected to elemental analysis. The results are shown in Table 8.

TABLE 8

|  | C | H | N |
|---|---|---|---|
| Found | 74.98 | 5.88 | 7.53 |
| Calculated | 75.11 | 5.94 | 7.51 |

Examples 3 to 21

Similar to Examples 1 and 2, compounds corresponding to Examples 3 to 21 were produced and analyzed. The results are shown in Tables 9-1 and 9-2.

TABLE 9-1

| Ex. No. | Structural formula | Yield (%) | m.p. (° C.) | Elemental Analysis (%) Found (Calcd.) | | |
|---|---|---|---|---|---|---|
| | | | | C | H | N |
| 3 | | 80.9 | 148.0-149.0 | 68.00 (67.80) | 6.21 (6.18) | 10.28 (10.31) |
| 4 | | 78.9 | 207.5-208.5 | 66.54 (66.48) | 5.62 (5.58) | 11.03 (11.08) |

TABLE 9-1-continued

| Ex. No. | Structural formula | Yield (%) | m.p. (° C.) | Elemental Analysis (%) Found (Calcd.) | | |
|---|---|---|---|---|---|---|
| | | | | C | H | N |
| 5 | | 78.3 | 211.5-212.0 | 71.66 (71.62) | 5.90 (5.80) | 9.00 (8.95) |
| 6 | | 67.2 | 162.0-164.0 | 71.48 (71.62) | 5.76 (5.80) | 8.96 (8.95) |
| 7 | | 68.2 | 130.5-131.5 | 72.01 (72.03) | 5.99 (6.04) | 8.79 (8.69) |
| 8 | | 67.4 | 159.0-161.0 | 71.98 (72.03) | 6.03 (6.04) | 8.58 (8.69) |
| 9 | | 57.5 | 203.5-204.5 | 71.10 (71.19) | 5.44 (5.53) | 9.11 (9.22) |
| 10 | | 75.2 | amorphous crystals | 74.61 (74.56) | 5.45 (5.50) | 7.88 (7.90) |

TABLE 9-2

| Ex. No. | Structural formula | Yield (%) | m.p. (° C.) | Elemental Analysis (%) Found (Calcd.) | | |
|---|---|---|---|---|---|---|
| | | | | C | H | N |
| 11 | | 85.7 | amorphous crystals | 74.49 (74.56) | 5.30 (5.50) | 7.96 (7.90) |
| 12 | | 72.6 | 197.0-198.0 | 73.74 (73.94) | 4.96 (5.00) | 8.27 (8.34) |
| 13 | | 72.4 | amorphous crystals | 73.89 (73.94) | 4.98 (5.00) | 8.29 (8.34) |
| 14 | | 80.0 | 195.5-196.5 | 75.01 (75.11) | 5.92 (5.94) | 7.47 (7.51) |
| 15 | | 53.5 | 131.0-133.0 | 74.66 (74.84) | 5.69 (5.73) | 7.80 (7.70) |
| 16 | | 54.6 | 243.0-243.5 | 69.90 (69.72) | 4.54 (4.63) | 10.02 (10.16) |

TABLE 9-2-continued

| Ex. No. | Structural formula | Yield (%) | m.p. (° C.) | Elemental Analysis (%) Found (Calcd.) | | |
|---|---|---|---|---|---|---|
| | | | | C | H | N |
| 17 | | 45.3 | 190.5-191.5 | 70.12 (70.25) | 5.00 (4.95) | 9.77 (9.83) |
| 18 | | 60.9 | 250.5-251.0 | 72.95 (73.25) | 4.50 (4.45) | 8.75 (8.84) |
| 19 | | 64.0 | 251.0-252.0 | 73.88 (73.61) | 4.80 (4.74) | 8.48 (8.58) |
| 20 | | 54.2 | 205.0-206.0 | 71.59 (71.66) | 5.00 (4.85) | 7.95 (8.09) |
| 21 | | 64.9 | 238.0-239.0 | 74.01 (73.94) | 5.04 (5.00) | 8.26 (8.34) |

Example A-1

(Production of Compound (A-1))
<Production of Monoimide Compound>
1,4,5,8-Naphthalenetetracarboxylic dianhydride (5.36 g, 20 mmol), N,N-dimethylformamide (anhydrous, 30 mL) and acetic acid (3 mL) were added to a flask, followed by refluxing. A solution of 2-heptylamine (2.42 g, 21 mmol) in N,N-dimethylformamide (anhydrous, 6 mL) was added dropwise to the resultant mixture under stirring for about two hours. Further, the mixture was allowed to react for five hours under refluxing. After cooling, the solvent was evaporated under reduced pressure. Toluene was added to the residue and insoluble matter was removed by filtration. The filtrate was purified by silica gel chromatography, followed by recrystallization from cyclohexane/toluene, to thereby yield 3.02 g of a monoimide compound.

Elemental analysis (as $C_{21}H_{19}NO_5$)

TABLE 10

| | C | H | N |
|---|---|---|---|
| Found (%) | 69.05 | 5.27 | 3.74 |
| Calculated (%) | 69.03 | 5.24 | 3.83 |

The above compound was subjected to infrared spectroscopy by the KBr tablet method. The obtained infrared absorption spectrum exhibits an absorption peak at 1,787 cm$^{-1}$ derived from an acid anhydride moiety, and an absorption peak at 1,670 cm$^{-1}$ derived from an imide moiety.

(Production of the Target Compound)

A part (1.83 g, 5 mmol) of the above-obtained monoimide compound, N,N-dimethylformamide (anhydrous, 30 mL) and acetic acid (1 mL) were added to a flask. 1-Aminopiperidine (0.60 g, 6 mmol) was added dropwise to the mixture under stirring. The resultant mixture was heated to about 80° C. and allowed to further react for four hours. After cooling, the solvent was evaporated under reduced pressure. The residue (product) was washed with methanol, followed by filtration. The obtained product was recrystallized repeatedly from n-hexane-toluene and ethanol-toluene, to thereby yield 1.54 g of the target naphthalenetetracarboxylic acid diimide derivative (Compound (A-1)).

Melting point: 184.5° C. to 185.5° C.

Elemental analysis (as $C_{26}H_{29}N_3O_4$)

TABLE 11

|  | C | H | N |
| --- | --- | --- | --- |
| Found (%) | 69.85 | 6.41 | 9.44 |
| Calculated (%) | 69.78 | 6.53 | 9.39 |

The above compound was subjected to infrared spectroscopy by the KBr tablet method. The obtained infrared absorption spectrum exhibits no absorption peak at 1,787 cm$^{-1}$ derived from an acid anhydride moiety, and intense absorption peaks at 1,683 cm$^{-1}$ and 1,660cm$^{-1}$ derived from amide moieties.

Example A-2

(Production of Compound (A-14))

A part (1.83 g, 5 mmol) of the monoimide compound obtained in Example A-1, N,N-dimethylformamide (anhydrous, 30 mL) and acetic acid (2 mL) were added to a flask. 1-Amino-2,6-dimethylpiperidine (0.77 g, 6 mmol) was added dropwise to the mixture under stirring. The resultant mixture was heated to about 80° C. and allowed to further react for five hours. After cooling, the solvent was evaporated under reduced pressure. Toluene was added to the residue (product) and the formed organic layer was washed with water, followed by purification by silica gel chromatography, to thereby yield 1.48 g of the target naphthalenetetracarboxylic acid diimide derivative (Compound (A-14)). Melting point: 95.0° C. to 98.0° C.

Elemental analysis (as $C_{28}H_{33}N_3O_4$)

TABLE 12

|  | C | H | N |
| --- | --- | --- | --- |
| Found (%) | 70.77 | 7.04 | 8.69 |
| Calculated (%) | 70.71 | 6.99 | 8.84 |

The above compound was subjected to infrared spectroscopy by the KBr tablet method. The obtained infrared absorption spectrum exhibits no absorption peak at 1,787 cm$^{-1}$ derived from an acid anhydride moiety, and intense absorption peaks at 1,683 cm$^{-1}$ and 1,660cm$^{-1}$ derived from amide moieties.

Example A-3

(Production of Compound (A-21))

A part (1.83 g, 5 mmol) of the monoimide compound obtained in Example A-1, N,N-dimethylformamide (anhydrous, 30 mL) and acetic acid (2 mL) were added to a flask. 1-Aminohomopiperidine (0.69 g, 6 mmol) was added dropwise to the mixture under stirring. The resultant mixture was heated to about 80° C. and allowed to further react for four hours. After cooling, the solvent was evaporated under reduced pressure. The residue (product) was washed with methanol, followed by filtration. The obtained product was purified by silica gel chromatography, to thereby yield 1.53 g of the target naphthalenetetracarboxylic acid diimide derivative (Compound (A-21)).

Melting point: 132.0° C. to 133.0° C.

Elemental analysis (as $C_{27}H_{31}N_3O_4$)

TABLE 13

|  | C | H | N |
| --- | --- | --- | --- |
| Found (%) | 70.35 | 6.79 | 9.23 |
| Calculated (%) | 70.26 | 6.77 | 9.10 |

The above compound was subjected to infrared spectroscopy by the KBr tablet method. The obtained infrared absorption spectrum exhibits no absorption peak at 1,787 cm$^{-1}$ derived from an acid anhydride moiety, and intense absorption peaks at 1,679 cm$^{-1}$ and 1,654cm.$^{-1}$ derived from amide moieties.

Example A-4

(Production of Compound (A-29))

The monoimide compound obtained in Example A-1 (3.65 g, 10 mmol) and N,N-dimethylformamide (anhydrous, 40 mL) were added to a flask. 1-Amino-4-methylpiperazine (1.38 g, 12 mmol) was added dropwise to the mixture under stirring. The resultant mixture was allowed to further react at room temperature for six hours. The solvent was evaporated under reduced pressure. The residue (product) was washed with methanol, followed by filtration. The obtained product was recrystallized repeatedly from cyclohexane-toluene and ethanol-toluene, to thereby yield 3.7 g of the target naphthalenetetracarboxylic acid diimide derivative (Compound (29)).

Melting point: 210.0° C. to 210.5° C.

Elemental analysis (as $C_{26}H_{30}N_4O_4$)

TABLE 14

|  | C | H | N |
| --- | --- | --- | --- |
| Found (%) | 67.58 | 6.68 | 12.09 |
| Calculated (%) | 67.51 | 6.54 | 12.11 |

The above compound was subjected to infrared spectroscopy by the KBr tablet method. The obtained infrared absorption spectrum exhibits no absorption peak at 1,787 cm$^{-1}$ derived from an acid anhydride moiety, and intense absorption peaks at 1,683 cm$^{-1}$ and 1,658cm$^{-1}$ derived from amide moieties.

Example A-5

(Production of Compound (A-41))

The monoimide compound obtained in Example A-1 (3.65 g, 10 mmol), N,N-dimethylformamide (anhydrous, 60 mL) and acetic acid (5 mL) were added to a flask. N-Aminomorpholine (1.23 g, 12 mmol) was added dropwise to the mixture under stirring. The resultant mixture was heated to about 80° C. and allowed to further react for two hours. After cooling, the solvent was evaporated under reduced pressure. The residue (product) was washed with methanol, followed by filtration. The obtained product was recrystallized repeatedly from cyclohexane-toluene and ethanol-toluene, to thereby yield 3.62 g of the target naphthalenetetracarboxylic acid diimide derivative (Compound (41)).
Melting point: 200.0° C. to 201.5° C.
Elemental analysis (as $C_{25}H_{27}N_3O_5$)

TABLE 15

|  | C | H | N |
|---|---|---|---|
| Found (%) | 66.95 | 6.24 | 9.22 |
| Calculated (%) | 66.80 | 6.05 | 9.35 |

The above compound was subjected to infrared spectroscopy by the KBr tablet method. The obtained infrared absorption spectrum exhibits no absorption peak at 1,787 $cm^{-1}$ derived from an acid anhydride moiety, and an intense absorption peak at 1,683 $cm^{-1}$ derived from an amide moiety.

Example A-6

(Production of Compound (A-2))
(Production of Monoimide Compound)
1,4,5,8-Naphthalenetetracarboxylic andihydride (2.7 g, 10 mmol) and N,N-dimethylformamide (anhydrous, 25 mL) were added to a flask, followed by refluxing. A solution of 2-aminooctane (1.34 g, 10.3 mmol) in N,N-dimethylformamide (anhydrous, 5 mL) was added dropwise to the mixture under stirring for about one hour. The resultant mixture was allowed to further react for six hours under refluxing After cooling, the solvent was evaporated under reduced pressure. Toluene was added to the residue and insoluble matter was removed by filtration. The filtrate was purified by silica gel chromatography, followed by recrystallization from cyclohexane, to thereby yield 1.6 g of a monoimide compound.
Elemental analysis (as $C_{22}H_{21}NO_5$)

TABLE 16

|  | C | H | N |
|---|---|---|---|
| Found (%) | 69.69 | 5.41 | 3.66 |
| Calculated (%) | 69.66 | 5.58 | 3.69 |

The above compound was subjected to infrared spectroscopy by the KBr tablet method. The obtained infrared absorption spectrum exhibits an absorption peak at 1,787 $cm^{-1}$ derived from an acid anhydride moiety, and an absorption peak at 1,667 $cm^{-1}$ derived from an imide moiety.
(Production of the Target Compound)
The above-obtained monoimide compound (1.90 g, 5 mmol), N,N-dimethylformamide (anhydrous, 30 mL) and acetic acid (2 mL) were added to a flask. 1-Aminopiperidine (0.60 g, 6 mmol) was added dropwise to the mixture under stirring. The resultant mixture was heated to about 80° C. and allowed to further react for four hours. After cooling, the solvent was evaporated under reduced pressure. The residue (product) was washed with methanol, followed by filtration. The obtained product was recrystallized repeatedly from cyclohexane, to thereby yield 2.13 g of the target naphthalenetetracarboxylic acid diimide derivative (Compound (A-2)).
Melting point: 187.5° C. to 188.0° C.

Elemental analysis (as $C_{27}H_{31}N_3O_4$)

TABLE 17

|  | C | H | N |
|---|---|---|---|
| Found (%) | 70.34 | 6.65 | 9.22 |
| Calculated (%) | 70.26 | 6.77 | 9.10 |

The above compound was subjected to infrared spectroscopy by the KBr tablet method. The obtained infrared absorption spectrum exhibits no absorption peak at 1,787 $cm^{-1}$ derived from an acid lo anhydride moiety, and intense absorption peaks at 1,675 $cm^{-1}$ and 1,660 $cm^{-1}$ derived from amide moieties.

Example A-7

(Production of Compound (A-42))
The monoimide compound obtained in Example A-6 (1.90 g, 5 mmol), N,N-dimethylformamide (anhydrous, 30 mL) and acetic acid (3 mL) were added to a flask. N-Aminomorpholine (0.61 g, 6 mmol) was added dropwise to the mixture under stirring. The resultant mixture was heated to about 80° C. and allowed to further react for five hours. After cooling, the solvent was evaporated under reduced pressure. The residue (product) was washed with methanol, followed by filtration. The obtained product was recrystallized repeatedly from n-hexane-toluene and ethanol-toluene, to thereby yield 2.20 g of the target naphthalenetetracarboxylic acid diimide derivative (Compound (42)).
Melting point: 198.5° C. to 200.0° C.
Elemental analysis (as $C_{26}H_{29}N_3O_5$)

TABLE 18

|  | C | H | N |
|---|---|---|---|
| Found (%) | 67.44 | 6.35 | 9.17 |
| Calculated (%) | 67.37 | 6.31 | 9.06 |

The above compound was subjected to infrared spectroscopy by the KBr tablet method. The obtained infrared absorption spectrum exhibits no absorption peak at 1,787 $cm^{-1}$ derived from an acid anhydride moiety, and an intense absorption peak at 1,675 $cm^{-1}$ derived from an amide moiety.
Application Example (According to Example A-3 of JP-A No. 2007-108682)
An electrophotographic photoconductor used in Application Example was fabricated as follows.
A metal-free phthalocyanine pigment (Fastogen Blue 8120B, product of Dainippon Ink and Chemicals, Incorporated) (30 parts) serving as a charge generation material was dispersed in cyclohexanone (970 parts) by a ball mill for two hours, to thereby prepare a charge generation material-dispersed mixture. Separately, a polycarbonate resin (Zpolyca, viscosity average molecular weight: 40,000, product of TEIJIN CHEMICALS LTD.) (49 parts), a naphthalenetetracarboxylic acid diimide derivative (the aforementioned Compound (1), serving as a charge transport material) (20 parts), the following compound (A-i) (29.5 parts) serving as a charge transport material and silicone oil (KF50-100CS, product of Shin-Etsu Chemicals Co., Ltd) (0.1 parts) were dissolved in tetrahydrofuran (340 parts). The above-prepared charge generation material-dispersed mixture (66.6 parts) was added to the solution, followed by stirring, to thereby prepare a coating liquid for forming a photoconductive layer (photoconductive layer-coating liquid).
An aluminum drum (diameter: 30 mm, length: 340 mm), which has a circular run-out of 20 μm or less, was immersed into and lifted from the above-prepared photoconductive layer-coating liquid so as to form a photoconductive layer thereon (thickness: 25 μm), followed by drying at 120° C. for 15 minutes.

The thus-fabricated electrophotographic photoconductor was mounted in a remodeled IPSiO Color 8100 (product of Ricoh Company, Ltd.), wherein a wavelength of LD for writing was set to 780 nm and a power pack was changed for positive charging. Subsequently, the remodeled IPSiO Color 8100 was caused to continuously print out 50,000 sheets of the full-color image in which rectangular patches and characters were mixed with an image area ratio of 6%. The electrophotographic photoconductor was evaluated in the initial state or after printing of 50,000 sheets, in terms of image quality, electric potential at light-exposed areas (exposed-area potential) and electric potential at light-unexposed areas (unexposed-area potential).

Specifically, image quality, exposed-area potential and unexposed-area potential were determined as follows.

Unexposed-area potential: electric potential of the photoconductor surface that has been moved, after primarily charged, to a position for developing (in this test, the charger was adjusted to apply a voltage of +700V from the beginning to the end)

Exposed-area potential: electric potential of the photoconductor surface that has been moved, after charged and imagewise-light-exposed (entirely exposed), to a position for developing Image quality: based on the presence or absence, in output full-color images, of background smears caused by ununiformity in charging (when background smear was observed in a white portion, the electrophotographic photoconductor is rated as "B", and otherwise rated as "A")

Formula (A-i)

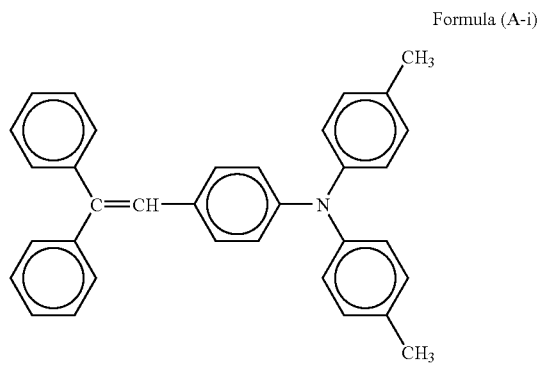

Results

TABLE 19

|  | Unexposed-area potential + V) | Exposed-area potential + V) | Image quality |
|---|---|---|---|
| Initial state | 700 | 85 | A |
| After 50,000 printing | 680 | 120 | A |

The data obtained from the test indicate that the present naphthalenetetracarboxylic acid diimide derivative exhibits excellent electron transferrability, and is advantageously used in an electrophotographic photoconductor as an organic photoconductor material.

Example 22

(Electrophotographic Photoconductor)

According to Example 3 of JP-A No. 2007-108682, the present electrophotographic photoconductor was fabricated as follows.

A metal-free phthalocyanine pigment (Fastogen Blue 8120B, product of Dainippon Ink and Chemicals, Incorporated) (30 parts) serving as a charge generation material was dispersed in cyclohexanone (970 parts) by a ball mill for two hours, to thereby prepare a charge generation material-dispersed mixture. Separately, a polycarbonate resin (Zpolyca, viscosity average molecular weight: 40,000, product of TEIJIN CHEMICALS LTD.) (49 parts), a naphthalenetetracarboxylic acid diimide derivative of Example 16 (20 parts), a charge transport material having the following structural formula (iv) (29.5 parts) and silicone oil (KF50-100CS, product of Shin-Etsu Chemicals Co., Ltd) (0.1 parts) were dissolved in tetrahydrofuran (340 parts). The above-prepared charge generation material-dispersed mixture (66.6 parts) was added to the solution, followed by stirring, to thereby prepare a coating liquid for forming a photoconductive layer (photoconductive layer-coating liquid).

An aluminum drum (diameter: 30 mm, length: 340 mm), which has a circular run-out of 20 μm or less, was immersed into and lifted from the above-prepared photoconductive layer-coating liquid so as to form a photoconductive layer thereon (thickness: 25 μm), followed by drying at 120° C. for 15 minutes.

The thus-fabricated electrophotographic photoconductor was mounted in a remodeled IPSiO Color 8100 (product of Ricoh Company, Ltd.), wherein a wavelength of LD for writing was set to 780 nm and a power pack was changed for positive charging. Subsequently, the remodeled IPSiO Color 8100 was caused to continuously print out 50,000 sheets of the full-color image in which rectangular patches and characters were mixed with an image area ratio of 6%. The electrophotographic photoconductor was evaluated in the initial state or after printing of 50,000 sheets, in terms of image quality, exposed-area potential and unexposed-area potential. Specifically, image quality, exposed-area potential and unexposed-area potential were determined as follows.

Unexposed-area potential: electric potential of the photoconductor surface that has been moved, after primarily charged, to a position for developing (in this test, the charger was adjusted to apply a voltage of +700V from the beginning to the end)

Exposed-area potential: electric potential of the photoconductor surface that has been moved, after charged and imagewise-light-exposed (entirely exposed), to a position for developing Image quality: based on the presence or absence, in output full-color images, of background smears caused by ununiformity in charging (when background smear was observed in a white portion, the electrophotographic photoconductor is rated as "B", and otherwise rated as "A")

Structural Formula (iv)

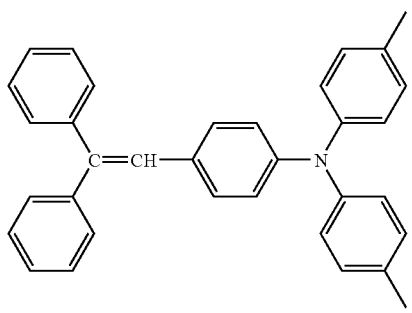

(Results)
(Initial State)
Unexposed-area potential: 700 (V)
Exposed-area potential: 80 (V)
Image quality: A
(After Printing of 50,000 Sheets)
Unexposed-area potential: 690 (V)
Exposed-area potential: 105 (V)
Image quality: A The data obtained from the test indicate that the present naphthalenetetracarboxylic acid diimide derivative exhibits excellent electron transferrability, and is advantageously used in an electrophotographic photoconductor as an organic photoconductor material.

Example 23

On an aluminum cylinder are sequentially coated, by immersion coating, an underlying layer-coating liquid, a charge generation layer-coating liquid and a charge transport layer-coating liquid, each having the following composition, followed by drying, to thereby form an underlying layer (thickness: 3.5 μm), a charge generation layer (thickness: 0.2 μm) and a charge transport layer (thickness: 23 μm) (photoconductor No. 2).
Underlying Layer-coating Liquid
  Titanium dioxide powder (product of ISHIHARA SANGYO KAISHA LTD., TIPAQUE CR-EL): 400 parts
  Melamine resin (product of Dainippon Ink and Chemicals, Incorporated, SUPER BECKAMINE G821-60): 65 parts
  Alkyd resin (product of Dainippon Ink and Chemicals, Incorporated, BECKOLITE M6401-50): 120 parts
  2-Butanone: 400 parts
Charge Generation Layer-coating Liquid
  Fluorenone bisazo pigment having the following structural formula (v): 12 parts
  Polyvinyl butyral (product of Union Carbide Corporation, XYHL): 5 parts
  2-Butanone: 200 parts
  Cyclohexanone: 400 parts
Charge Transport Layer-coating Liquid
  Polycarbonate resin (Zpolyca, product of TEIJIN CHEMICALS LTD.): 10 parts
  Compound No. 8 naphthalenetetracarboxylic acid diimide derivative: 10 parts
  Tetrahydrofuran: 100 parts The thus-fabricated electrophotographic photoconductor was mounted in an electrophotographic process cartridge. The electrophotographic process cartridge was mounted in a remodeled imagio MF2200 (product of Ricoh Company, Ltd.), employing a positive corona charging method and a laser diode (LD, wavelength: 655 nm) serving as a light source for imagewise light exposure. The remodeled imagio MF2200 was set to 800 (V) in unexposed-area potential, and then repeatedly underwent a printing test. The repeated printing tests were comparable to continuous printing of 100,000 sheets. In this test, the quality of an initial image or an image printed out after printing of 100,000 sheets was evaluated. Image blur (dot resolution) of the image was determined as follows: before and after printing of 100,000 sheets, the remodeled imagio MF2200 was caused to continuously print out 10 sheets of a dotted image having a pixel density of 600 dpi×600 dpi and having an image density of 5%; the shape of the formed dots was observed under a stereomicroscope; and edge sharpness was evaluated according to the following five ratings (notably, the rating 5 is the best, and the rating 1 is the worst).
(Ratings for Dotted Image Evaluation)
5: Sharp edge observed, good
4: Blur edge very slightly observed, but good
3: Blur edge slightly observed, but virtually good
2: Blur edge observed, and problematic depending on the type of image
1: Dots indistinguishable from one another
  The results are shown in Table 20.

Examples 24 to 37 (Electrophotographic Photoconductors)

The procedure of Example 23 was repeated, except that the Compound No. 8 naphthalenetetracarboxylic acid diimide derivative was changed to each of Compounds 1, 3, 5, 7, 9, 11, 13, 15, 17, 21, 23, 20 25, 29 and 33 shown in Table 20, to thereby fabricate and analyze electrophotographic photoconductors Nos. 3 to 16. The results are shown in Table 20.

Structural Formula (v)

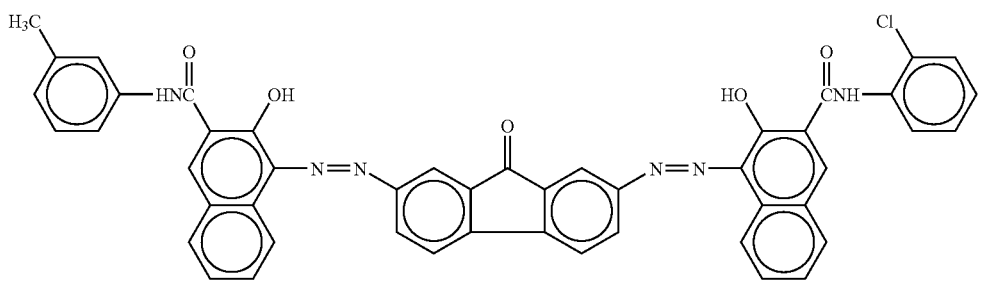

TABLE 20

| Ex. No. | Photo-conductor No. | Compound No. | Initial state Exposed-area potential (V) | Dot resolution | After 100,000 printing Exposed-area potential (V) | Dot resolution |
|---|---|---|---|---|---|---|
| 23 | 2 | 8 | 100 | 5 | 120 | 5 |
| 24 | 3 | 1 | 105 | 5 | 130 | 5 |
| 25 | 4 | 3 | 95 | 5 | 125 | 5 |
| 26 | 5 | 5 | 105 | 5 | 115 | 5 |
| 27 | 6 | 7 | 100 | 5 | 110 | 5 |
| 28 | 7 | 9 | 100 | 5 | 130 | 5 |
| 29 | 8 | 11 | 95 | 5 | 125 | 5 |
| 30 | 9 | 13 | 120 | 5 | 150 | 4 |
| 31 | 10 | 15 | 105 | 5 | 115 | 4 |
| 32 | 11 | 17 | 120 | 5 | 150 | 5 |
| 33 | 12 | 21 | 95 | 5 | 140 | 4 |
| 34 | 13 | 23 | 110 | 5 | 135 | 5 |
| 35 | 14 | 25 | 100 | 5 | 145 | 3 |
| 36 | 15 | 29 | 105 | 5 | 125 | 5 |
| 37 | 16 | 33 | 95 | 5 | 130 | 5 |

Example 38

The procedure of Example 23 was repeated, except that the charge transport layer-coating liquid was changed to a charge transport layer-coating liquid having the following composition, and that negative corona charging (scorotron) was employed for charging, to thereby fabricate and evaluate an electrophotographic photoconductor No. 17. The results are shown in Table 21.

Charge Transport Layer-coating Liquid

Polycarbonate resin (Zpolyca, product of TEIJIN CHEMICALS LTD.): 10 parts

Compound 8 naphthalenetetracarboxylic acid diimide derivative: 1 part

Charge transport material having the following structural formula (I-3): 9 parts

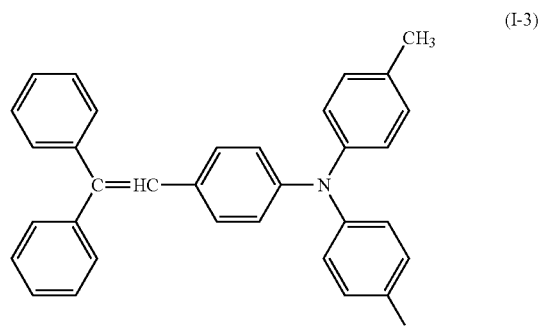

(I-3)

Tetrahydrofuran: 100 parts

Examples 39 to 52

The procedure of Example 38 was repeated, except that the Compound No. 8 naphthalenetetracarboxylic acid diimide derivative was changed to each of Compounds 1, 3, 5, 7, 9, 11, 13, 15, 17, 21, 23, 25, 29 and 33 shown in Table 21, to thereby fabricate electrophotographic photoconductors Nos. 18 to 31. The results are shown in Table 21.

TABLE 21

| Ex. No. | Photo-conductor No. | Compound No. | Initial state Exposed-area potential (V) | Dot resolution | After 100,000 printing Exposed-area potential (V) | Dot resolution |
|---|---|---|---|---|---|---|
| 38 | 17 | 8 | −90 | 5 | −115 | 5 |
| 39 | 18 | 1 | −95 | 5 | −110 | 5 |
| 40 | 19 | 3 | −95 | 5 | −105 | 5 |
| 41 | 20 | 5 | −90 | 5 | −105 | 5 |
| 42 | 21 | 7 | −100 | 5 | −115 | 5 |
| 43 | 22 | 9 | −95 | 5 | −105 | 5 |
| 44 | 23 | 11 | −100 | 5 | −115 | 5 |
| 45 | 24 | 13 | −90 | 5 | −105 | 4 |
| 46 | 25 | 15 | −100 | 5 | −100 | 5 |
| 47 | 26 | 17 | −105 | 5 | −110 | 5 |
| 48 | 27 | 21 | −95 | 5 | −105 | 4 |
| 49 | 28 | 23 | −115 | 5 | −115 | 5 |
| 50 | 29 | 25 | −100 | 5 | −105 | 5 |
| 51 | 30 | 29 | −105 | 5 | −110 | 4 |
| 52 | 31 | 33 | −100 | 5 | −105 | 5 |

Examples 53 to 56

The procedure of Example 38 was repeated, except that the Compound No. 8 naphthalenetetracarboxylic acid diimide derivative was changed to each of Compounds 1, 16, 20 and 30; and that the charge transport material No. I-3 content of the charge transport layer-coating liquid was changed to 7 parts, to thereby fabricate and evaluate electrophotographic photoconductors 32 to 35. The results are shown in Table 22.

Naphthalenetetracarboxylic acid diimide derivative: 1 part

Charge transport material No. I-3: 7 parts

TABLE 22

| Ex. No. | Photo-conductor No. | Compound No. | Initial state Exposed-area potential (V) | Dot resolution | After 100,000 printing Exposed-area potential (V) | Dot resolution |
|---|---|---|---|---|---|---|
| 53 | 32 | 1 | −100 | 5 | −105 | 5 |
| 54 | 33 | 16 | −95 | 5 | −105 | 5 |
| 55 | 34 | 20 | −95 | 5 | −105 | 4 |
| 56 | 35 | 30 | −100 | 5 | −105 | 5 |

Examples 57 to 60

The procedure of Example 53 was repeated, except that the charge transport material (I-3) was changed to a charge transport material (II-3) given below, to thereby fabricate and evaluate electrophotographic photoconductors Nos. 36 to 39. The results are shown in Table 23.

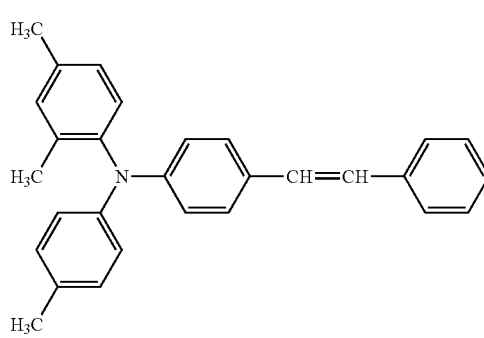 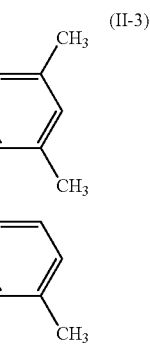

(II-3)

TABLE 23

| Ex. No. | Photo-conductor No. | Compound No. | Initial state Exposed-area potential (V) | Dot resolution | After 100,000 printing Exposed-area potential (V) | Dot resolution |
|---|---|---|---|---|---|---|
| 57 | 36 | 1  | −95  | 5 | −100 | 5 |
| 58 | 37 | 16 | −90  | 5 | −110 | 5 |
| 59 | 38 | 20 | −90  | 5 | −110 | 4 |
| 60 | 39 | 30 | −95  | 5 | −105 | 5 |

Examples 61 to 64

The procedure of Example 53 was repeated, except that the charge transport material (I-3) was changed to a charge transport material (III-3) given below, to thereby fabricate and evaluate electrophotographic photoconductors Nos. 40 to 43. The results are shown in Table 24.

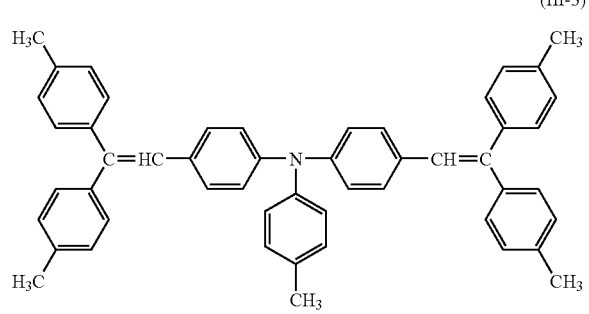

(III-3)

Examples 65 to 68

The procedure of Example 53 was repeated, except that the charge transport material (I-3) was changed to a charge transport material (IV-3) given below, to thereby fabricate and evaluate electrophotographic photoconductors Nos. 44 to 47. The results are shown in Table 25.

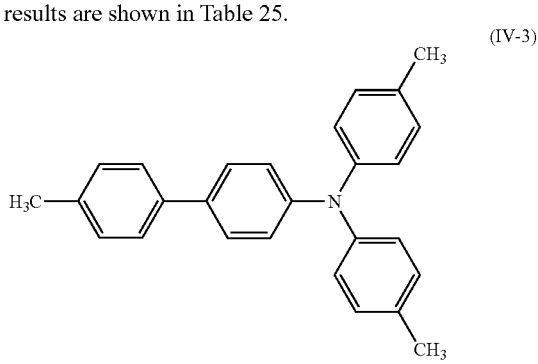

(IV-3)

TABLE 25

| Ex. No. | Photo-conductor No. | Compound No. | Initial state Exposed-area potential (V) | Dot resolution | After 100,000 printing Exposed-area potential (V) | Dot resolution |
|---|---|---|---|---|---|---|
| 65 | 44 | 1  | −100 | 5 | −110 | 5 |
| 66 | 45 | 16 | −100 | 5 | −115 | 5 |
| 67 | 46 | 20 | −95  | 5 | −110 | 4 |
| 68 | 47 | 30 | −105 | 5 | −115 | 5 |

TABLE 24

| Ex. No. | Photoconductor No. | Compound No. | Initial state Exposed-area potential (V) | Dot resolution | After 100,000 printing Exposed-area potential (V) | Dot resolution |
|---|---|---|---|---|---|---|
| 61 | 40 | 1  | −95  | 5 | −105 | 5 |
| 62 | 41 | 16 | −100 | 5 | −105 | 5 |
| 63 | 42 | 20 | −105 | 5 | −100 | 4 |
| 64 | 43 | 30 | −95  | 5 | −110 | 5 |

Examples 69 and 70

The procedure of Example 38 was repeated, except that the charge generation layer-coating liquid was changed to a charge generation layer-coating liquid having the following composition; and that the charge transport layer-coating liquid was changed to a charge transport layer-coating liquid having the following composition, to thereby fabricate and evaluate electrophotographic photoconductors 48 and 49. The results are shown in Table 26.

<Production of Oxotitanium Phthalocyanine>

Similar to Synthesis Example 4 of JP-A No. 2001-019871, oxotitanium phthalocyanine was produced. Specifically, 1,3-diiminoisoindoline (29.2 g) was mixed with sulfolane (200 mL), and titanium tetrabutoxide (20.4 g) was added dropwise to the mixture under a stream of nitrogen. After completion of dropwise addition, the resultant mixture was gradually heated to 180° C. The mixture was allowed to react under stirring for five hours, while the reaction temperature was maintained to a temperature of 170° C. to 180° C. After completion of reaction, the reaction mixture was left to cool. The matter that precipitates was filtered, and the obtained powder was washed with chloroform until it assumed blue color. The obtained blue powder was washed with methanol several times, and then further washed with hot water (80° C.) at several times, to thereby produce crude titanyl phthalocyanine. The crude titanyl phthalocyanine was dissolved in 20 volumes of concentrated sulfuric acid, and the solution was added dropwise to 100 volumes of ice water under stirring. The crystals that precipitate were filtered, and the obtained crystals were washed repeatedly with water until the wash liquid had a neutral pH, to thereby produce a wet cake of a titanyl phthalocyanine pigment. Notably, the cake, in a dried state, exhibited an X-ray diffraction spectrum shown in FIG. 10. The above-obtained wet cake (2 g) was mixed under stirring with carbon disulfide (20 g) for four hours. Methanol (100 g) was further added to the mixture, followed by stirring (for one hour), filtration and drying, to thereby produce oxotitanium phthalocyanine crystal powder.

Charge Generation Layer-coating Liquid

Figure 10:
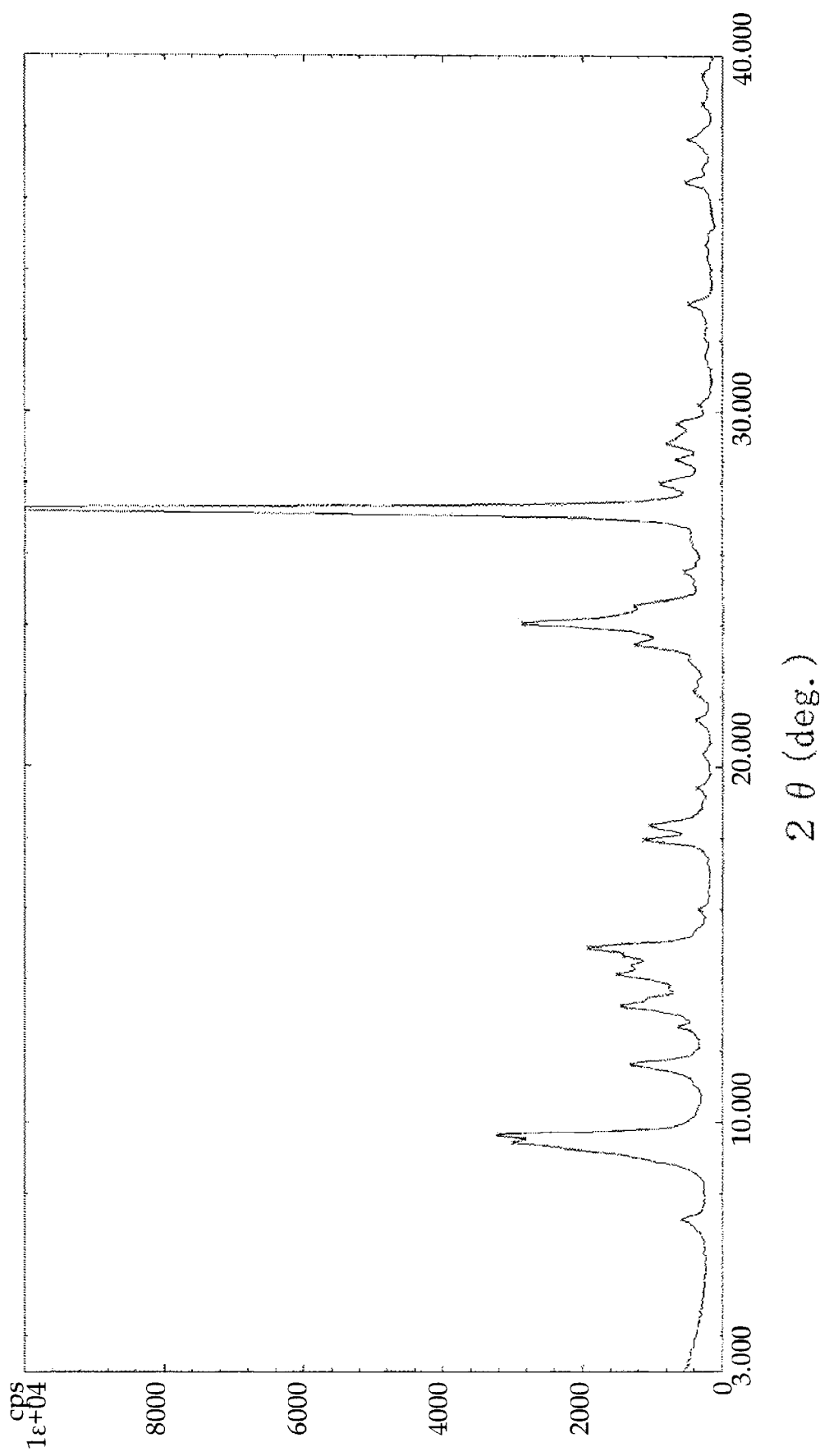
FIG. 10 is a powder XD spectrum chart of oxotitanium phthalocyanine.

Oxotitanium phthalocyanine exhibiting a powder XD spectrum as shown in FIG. 10: 8 parts
Polyvinyl butyral (BX-1): 5 parts
2-Butanone: 400 parts Charge Transport Layer-coating Liquid Polycarbonate resin (Zpolyca): 10 parts Naphthalenetetracarboxylic acid diimide derivative: 1 part Charge transport material (I-3) having the following structural formula: 7 parts

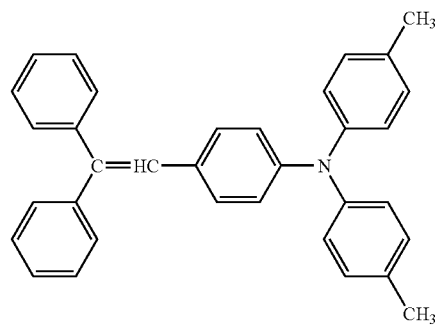

(I-3)

Toluene: 70 parts

TABLE 26

| | | | Initial state | | After 100,000 printing | |
|---|---|---|---|---|---|---|
| Ex. No. | Photo-conductor No. | Com-pound No. | Exposed-area potential (V) | Dot resolution | Exposed-area potential (V) | Dot reso-lution |
| 69 | 48 | 7 | −110 | 5 | −125 | 5 |
| 70 | 49 | 30 | −105 | 5 | −120 | 4 |

Example 71

A photoconductive layer-coating liquid having the following composition was coated on an aluminum cylinder (diameter: 100 mm), followed by drying, to thereby fabricate an electrophotographic photoconductor having a single-layer photoconductive layer (thickness: 30 μm) (Photoconductor No. 50).

[Photoconductive Layer-coating Liquid]

X-Type metal-free phthalocyanine (Fastogen Blue 8120B: product of Dainippon Ink and Chemicals, Incorporated): 2 parts Charge transport material (II-3) having the following structural formula: 30 parts

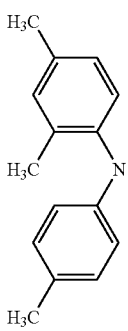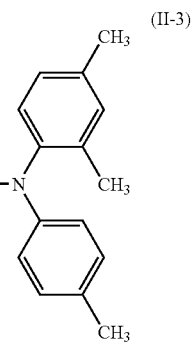

(II-3)

Naphthalenetetracarboxylic acid diimide derivative No. 1: 20 parts

Bisphenol Z polycarbonate (Panlite TS-2050, product of TEIJIN CHEMICALS LTD.): 50 parts Tetrahydrofuran: 500 parts The thus-fabricated electrophotographic photoconductor was mounted in a remodeled imagio Neo 752 (product of Ricoh Company, Ltd.), employing a corona charging method (using a scorotron type corona charger) and a laser diode (LD, wavelength: 780 nm) serving as a light source for imagewise light exposure. The remodeled imagio Neo 752 was set to +700 (V) in unexposed-area potential (surface), and then repeatedly underwent a printing test. The repeated printing tests were comparable to continuous printing of 100,000 sheets. In this test, the quality of an initial image was evaluated, and an image printed out after printing of 100,000 sheets was evaluated for its quality and exposed-area potential. Similar to Example 27, image blur (dot resolution) of the image was determined. The results are shown in Table 27.

Examples 72 to 74

The procedure of Example 71 was repeated, except that the naphthalenetetracarboxylic acid diimide derivative No. 1 (Compound No. 1) was changed to each of Compound Nos. 16, 20 and 30 shown in Table 27, to thereby fabricate and evaluate the electrophotographic photoconductor of the present invention.

TABLE 27

| Ex. No. | Photo-conductor No. | Com-pound No. | Initial state Exposed-area potential (V) | Dot resolution | After 100,000 printing Exposed-area potential (V) | Dot resolution |
|---|---|---|---|---|---|---|
| 71 | 50 | 1 | 95 | 5 | 110 | 5 |
| 72 | 51 | 16 | 105 | 5 | 115 | 5 |
| 73 | 52 | 20 | 100 | 5 | 110 | 5 |
| 74 | 53 | 30 | 105 | 5 | 115 | 5 |

Example 75

The same photoconductive layer-coating liquid as used in Example 71 was coated on an aluminum cylinder (diameter: 30 mm), followed by drying, to thereby fabricate an electrophotographic photoconductor having a single-layer photoconductive layer (thickness: 30 μm) (Photoconductor No. 54).

Similar to Example 38, the thus-obtained photoconductive layer was evaluated. The results are shown in Table 28.

Examples 76 to 78

The procedure of Example 75 was repeated, except that the naphthalenetetracarboxylic acid diimide derivative No. 1 was changed to Compound Nos. 16, 20 and 30 shown in Table 28, to thereby fabricate the electrophotographic photoconductor of the present invention.

TABLE 28

| Ex. No. | Photo-conductor No. | Com-pound No. | Initial state Exposed-area potential (V) | Dot resolution | After 100,000 printing Exposed-area potential (V) | Dot resolution |
|---|---|---|---|---|---|---|
| 75 | 54 | 1 | −95 | 5 | −120 | 5 |
| 76 | 55 | 16 | −100 | 5 | −115 | 4 |
| 77 | 56 | 20 | −100 | 5 | −110 | 4 |
| 78 | 57 | 30 | −105 | 5 | −130 | 4 |

Example 79

A charge transport layer-coating liquid having the following composition and a charge generation layer-coating liquid having the lo following composition were sequentially coated on an aluminum cylinder (diameter: 100 mm), followed by drying, to thereby fabricate an electrophotographic photoconductor having a charge transport layer (thickness: 20 μm) and a charge generation layer (thickness: 0.1 μm) (Photoconductor No. 58). Similar to Example 71, the electrophotographic photoconductor was evaluated. The results are shown in Table 29.

(Compostion of Charge Transport Layer-coating Liquid)
  Bisphenol A polycarbonate (Panlite C-1400, product of TEIJIN CHEMICALS LTD.): 10 parts
  Toluene: 100 parts
  Naphthalenetetracarboxylic acid diimide derivative No. 1:10 parts
(Composition of Charge Generation Layer-coating Liquid)
  Polyvinyl butyral (XYHL, product of UCC): 0.5 parts
  Cyclohexanone: 200 parts
  Methyl ethyl ketone: 80 parts
  X-Type metal-free phthalocyanine (Fastogen Blue 8120B: product of Dainippon Ink and Chemicals, Incorporated): 2 parts Examples 80 to 82

The procedure of Example 79 was repeated, except that the naphthalenetetracarboxylic acid diimide derivative No. 1 was changed to each of Compounds 16, 20 and 30 shown in Table 29, to thereby fabricate and evaluate the electrophotographic photoconductor of the present invention.

TABLE 29

| Ex. No. | Photo-conductor No. | Com-pound No. | Initial state Exposed-area potential (V) | Dot resolution | After 100,000 printing Exposed-area potential (V) | Dot resolution |
|---|---|---|---|---|---|---|
| 79 | 58 | 1 | −100 | 5 | −115 | 5 |
| 80 | 59 | 16 | −90 | 5 | −110 | 5 |
| 81 | 60 | 20 | −110 | 5 | −115 | 5 |
| 82 | 61 | 30 | −105 | 5 | −110 | 5 |

Comparative Example 1

The procedure of Example 23 was repeated, except that the naphthalenetetracarboxylic acid diimide derivative No. 8 was changed to a benzoquinone derivative having the following structural formula (I-4), to thereby fabricate and evaluate comparative electrophotographic photoconductor No. 1. The results are shown in Table 30.

(I-4)

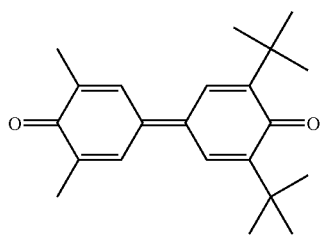

Comparative Example 2

The procedure of Example 38 was repeated, except that there was used a charge transport layer-coating liquid containing no naphthalenetetracarboxylic acid diimide derivative and containing the charge transport material (I-3) in an amount of 10 parts, to thereby fabricate and evaluate comparative electrophotographic photoconductor No. 2. The results are shown in Table 30.

Comparative Example 3

The procedure of Example 57 was repeated, except that the naphthalenetetracarboxylic acid diimide derivative was changed to a tetraphenylmethane compound having the following structural formula (I-5) (described in JP-A No. 2000-231204), to thereby fabricate and evaluate comparative electrophotographic photoconductor No. 3. The results are shown in Table 30.

(I-5)

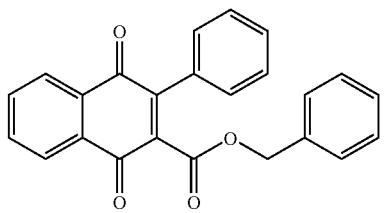

Comparative Example 4

The procedure of Example 69 was repeated, except that the naphthalenetetracarboxylic acid diimide derivative was changed to a hindered amine antioxidant having the following structural formula (I-6), to thereby fabricate and evaluate comparative electrophotographic photoconductor No. 4. The results are shown in Table 30.

(I-6)

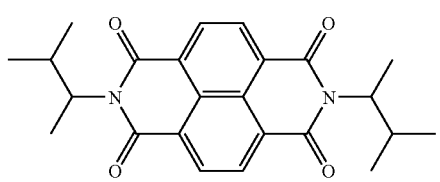

Comparative Example 5

The procedure of Example 71 was repeated, the naphthalenetetracarboxylic acid diimide derivative No. 1 (20 parts) was changed to a charge transport material having the following structural formula (I-7) (18 parts) and a charge transport material having the following structural formula (I-8) (2 parts), to thereby fabricate and evaluate comparative electrophotographic photoconductor No. 5. The results are shown in Table 30.

(I-7)

(I-8)

Comparative Example 6

The procedure of Example 71 was repeated, the naphthalenetetracarboxylic acid diimide derivative No. 1 (20 parts) was changed to a charge transport material having the following structural formula (I-9) (20 parts), to thereby fabricate and evaluate comparative electrophotographic photoconductor No. 6. The results are shown in Table 30.

(I-9)

Comparative Example 7

The procedure of Example 80 was repeated, except that the naphthalenetetracarboxylic acid diimide derivative No. 1 (10 parts) was changed to a charge transport material having the following structural formula (I-10) (9 parts) and a charge transport material having the following structural formula (I-11) (1 part), to thereby fabricate and evaluate comparative electrophotographic photoconductor No. 7. The results are shown in Table 30.

(I-10)

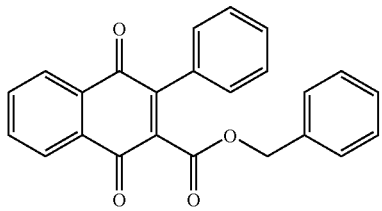

(I-11)

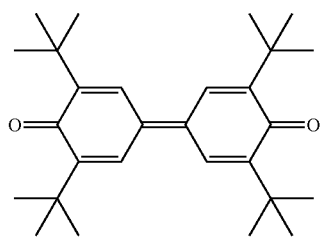

TABLE 30

| Comp. Ex. No. | Comparative photoconductor No. | Initial state | | After 100,000 printing | |
|---|---|---|---|---|---|
| | | Exposed-area potential (V) | Dot resolution | Exposed-area potential (V) | Dot resolution |
| 1 | 1 | +250 | 3 | +440 | 1 |
| 2 | 2 | −100 | 5 | −135 | 2 |
| 3 | 3 | −200 | 4 | −285 | 3 |
| 4 | 4 | −250 | 2 | −480 | 1 |
| 5 | 5 | +105 | 5 | +145 | 1 |
| 6 | 6 | +110 | 4 | +155 | 1 |
| 7 | 7 | −100 | 4 | −120 | 1 |

As is clear from the obtained data, the photoconductors containing the present naphthalenetetracarboxylic acid diimide derivative exhibited less increase in exposed-area potential even after printing of 100,000 sheets, indicating that it can consistently provide high-quality images. In contrast, comparative photoconductors 1, 3 and 4 have a considerably high exposed-area potential, causing deterioration of image density and resolution. After printing of 100,000 sheets, these compounds provided an image having dots indistinguishable from one another due to considerably reduced gradation properties. As is clear from the data shown in Tables 20 and 26, the present photoconductor provided an excellent image even when applied to a positively charging method or even after printing of 100,000 sheets, and exhibited reduced image blur (high dot resolution). Separately, although comparative photoconductors 2, 5, 6 and 7 exhibited less increase in exposed-area potential than the other comparative photoconductors, they exhibited a greater drop in resolution than the present photoconductor after repeatedly used.

Examples 83 to 89 and Comparative Example 8

The electrophotographic photoconductors of the present invention and a comparative photoconductor 2 were left to stand for four days in a desiccator where the nitrogen oxide (NOx) gas concentration had been adjusted to 50 ppm. Thereafter, an image was formed using each of the photoconductors, and the thus-formed image was compared with an image obtained prior to the above treatment.

TABLE 31

| Ex. No. | Photoconductor No. | Initial image quality | Image quality after being left to stand |
|---|---|---|---|
| 83 | 2 | 5 | 5 |
| 84 | 18 | 5 | 5 |
| 85 | 34 | 5 | 5 |
| 86 | 38 | 5 | 4 |
| 87 | 49 | 5 | 5 |
| 88 | 50 | 5 | 4 |
| 89 | 60 | 5 | 5 |
| Comp. Ex. 8 | Comp. photoconductor 2 | 5 | 1 |

As is clear from the data shown in Table 31, the photoconductor containing the present naphthalenetetracarboxylic acid diimide derivative exhibited considerably enhanced preventive effects against a drop in resolution; i.e., in resistance to oxidation gas. Meanwhile, although the comparative photoconductor 2 initially exhibited good image quality, it exhibited a considerable drop in resolution due to the action of oxidation gas.

What is claimed is:

1. A naphthalenetetracarboxylic acid diimide derivative represented by the following general formula (1):

General Formula (1)

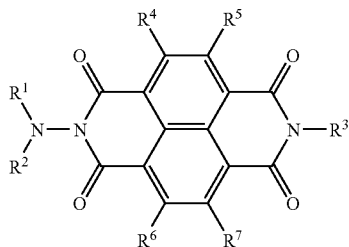

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; with compounds where all of $R^1$, $R^2$ and $R^3$ are a methyl group, and compounds where both of $R^1$ and $R^2$ are a methyl group and $R^3$ is a 1-octyl group being excluded.

2. A naphthalenetetracarboxylic acid diimide derivative represented by the following general formula (I):

General Formula (I)

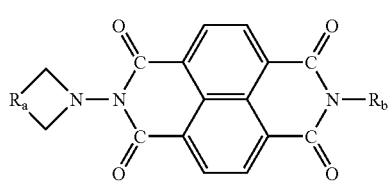

wherein $R_a$ represents a divalent group necessary for forming a nitrogen-containing ring together with a nitrogen atom and a carbon atom; a nitrogen-containing ring moiety represented by the following general formula (II) represents an alkyl-substituted or non-substituted piperidine, an alkyl-substituted or non-substituted pyrrolidine, an alkyl-substituted or non-substituted homopiperkline, an alkyl-substituted or non-substituted piperazine, or an alkyl-substituted or non-substituted morpholine wherein in a case that the heterocyclic group is substituted, the substituent is an alkyl group; and $R_b$ represents an amino-substituted or non-substituted branched alkyl group or an amino-substituted or non-substituted branched alkoxyalkyl group:

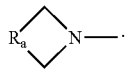

General Formula (II)

3. An electrophotographic photoconductor comprising a conductive support and a photoconductive layer provided on the conductive support, wherein the photoconductive layer contains a first charge transport material containing a naphthalenetetracarboxylic acid diimide derivative represented by the following general formula (1) or (I):

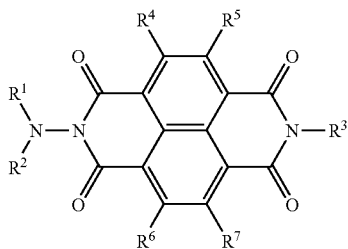

General Formula (1)

wherein $R^1$ and $R^2$, which are identical or different, each represent a substituted or non-substituted alkyl group or a substituted or non-substituted aromatic hydrocarbon group; $R^3$ represents an alkyl group having 1 to 8 carbon atoms or an aromatic hydrocarbon group; $R^4$, $R^5$, $R^6$ and $R^7$, which are identical or different, each represent a hydrogen atom, a substituted or non-substituted alkyl group, or a substituted or non-substituted aromatic hydrocarbon group; with compounds where all of $R^1$, $R^2$ and $R^3$ are a methyl group, and compounds where both of $R^1$ and $R^2$ are a methyl group and $R^3$ is a 1-octyl group being excluded;

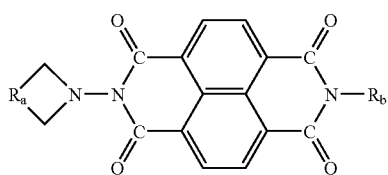

General Formula (I)

wherein $R_a$ represents a divalent group necessary for forming a nitrogen-containing ring together with a nitrogen atom and a carbon atom; a nitrogen-containing ring moiety represented by the following general formula (II) represents an alkyl-substituted or non-substituted piperidine, an alkyl-substituted or non-substituted pyrrolidine, an alkyl-substituted or non-substituted homopiperidine, an alkyl-substituted or non-substituted piperazine, or an alkyl-substituted or non-substituted morpholine, wherein in a case that the heterocyclic group substituted, the substituent is an alkyl group; and $R_b$ represents an amino-substituted or non-substituted branched alkyl group or an amino-substituted or non-substituted branched alkoxyalkyl group:

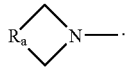

General Formula (II)

4. The electrophotographic photoconductor according to claim 3, wherein the photoconductive layer further contains a second charge transport material.

5. The electrophotographic photoconductor according to claim 4, wherein the second charge transport material is a derivative represented by the following general formula (2):

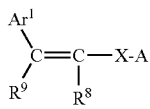

General Formula (2)

wherein X represents a single bond or a vinylene group; $R^8$ represents a hydrogen atom, a substituted or non-substituted alkyl group, or a substituted or non-substituted aromatic hydrocarbon group; $Ar^1$ represents a substituted or non-substituted aromatic hydrocarbon group; $R^9$ represents a hydrogen atom, a substituted or non-substituted alkyl group, or a substituted or non-substituted aromatic hydrocarbon group; $Ar^1$ and $R^9$ may be linked to form a ring; and A represents a group represented by the following general formula (3) or (4), a 9-anthryl group, or a substituted or non-substituted carbazolyl group;

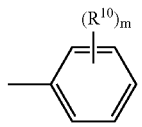

General Formula (3)

wherein $R^{10}$ represents a hydrogen atom, an alkyl group, an alkoxy group, a halogen atom, or a group represented by the following general formula (5); m is an integer of 1 to 3; and when m is two or more, $R^{10}$s may be identical or different;

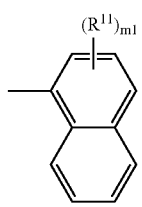

General Formula (4)

wherein $R^{11}$ represents a hydrogen atom, an alkyl group, an alkoxy group, a halogen atom, or a group represented by the following general formula (5); m1 is an integer of 1 to 3; and when m1 is two or more, $R^{11}$s may be identical or different;

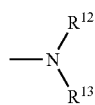

General Formula (5)

wherein $R^{12}$ and $R^{13}$, which may be identical or different, each represent a substituted or non-substituted alkyl group, or a substituted or non-substituted aromatic hydrocarbon group; and $R^{12}$ and $R^{13}$ may be linked to form a ring.

6. The electrophotographic photoconductor according to claim 4, wherein the second charge transport material is a derivative represented by the following general formula (6):

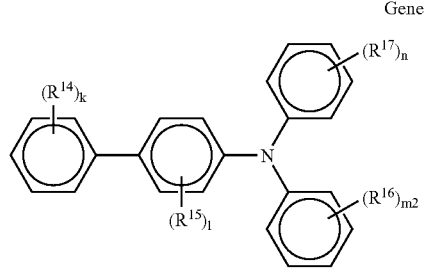

General Formula (6)

wherein $R^{14}$, $R^{16}$ and $R^{17}$ each represent a hydrogen atom, an amino group, an alkoxy group, a thioalkoxy group, an aryloxy group, a methylenedioxy group, a substituted or non-substituted alkyl group, a halogen atom, or a substituted or non-substituted aromatic hydrocarbon group; $R^{15}$ represents a hydrogen atom, an alkoxy group, a substituted or non-substituted alkyl group, or a halogen atom; k, l, m2 or n is an integer of 1, 2, 3 or 4; when k is an integer of 2, 3 or 4, $R^{14}$s may be identical or different; when l is an integer of 2, 3 or 4, $R^{15}$s may be identical or different; when m2 is an integer of 2, 3 or 4, $R^{16}$s may be identical or different; and when n is an integer of 2, 3 or 4, $R^{17}$s may be identical or different.

7. The electrophotographic photoconductor according to claim 4, wherein the second charge transport material is a derivative represented by the following general formula (7):

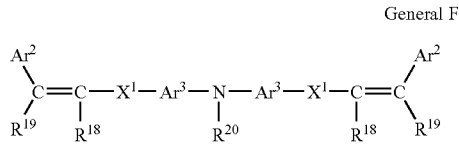

General Formula (7)

wherein $X^1$ represents a single bond or a vinylene group; $R^{18}$ represents a hydrogen atom, a substituted or non-substituted alkyl group, or a substituted or non-substituted aromatic hydrocarbon group; $Ar^2$ represents a substituted or non-substituted aromatic hydrocarbon group; $R^{19}$ represents a hydrogen atom, a substituted or non-substituted alkyl group, or a substituted or non-substituted aromatic hydrocarbon group; $Ar^2$ and $R^{19}$ may be linked to form a ring; $Ar^3$ represents a divalent group represented by the following general formula (8) or (9); and $R^{20}$ represents a substituted or non-substituted alkyl group, or a substituted or non-substituted aromatic hydrocarbon group;

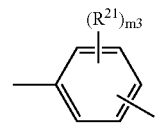

General Formula (8)

wherein $R^{21}$ represents a hydrogen atom, an alkyl group, an alkoxy group or a halogen atom; m3 is an integer of 1 to 3; and when m3 is two or more, $R^{21}$s may be identical or different;

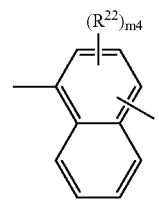

General Formula (9)

wherein $R^{22}$ represents a hydrogen atom, an alkyl group, an alkoxy group or a halogen atom; m4 is an integer of 1 to 3; and when m4 is two or more, $R^{22}$s may be identical or different.

8. The electrophotographic photoconductor according to claim 4, wherein the second charge transport material is a derivative represented by the following general formula (10):

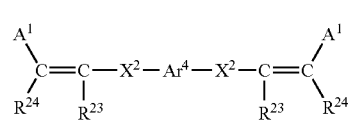

General Formula (10)

wherein $X^2$ represents a single bond or a vinylene group; $R^{23}$ represents a hydrogen atom, a substituted or non-substituted alkyl group, or a substituted or non-substituted aromatic hydrocarbon group; $Ar^4$ represents a substituted or non-substituted divalent aromatic hydrocarbon group; $R^{24}$ represents a hydrogen atom, a substituted or non-substituted alkyl group, or a substituted or non-substituted aromatic hydrocarbon group; and $A^1$ represents a group represented by the following general formula (3) or (4), a 9-anthryl group, or a substituted or non-substituted carbazolyl group;

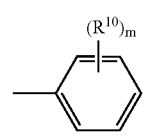

General Formula (3)

wherein $R^{10}$ represents a hydrogen atom, an alkyl group, an alkoxy group, a halogen atom, or a group represented by the following general formula (5); m is an integer of 1 to 3; and when m is two or more, $R^{10}$s may be identical or different;

General Formula (4)

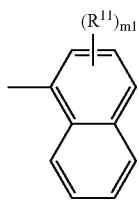

wherein $R^{11}$ represents a hydrogen atom, an alkyl group, an alkoxy group, a halogen atom, a group represented by the following general formula (5); m1 is an integer of 1 to 3; and when m1 is two or more, $R^{11}$s may be identical or different;

General Formula (5)

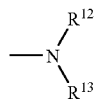

wherein $R^{12}$ and $R^{13}$, which may be identical or different, each represent a substituted or non-substituted alkyl group, or a substituted or non-substituted aromatic hydrocarbon group; and $R^{12}$ and $R^{13}$ may be linked to form a ring.

9. The electrophotographic photoconductor according to claim 3, wherein the photoconductive layer comprises, in sequence, a conductive support, a charge generation layer and a charge transport layer.

10. The electrophotographic photoconductor according to claim 3, wherein the photoconductive layer comprises, in sequence, a conductive support, a charge transport layer and a charge generation layer.

11. The electrophotographic photoconductor according to claim 3, wherein the photoconductive layer has a single-layer structure.

* * * * *